(12) United States Patent
Allan et al.

(10) Patent No.: US 10,328,226 B2
(45) Date of Patent: Jun. 25, 2019

(54) PATIENT INTERFACE AND ASPECTS THEREOF

(71) Applicant: Fisher & Paykel Healthcare Limited, Auckland (NZ)

(72) Inventors: Olivia Marie Allan, Auckland (NZ); Arvin San Jose Gardiola, Auckland (NZ); Lewis George Gradon, Auckland (NZ); Wen Dong Huang, Auckland (NZ); Alastair Edwin McAuley, Auckland (NZ); Mark Arvind McLaren, Auckland (NZ); Craig Robert Prentice, Auckland (NZ); Andrew Paul Maxwell Salmon, Auckland (NZ); Silas Sao Jin Siew, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 15/047,538

(22) Filed: Feb. 18, 2016

(65) Prior Publication Data

US 2016/0166792 A1    Jun. 16, 2016

Related U.S. Application Data

(63) Continuation of application No. 14/887,234, filed on Oct. 19, 2015, now abandoned, which is a
(Continued)

(51) Int. Cl.
*A62B 18/02* (2006.01)
*A61M 16/00* (2006.01)
(Continued)

(52) U.S. Cl.
CPC ........ *A61M 16/0666* (2013.01); *A61M 16/06* (2013.01); *A61M 16/0605* (2014.02);
(Continued)

(58) Field of Classification Search
None
See application file for complete search history.

(56) References Cited

U.S. PATENT DOCUMENTS

| 301,111 A | 7/1884 | Genese |
| 472,238 A | 4/1892 | Van Orden |

(Continued)

FOREIGN PATENT DOCUMENTS

| AU | 2003246441 | 12/2003 |
| CA | 131 16 62 | 12/1992 |

(Continued)

OTHER PUBLICATIONS

International Preliminary Report on Patentability (IPRP), International Application No. PCT/NZ2009/000219, dated Apr. 12, 2011, 9 pages.
(Continued)

*Primary Examiner* — Peter S Vasat
(74) *Attorney, Agent, or Firm* — Knobbe Martens Olson & Bear LLP

(57) ABSTRACT

A patient interface has a single loop headstrap and a mask for covering at least the nostrils of the user. The single loop headstrap extends from the mask at either end. A short length of supple conduit is coupled to the mask by a swivel or ball joint to allow rotation of the conduit relative to the mask through different angles and orientations.

19 Claims, 70 Drawing Sheets

Related U.S. Application Data continuation of application No. 12/945,141, filed on Nov. 12, 2010, which is a continuation-in-part of application No. PCT/NZ2009/000072, filed on May 12, 2009, said application No. 12/945,141 is a continuation-in-part of application No. PCT/EB2010/052061, filed on May 10, 2010.

(60) Provisional application No. 61/052,362, filed on May 12, 2008, provisional application No. 61/376,067, filed on Aug. 23, 2010.

(51) Int. Cl.
*A61M 15/00* (2006.01)
*A61M 16/06* (2006.01)
*A61M 16/08* (2006.01)

(52) U.S. Cl.
CPC .... *A61M 16/0616* (2014.02); *A61M 16/0683* (2013.01); *A61M 16/0816* (2013.01); *A61M 16/0825* (2014.02); *A61M 16/0875* (2013.01); *A61M 2205/0216* (2013.01); *A61M 2205/0238* (2013.01); *A61M 2209/088* (2013.01); *A61M 2210/0618* (2013.01)

(56) References Cited

U.S. PATENT DOCUMENTS

| | | |
|---|---|---|
| 577,926 A | 3/1897 | Miller |
| 718,470 A | 1/1903 | Jones |
| 751,091 A | 2/1904 | Moran |
| 770,013 A | 9/1904 | Linn |
| 1,635,545 A | 7/1927 | Drager |
| 2,126,755 A | 8/1938 | Dreyfus |
| 2,228,218 A | 1/1941 | Schwartz |
| 2,241,535 A | 5/1941 | Boothby et al. |
| 2,296,150 A | 9/1942 | Dockson et al. |
| 2,353,643 A | 7/1944 | Bulbulian |
| 2,359,506 A | 10/1944 | Battley et al. |
| 2,388,604 A | 11/1945 | Eisenbud |
| 2,452,845 A | 11/1948 | Fisher |
| 2,508,050 A | 5/1950 | Valente |
| 2,693,800 A | 11/1954 | Caldwell |
| 2,738,788 A | 3/1956 | Matheson et al. |
| 2,843,121 A | 7/1958 | Hudson |
| 2,859,748 A | 11/1958 | Hudson |
| 2,875,759 A | 3/1959 | Galleher |
| 2,939,458 A | 6/1960 | Lundquist |
| 3,424,633 A | 1/1969 | Corrigall et al. |
| 3,490,452 A | 1/1970 | Greenfield |
| 3,599,635 A | 8/1971 | Kenneth |
| 3,682,171 A | 8/1972 | Dali et al. |
| 3,834,682 A | 9/1974 | McPhee |
| 3,850,171 A | 11/1974 | Ball et al. |
| 3,894,562 A | 7/1975 | Mosley et al. |
| 3,972,321 A | 8/1976 | Proctor |
| 3,977,432 A | 8/1976 | Vidal |
| 3,992,720 A | 11/1976 | Nicolinas |
| 4,090,510 A | 5/1978 | Segersten |
| D250,047 S | 10/1978 | Lewis et al. |
| D250,131 S | 10/1978 | Lewis et al. |
| 4,127,130 A | 11/1978 | Naysmith |
| 4,150,464 A | 4/1979 | Tracy |
| D252,322 S | 7/1979 | Johnson |
| 4,201,205 A | 5/1980 | Bartholomew |
| 4,258,710 A | 3/1981 | Reber |
| 4,266,540 A | 5/1981 | Panzik et al. |
| 4,278,082 A | 7/1981 | Blackmer |
| 4,354,488 A | 10/1982 | Bartos |
| 4,367,735 A | 1/1983 | Dali |
| 4,378,011 A | 3/1983 | Wamcke et al. |
| 4,437,462 A | 3/1984 | Piljay |
| 4,454,880 A | 6/1984 | Muto et al. |
| 4,603,692 A * | 8/1986 | Montesi ............... A62B 18/084 128/207.11 |
| 4,621,632 A | 11/1986 | Bartels et al. |
| 4,644,974 A | 2/1987 | Zingg |
| 4,676,241 A | 6/1987 | Webb et al. |
| D293,613 S | 1/1988 | Wingler |
| 4,753,233 A | 6/1988 | Grimes |
| 4,782,832 A | 11/1988 | Trimble et al. |
| 4,836,200 A * | 6/1989 | Clark ................... A61M 25/02 128/204.18 |
| 4,856,508 A | 8/1989 | Tayebi |
| 4,907,584 A | 3/1990 | McGinnis |
| 4,915,104 A | 4/1990 | Marcy |
| 4,915,105 A | 4/1990 | Lee |
| 4,919,128 A | 4/1990 | Kopala et al. |
| 4,938,209 A | 7/1990 | Fry |
| 4,941,467 A | 7/1990 | Takata |
| 4,944,310 A | 7/1990 | Sullivan |
| D310,431 S | 9/1990 | Bellm |
| 4,958,658 A | 9/1990 | Zajac |
| 4,971,051 A | 11/1990 | Toffolon |
| 4,986,269 A | 1/1991 | Hakkinen |
| 5,010,925 A | 4/1991 | Atkinson et al. |
| 5,016,625 A | 5/1991 | Hsu et al. |
| 5,031,261 A | 7/1991 | Fenner |
| 5,042,478 A | 8/1991 | Kopala et al. |
| D320,677 S | 10/1991 | Kumagai et al. |
| D321,419 S | 11/1991 | Wallace |
| 5,062,421 A | 11/1991 | Burns et al. |
| 5,065,756 A | 11/1991 | Rapoport |
| D322,318 S | 12/1991 | Sullivan et al. |
| 5,074,297 A | 12/1991 | Venegas |
| 5,094,236 A | 3/1992 | Amad |
| 5,113,857 A | 5/1992 | Dickerman et al. |
| 5,121,745 A | 6/1992 | Israel et al. |
| 5,148,802 A | 9/1992 | Sanders et al. |
| 5,164,652 A | 11/1992 | Johnson et al. |
| 5,231,979 A | 8/1993 | Rose et al. |
| 5,243,971 A | 9/1993 | Sullivan et al. |
| 5,245,995 A | 9/1993 | Sullivan et al. |
| D340,317 S | 10/1993 | Cole |
| 5,259,377 A | 11/1993 | Schroeder |
| 5,269,296 A | 12/1993 | Landis et al. |
| 5,315,859 A | 5/1994 | Schommer |
| 5,349,949 A | 9/1994 | Schegerin |
| 5,366,805 A | 11/1994 | Fujiki et al. |
| D354,128 S | 1/1995 | Rinehart |
| D355,484 S | 2/1995 | Rinehart |
| 5,400,776 A | 3/1995 | Bartholomew |
| 5,429,683 A | 7/1995 | Le Mitouard |
| 5,438,979 A | 8/1995 | Johnson et al. |
| 5,441,046 A | 8/1995 | Starr et al. |
| 5,449,206 A | 9/1995 | Lockwood |
| 5,449,234 A | 9/1995 | Gipp et al. |
| 5,458,202 A | 10/1995 | Fellows et al. |
| 5,460,174 A | 10/1995 | Chang |
| 5,477,852 A | 12/1995 | Landis et al. |
| 5,513,634 A | 5/1996 | Jackson |
| 5,533,506 A | 7/1996 | Wood |
| 5,542,128 A | 8/1996 | Lomas |
| 5,551,419 A | 9/1996 | Froehlich et al. |
| 5,558,090 A | 9/1996 | James |
| 5,570,689 A | 11/1996 | Starr et al. |
| 5,588,423 A | 12/1996 | Smith |
| 5,595,174 A | 1/1997 | Gwaltney |
| 5,601,078 A | 2/1997 | Schaller et al. |
| D378,610 S | 5/1997 | Reischel et al. |
| 5,649,532 A | 7/1997 | Griffiths |
| 5,657,752 A | 8/1997 | Landis et al. |
| 5,662,101 A | 9/1997 | Ogden et al. |
| 5,664,566 A * | 9/1997 | McDonald ............ A62B 18/02 128/205.25 |
| 5,687,715 A | 11/1997 | Landis |
| 5,690,097 A | 11/1997 | Howard et al. |
| 5,724,965 A | 3/1998 | Handke et al. |
| 5,752,510 A | 5/1998 | Goldstein |
| 5,755,578 A | 5/1998 | Contant et al. |
| 5,806,727 A | 9/1998 | Joseph |
| 5,746,201 A | 12/1998 | Kidd |

(56) References Cited

U.S. PATENT DOCUMENTS

| | | | |
|---|---|---|---|
| 5,857,460 A | 1/1999 | Popitz | |
| 5,884,624 A | 3/1999 | Barnett et al. | |
| 5,904,278 A | 5/1999 | Barlow et al. | |
| 5,918,598 A | 7/1999 | Belfer | |
| 5,921,239 A | 7/1999 | McCall et al. | |
| 5,941,245 A | 8/1999 | Hannah et al. | |
| 5,943,473 A | 8/1999 | Levine | |
| 5,953,763 A | 9/1999 | Gouget | |
| 5,966,745 A | 10/1999 | Schwartz et al. | |
| 6,016,804 A | 1/2000 | Gleason et al. | |
| 6,017,315 A | 1/2000 | Starr et al. | |
| 6,019,101 A | 2/2000 | Cotner et al. | |
| 6,021,528 A * | 2/2000 | Jurga | A63B 71/12 2/326 |
| 6,039,044 A | 3/2000 | Sullivan | |
| 6,050,260 A | 4/2000 | Daniell et al. | |
| 6,112,746 A | 9/2000 | Kwok et al. | |
| 6,116,235 A | 9/2000 | Walters et al. | |
| 6,119,693 A | 9/2000 | Kwok et al. | |
| 6,119,694 A | 9/2000 | Correa et al. | |
| 6,135,109 A | 10/2000 | Blasdell et al. | |
| 6,135,432 A | 10/2000 | Hebblewhite et al. | |
| 6,192,886 B1 | 2/2001 | Rudolph | |
| D440,302 S | 4/2001 | Wolfe | |
| 6,272,933 B1 | 8/2001 | Gradon et al. | |
| 6,298,850 B1 | 10/2001 | Argraves | |
| 6,302,105 B1 | 10/2001 | Wickham et al. | |
| 6,341,606 B1 * | 1/2002 | Bordewick | A61M 16/06 128/206.12 |
| 6,347,631 B1 | 2/2002 | Hansen et al. | |
| D455,891 S | 4/2002 | Biedrzycki | |
| 6,398,197 B1 | 6/2002 | Dickinson et al. | |
| 6,412,487 B1 | 7/2002 | Gunaratnam et al. | |
| 6,412,488 B1 | 7/2002 | Barnett et al. | |
| 6,418,928 B1 | 7/2002 | Bordewick et al. | |
| 6,427,694 B1 | 8/2002 | Hecker et al. | |
| 6,431,172 B1 | 8/2002 | Bordewick | |
| 6,435,181 B1 | 8/2002 | Jones, Jr. et al. | |
| 6,439,234 B1 | 8/2002 | Curti et al. | |
| 6,457,473 B1 | 10/2002 | Brostrom et al. | |
| 6,467,483 B1 | 10/2002 | Kopacko et al. | |
| 6,470,886 B1 | 10/2002 | Jestrabek-Hart | |
| 6,478,026 B1 | 11/2002 | Wood | |
| 6,484,725 B1 | 11/2002 | Chi et al. | |
| 6,488,664 B1 | 12/2002 | Solomon et al. | |
| 6,491,034 B1 | 12/2002 | Gunaratnam et al. | |
| 6,513,526 B2 | 2/2003 | Kwok et al. | |
| 6,526,978 B2 | 3/2003 | Dominguez | |
| 6,530,373 B1 | 3/2003 | Patron et al. | |
| 6,561,188 B1 | 5/2003 | Ellis | |
| 6,561,190 B1 | 5/2003 | Kwok | |
| 6,561,191 B1 | 5/2003 | Kwok | |
| 6,581,594 B1 | 6/2003 | Drew et al. | |
| 6,581,601 B2 | 6/2003 | Ziaee | |
| 6,581,602 B2 | 6/2003 | Kwok et al. | |
| 6,584,977 B1 | 7/2003 | Serowski | |
| 6,588,424 B2 * | 7/2003 | Bardel | A62B 17/04 128/206.21 |
| 6,615,832 B1 | 9/2003 | Chen | |
| 6,629,531 B2 | 10/2003 | Gleason et al. | |
| 6,631,718 B1 | 10/2003 | Lovell | |
| 6,634,358 B2 | 10/2003 | Kwok et al. | |
| 6,637,434 B2 | 10/2003 | Noble | |
| 6,644,315 B2 | 11/2003 | Ziaee | |
| 6,651,658 B1 | 11/2003 | Hill | |
| 6,651,663 B2 | 11/2003 | Barnett et al. | |
| 6,659,102 B1 | 12/2003 | Sico | |
| 6,662,803 B2 | 12/2003 | Gradon et al. | |
| 6,668,828 B1 | 12/2003 | Figley et al. | |
| D485,905 S | 1/2004 | Moore | |
| 6,679,257 B1 | 1/2004 | Robertson et al. | |
| 6,679,265 B2 | 1/2004 | Strickland et al. | |
| 6,691,707 B1 | 2/2004 | Gunaratnam et al. | |
| 6,712,072 B1 | 3/2004 | Lang | |
| 6,736,139 B1 | 5/2004 | Wix | |
| 6,772,761 B1 | 8/2004 | Rucker, Jr. | |
| 6,796,308 B2 | 9/2004 | Gunaratnam et al. | |
| 6,817,362 B2 | 11/2004 | Gelinas et al. | |
| 6,823,869 B2 | 11/2004 | Raje et al. | |
| 6,851,425 B2 | 2/2005 | Jaffre et al. | |
| 6,883,177 B1 | 4/2005 | Ouellette et al. | |
| 6,892,729 B2 | 5/2005 | Smith et al. | |
| 6,895,965 B2 | 5/2005 | Scarberry et al. | |
| 6,907,882 B2 | 6/2005 | Ging et al. | |
| 6,918,390 B2 | 7/2005 | Lithgow et al. | |
| 6,951,218 B2 | 10/2005 | Gradon et al. | |
| 6,953,354 B2 | 10/2005 | Edirisuriya et al. | |
| 6,997,187 B2 | 2/2006 | Wood et al. | |
| 7,004,165 B1 | 2/2006 | Salcido | |
| 7,007,696 B2 | 3/2006 | Palkon et al. | |
| 7,021,311 B2 | 4/2006 | Gunaratnam et al. | |
| D520,140 S | 5/2006 | Chaggares | |
| 7,066,179 B2 | 6/2006 | Eaton et al. | |
| 7,077,126 B2 | 7/2006 | Kummar et al. | |
| D526,094 S | 8/2006 | Chen | |
| 7,096,864 B1 | 8/2006 | Mayer | |
| D533,269 S * | 12/2006 | McAuley | D24/110.6 |
| 7,178,525 B2 | 2/2007 | Matula, Jr. et al. | |
| 7,178,528 B2 | 2/2007 | Lau | |
| 7,201,169 B2 | 4/2007 | Wilkie et al. | |
| 7,207,333 B2 | 4/2007 | Tohara | |
| 7,210,481 B1 | 5/2007 | Lovell et al. | |
| 7,219,669 B1 | 5/2007 | Lovell et al. | |
| 7,225,811 B2 | 6/2007 | Ruiz et al. | |
| 7,255,106 B2 | 8/2007 | Gallem et al. | |
| 7,287,528 B2 | 10/2007 | Ho et al. | |
| 7,290,546 B2 | 11/2007 | Sprinkle et al. | |
| 7,318,437 B2 | 1/2008 | Gunaratnam et al. | |
| 7,353,827 B2 | 4/2008 | Geist | |
| 7,357,136 B2 | 4/2008 | Ho et al. | |
| 7,406,966 B2 | 8/2008 | Wondka et al. | |
| 7,448,386 B2 | 11/2008 | Ho et al. | |
| 7,487,772 B2 | 2/2009 | Ging et al. | |
| 7,493,902 B2 | 2/2009 | White et al. | |
| D589,139 S | 3/2009 | Guney | |
| 7,523,754 B2 | 4/2009 | Lithgow et al. | |
| D595,841 S | 7/2009 | McAuley et al. | |
| 7,562,658 B2 | 7/2009 | Madaus et al. | |
| 7,597,100 B2 | 10/2009 | Ging | |
| 7,640,934 B2 | 1/2010 | Zollinger et al. | |
| 7,658,189 B2 | 2/2010 | Davidson et al. | |
| 7,665,464 B2 | 2/2010 | Kopacko et al. | |
| D612,933 S | 3/2010 | Prentice | |
| 7,681,575 B2 | 3/2010 | Wixey et al. | |
| 7,694,677 B2 | 4/2010 | Tang | |
| 7,703,457 B2 | 4/2010 | Barnett et al. | |
| 7,753,051 B2 | 7/2010 | Burrow et al. | |
| D623,288 S | 9/2010 | Lubke | |
| 7,814,911 B2 | 10/2010 | Bordewick et al. | |
| 7,827,990 B1 | 11/2010 | Melidis et al. | |
| 7,856,982 B2 | 12/2010 | Matula et al. | |
| 7,877,817 B1 * | 2/2011 | Ho | A61M 16/06 128/207.11 |
| 7,896,003 B2 | 3/2011 | Matula et al. | |
| 7,931,024 B2 | 4/2011 | Ho et al. | |
| 7,934,501 B2 | 5/2011 | Fu | |
| 7,942,150 B2 | 5/2011 | Guney et al. | |
| 8,042,539 B2 | 10/2011 | Chandran et al. | |
| 8,042,541 B2 | 10/2011 | Amarasinghe et al. | |
| 8,109,271 B2 | 2/2012 | Vandine et al. | |
| 8,136,524 B2 | 3/2012 | Ging et al. | |
| 8,136,525 B2 | 3/2012 | Lubke et al. | |
| D661,796 S | 6/2012 | Andrews et al. | |
| 8,371,302 B2 | 2/2013 | Ging et al. | |
| 8,397,727 B2 | 3/2013 | Ng et al. | |
| 8,443,807 B2 | 5/2013 | McAuley et al. | |
| D686,313 S | 7/2013 | Matula et al. | |
| 8,479,726 B2 | 7/2013 | McAuley | |
| 8,479,741 B2 | 7/2013 | McAuley et al. | |
| 8,567,404 B2 | 10/2013 | Davidson et al. | |
| 8,631,793 B2 | 1/2014 | Omura et al. | |
| 8,631,799 B2 | 1/2014 | Davenport | |
| 8,636,005 B2 | 1/2014 | Gradon et al. | |
| 8,701,667 B1 | 4/2014 | Ho et al. | |

(56) References Cited

U.S. PATENT DOCUMENTS

| | | |
|---|---|---|
| 8,714,157 B2 | 5/2014 | McAuley et al. |
| 8,720,444 B2 | 5/2014 | Chang |
| 8,757,157 B2 | 6/2014 | Price et al. |
| 8,783,257 B2 | 7/2014 | McAuley et al. |
| 8,869,797 B2 | 10/2014 | Davidson et al. |
| 8,869,798 B2 | 10/2014 | Wells et al. |
| 8,875,709 B2 | 11/2014 | Davidson et al. |
| 8,944,061 B2 | 2/2015 | D'souza et al. |
| 8,950,404 B2 | 2/2015 | Formica et al. |
| 8,960,196 B2 | 2/2015 | Henry |
| 9,010,331 B2 | 4/2015 | Lang et al. |
| 9,027,556 B2 | 5/2015 | Ng et al. |
| 9,032,955 B2 | 5/2015 | Lubke et al. |
| 9,032,956 B2 | 5/2015 | Scheiner et al. |
| 9,072,852 B2 | 7/2015 | McAuley et al. |
| 9,119,929 B2 | 9/2015 | McAuley et al. |
| 9,119,931 B2 | 9/2015 | D'Souza et al. |
| 9,138,555 B2 | 9/2015 | McAuley et al. |
| 9,149,596 B2 | 10/2015 | Valcic et al. |
| 9,242,062 B2 | 1/2016 | Melidis et al. |
| 9,292,799 B2 | 3/2016 | McAuley et al. |
| 9,302,065 B2 | 4/2016 | Smith et al. |
| 9,320,566 B1 | 4/2016 | Alston, Jr. et al. |
| 9,320,866 B2 | 4/2016 | McAuley et al. |
| 9,333,315 B2 | 5/2016 | McAuley et al. |
| 9,339,622 B2 | 5/2016 | McAuley et al. |
| 9,339,624 B2 | 5/2016 | McAuley et al. |
| 9,375,545 B2 | 6/2016 | Darkin et al. |
| 9,381,316 B2 | 7/2016 | Ng et al. |
| 9,439,405 B2 | 9/2016 | Bruggemann et al. |
| 9,457,162 B2 | 10/2016 | Ging et al. |
| 9,486,601 B2 | 11/2016 | Stallard et al. |
| 9,517,317 B2 | 12/2016 | McAuley et al. |
| 9,522,246 B2 | 12/2016 | Frater et al. |
| 9,539,405 B2 | 1/2017 | McAuley et al. |
| 9,550,038 B2 | 1/2017 | McAuley et al. |
| 9,561,338 B2 | 2/2017 | McAuley et al. |
| 9,561,339 B2 | 2/2017 | McAuley et al. |
| 9,744,385 B2 | 8/2017 | Henry et al. |
| 9,884,160 B2 | 2/2018 | McAuley et al. |
| 9,907,925 B2 | 3/2018 | McAuley et al. |
| 10,080,856 B2 | 9/2018 | McLaren et al. |
| 10,252,015 B2 | 4/2019 | McAuley et al. |
| 2001/0017134 A1 | 8/2001 | Bahr |
| 2001/0020474 A1 | 9/2001 | Hecker et al. |
| 2001/0029952 A1* | 10/2001 | Curran .............. A62B 18/10 128/206.17 |
| 2002/0014241 A1 | 2/2002 | Gradon et al. |
| 2002/0020416 A1 | 2/2002 | Namey |
| 2002/0026934 A1 | 3/2002 | Lithgow et al. |
| 2002/0029780 A1 | 3/2002 | Frater et al. |
| 2002/0046755 A1 | 4/2002 | Voss |
| 2002/0053347 A1 | 5/2002 | Ziaee |
| 2002/0059935 A1 | 5/2002 | Wood |
| 2002/0096176 A1 | 7/2002 | Gunaratnam et al. |
| 2002/0096178 A1 | 7/2002 | Ziaee |
| 2002/0100474 A1 | 8/2002 | Kellner et al. |
| 2002/0100479 A1 | 8/2002 | Scarberry et al. |
| 2002/0108613 A1 | 8/2002 | Gunaratnam et al. |
| 2003/0005509 A1 | 1/2003 | Kelzer |
| 2003/0005931 A1 | 1/2003 | Jaffre et al. |
| 2003/0005933 A1 | 1/2003 | Izuchukwu |
| 2003/0019495 A1 | 1/2003 | Palkon et al. |
| 2003/0019496 A1 | 1/2003 | Kopacko et al. |
| 2003/0029454 A1 | 2/2003 | Gelinas et al. |
| 2003/0047185 A1 | 3/2003 | Olsen et al. |
| 2003/0075182 A1 | 4/2003 | Heidmann et al. |
| 2003/0079749 A1 | 5/2003 | Strickland et al. |
| 2003/0089373 A1 | 5/2003 | Gradon et al. |
| 2003/0094177 A1 | 5/2003 | Smith et al. |
| 2003/0121519 A1 | 7/2003 | Estes et al. |
| 2003/0149384 A1 | 8/2003 | Davis et al. |
| 2003/0164170 A1 | 9/2003 | Resmed |
| 2003/0172936 A1 | 9/2003 | Wilkie et al. |
| 2003/0196655 A1 | 10/2003 | Ging et al. |
| 2003/0196656 A1 | 10/2003 | Moore |
| 2003/0196658 A1 | 10/2003 | Ging et al. |
| 2003/0196659 A1 | 10/2003 | Gradon et al. |
| 2003/0196664 A1 | 10/2003 | Jacobson |
| 2003/0200970 A1 | 10/2003 | Stenzler et al. |
| 2003/0217746 A1 | 11/2003 | Gradon et al. |
| 2003/0221691 A1 | 12/2003 | Biener |
| 2004/0025882 A1 | 2/2004 | Madaus et al. |
| 2004/0035427 A1 | 2/2004 | Bordewick et al. |
| 2004/0065328 A1 | 4/2004 | Amarasinghe et al. |
| 2004/0067333 A1 | 4/2004 | Amarasinghe |
| 2004/0094157 A1 | 5/2004 | Danlanarayana et al. |
| 2004/0107968 A1 | 6/2004 | Griffiths |
| 2004/0112377 A1 | 6/2004 | Amarasinghe et al. |
| 2004/0112384 A1 | 6/2004 | Lithgow et al. |
| 2004/0112385 A1 | 6/2004 | Drew |
| 2004/0118406 A1 | 6/2004 | Lithgow et al. |
| 2004/0118412 A1 | 6/2004 | Piletti-Reyes |
| 2004/0139973 A1 | 7/2004 | Wright |
| 2004/0149280 A1 | 8/2004 | Semeniuk |
| 2004/0182398 A1 | 9/2004 | Sprinkle et al. |
| 2004/0211427 A1 | 10/2004 | Jones et al. |
| 2004/0221850 A1 | 11/2004 | Ging et al. |
| 2004/0226566 A1* | 11/2004 | Gunaratnam ..... A61M 16/0666 128/207.18 |
| 2004/0255949 A1 | 12/2004 | Lang et al. |
| 2005/0011521 A1 | 1/2005 | Sprinkle et al. |
| 2005/0011524 A1 | 1/2005 | Thomlinson et al. |
| 2005/0016532 A1 | 1/2005 | Farrell |
| 2005/0028822 A1* | 2/2005 | Sleeper ................ A61M 16/06 128/207.18 |
| 2005/0033247 A1 | 2/2005 | Thompson |
| 2005/0045182 A1 | 3/2005 | Wood et al. |
| 2005/0051177 A1 | 3/2005 | Wood |
| 2005/0066976 A1 | 3/2005 | Wondka |
| 2005/0076913 A1 | 4/2005 | Ho et al. |
| 2005/0092327 A1* | 5/2005 | Fini ...................... A61M 16/06 128/206.26 |
| 2005/0098183 A1 | 5/2005 | Nash et al. |
| 2005/0121037 A1 | 6/2005 | Wood |
| 2005/0133038 A1* | 6/2005 | Rutter ............... A61M 16/0497 128/207.17 |
| 2005/0150497 A1 | 7/2005 | Eifler et al. |
| 2005/0155604 A1 | 7/2005 | Ging et al. |
| 2005/0172969 A1 | 8/2005 | Ging |
| 2005/0199239 A1 | 9/2005 | Lang et al. |
| 2005/0199242 A1 | 9/2005 | Matula et al. |
| 2005/0205096 A1 | 9/2005 | Matula |
| 2005/0235999 A1 | 10/2005 | Wood et al. |
| 2005/0241644 A1 | 11/2005 | Guney et al. |
| 2006/0032504 A1 | 2/2006 | Burton et al. |
| 2006/0042629 A1 | 3/2006 | Geist |
| 2006/0042632 A1 | 3/2006 | Bishop et al. |
| 2006/0054169 A1 | 3/2006 | Han et al. |
| 2006/0060200 A1 | 3/2006 | Ho et al. |
| 2006/0076019 A1 | 4/2006 | Ho |
| 2006/0081256 A1 | 4/2006 | Palmer |
| 2006/0096598 A1 | 5/2006 | Ho et al. |
| 2006/0107958 A1 | 5/2006 | Sleeper |
| 2006/0118117 A1 | 6/2006 | Berthon-Jones et al. |
| 2006/0124131 A1 | 6/2006 | Chandran |
| 2006/0130844 A1 | 6/2006 | Ho et al. |
| 2006/0137690 A1 | 6/2006 | Gunaratnam et al. |
| 2006/0169286 A1 | 8/2006 | Eifler et al. |
| 2006/0174887 A1 | 8/2006 | Chandran et al. |
| 2006/0196511 A1 | 9/2006 | Lau et al. |
| 2006/0201514 A1 | 9/2006 | Jones et al. |
| 2006/0225740 A1 | 10/2006 | Eaton et al. |
| 2006/0231103 A1 | 10/2006 | Matula et al. |
| 2006/0237017 A1* | 10/2006 | Davidson ............. A61M 16/06 128/205.25 |
| 2006/0237018 A1 | 10/2006 | McAuley et al. |
| 2006/0249159 A1 | 11/2006 | Ho |
| 2006/0254593 A1 | 11/2006 | Chang |
| 2006/0266361 A1 | 11/2006 | Hernandez |
| 2006/0283459 A1 | 12/2006 | Geiselhart et al. |
| 2006/0283461 A1 | 12/2006 | Lubke et al. |
| 2007/0000492 A1 | 1/2007 | Hansel et al. |
| 2007/0010786 A1 | 1/2007 | Casey et al. |

(56) References Cited

U.S. PATENT DOCUMENTS

| | | |
|---|---|---|
| 2007/0044804 A1 | 3/2007 | Matula et al. |
| 2007/0062536 A1 | 3/2007 | McAuley |
| 2007/0089749 A1* | 4/2007 | Ho .................. A61M 16/0666 128/207.18 |
| 2007/0107733 A1 | 5/2007 | Ho |
| 2007/0125384 A1 | 6/2007 | Zollinger et al. |
| 2007/0125385 A1 | 6/2007 | Ho et al. |
| 2007/0125387 A1 | 6/2007 | Zollinger et al. |
| 2007/0137653 A1 | 6/2007 | Wood |
| 2007/0142785 A1 | 6/2007 | Lundgaard et al. |
| 2007/0157353 A1 | 7/2007 | Guney et al. |
| 2007/0163600 A1 | 7/2007 | Hoffman |
| 2007/0174952 A1* | 8/2007 | Jacob .................. B63C 11/12 2/426 |
| 2007/0175480 A1* | 8/2007 | Gradon ............. A61M 16/0638 128/207.11 |
| 2007/0209663 A1 | 9/2007 | Marque et al. |
| 2007/0215161 A1 | 9/2007 | Frater et al. |
| 2007/0221227 A1 | 9/2007 | Ho |
| 2007/0227541 A1 | 10/2007 | Van Den |
| 2007/0267017 A1 | 11/2007 | McAuley et al. |
| 2007/0295335 A1 | 12/2007 | Nashed |
| 2008/0035152 A1 | 2/2008 | Ho et al. |
| 2008/0041388 A1 | 2/2008 | McAuley et al. |
| 2008/0041393 A1 | 2/2008 | Bracken |
| 2008/0047560 A1* | 2/2008 | Veliss .................. A61M 16/06 128/206.24 |
| 2008/0060648 A1 | 3/2008 | Thornton et al. |
| 2008/0060653 A1 | 3/2008 | Hallett et al. |
| 2008/0060657 A1* | 3/2008 | McAuley .......... A61M 16/0666 128/207.18 |
| 2008/0083412 A1 | 4/2008 | Henry et al. |
| 2008/0099024 A1 | 5/2008 | Gunaratnam et al. |
| 2008/0105257 A1 | 5/2008 | Klasek et al. |
| 2008/0110464 A1 | 5/2008 | Davidson et al. |
| 2008/0142019 A1 | 6/2008 | Lewis |
| 2008/0171737 A1* | 7/2008 | Fensome .............. C07D 279/02 514/218 |
| 2008/0178875 A1 | 7/2008 | Henry |
| 2008/0178886 A1 | 7/2008 | Lieberman et al. |
| 2008/0190432 A1 | 8/2008 | Blochlinger et al. |
| 2008/0190436 A1 | 8/2008 | Jaffe et al. |
| 2008/0196728 A1 | 8/2008 | Ho |
| 2008/0210241 A1 | 9/2008 | Schulz et al. |
| 2008/0223370 A1* | 9/2008 | Kim .................. A41D 13/11 128/206.17 |
| 2008/0236586 A1* | 10/2008 | McDonald .......... A62B 18/084 128/205.24 |
| 2008/0257354 A1 | 10/2008 | Davidson |
| 2008/0264422 A1 | 10/2008 | Fishman |
| 2008/0276937 A1 | 11/2008 | Davidson et al. |
| 2008/0302366 A1 | 12/2008 | McGinnis et al. |
| 2008/0314388 A1 | 12/2008 | Brambilla et al. |
| 2008/0319334 A1 | 12/2008 | Yamamori |
| 2009/0014007 A1* | 1/2009 | Brambilla ............. A61M 16/06 128/206.24 |
| 2009/0032024 A1 | 2/2009 | Burz et al. |
| 2009/0044808 A1 | 2/2009 | Guney et al. |
| 2009/0078267 A1 | 3/2009 | Burz et al. |
| 2009/0107504 A1* | 4/2009 | McAuley ............. A61M 16/06 128/205.25 |
| 2009/0114227 A1 | 5/2009 | Gunaratnam et al. |
| 2009/0120442 A1 | 5/2009 | Ho |
| 2009/0126739 A1 | 5/2009 | Ng et al. |
| 2009/0133697 A1 | 5/2009 | Kwok et al. |
| 2009/0139527 A1 | 6/2009 | Ng et al. |
| 2009/0145429 A1 | 6/2009 | Ging et al. |
| 2009/0151729 A1 | 6/2009 | Judson et al. |
| 2009/0173349 A1 | 7/2009 | Hernandez et al. |
| 2009/0183739 A1 | 7/2009 | Wondka |
| 2009/0223519 A1 | 9/2009 | Eifler et al. |
| 2010/0000538 A1 | 1/2010 | Edwards et al. |
| 2010/0000539 A1 | 1/2010 | Woodard |
| 2010/0051031 A1 | 3/2010 | Lustenberger et al. |
| 2010/0083961 A1 | 4/2010 | McAuley et al. |
| 2010/0108072 A1 | 5/2010 | D'souza et al. |
| 2010/0132717 A1 | 6/2010 | Davidson et al. |
| 2010/0154798 A1 | 6/2010 | Henry et al. |
| 2010/0170516 A1* | 7/2010 | Grane .................. A61M 16/06 128/206.26 |
| 2010/0199992 A1 | 8/2010 | Ho |
| 2010/0229868 A1 | 9/2010 | Rummery et al. |
| 2010/0258132 A1 | 10/2010 | Moore |
| 2010/0258136 A1 | 10/2010 | Doherty et al. |
| 2010/0294281 A1 | 11/2010 | Ho |
| 2010/0307502 A1 | 12/2010 | Rummery et al. |
| 2010/0313891 A1 | 12/2010 | Veliss et al. |
| 2010/0319700 A1 | 12/2010 | Ng et al. |
| 2010/0326445 A1 | 12/2010 | Veliss et al. |
| 2011/0072553 A1 | 3/2011 | Ho |
| 2011/0088699 A1 | 4/2011 | Skipper |
| 2011/0146685 A1 | 6/2011 | Allan et al. |
| 2011/0232649 A1 | 9/2011 | Collazo et al. |
| 2011/0265796 A1 | 11/2011 | Amarasinghe et al. |
| 2011/0290253 A1 | 12/2011 | McAuley |
| 2011/0308520 A1 | 12/2011 | McAuley et al. |
| 2012/0125339 A1 | 5/2012 | Ho et al. |
| 2012/0132208 A1 | 5/2012 | Judson et al. |
| 2012/0132209 A1 | 5/2012 | Rummery |
| 2012/0138061 A1 | 6/2012 | Dravitzki et al. |
| 2012/0204879 A1 | 8/2012 | Cariola et al. |
| 2012/0285457 A1 | 11/2012 | Mansour et al. |
| 2012/0304999 A1 | 12/2012 | Swift et al. |
| 2012/0318270 A1 | 12/2012 | McAuley et al. |
| 2013/0133659 A1 | 5/2013 | Ng et al. |
| 2013/0133664 A1 | 5/2013 | Startare |
| 2013/0152918 A1 | 6/2013 | Rummery et al. |
| 2013/0160769 A1 | 6/2013 | Ng et al. |
| 2014/0026888 A1 | 1/2014 | Matula |
| 2014/0083428 A1 | 3/2014 | Rothermel et al. |
| 2014/0083430 A1 | 3/2014 | Matula, Jr. et al. |
| 2014/0137870 A1 | 5/2014 | Barlow et al. |
| 2014/0311492 A1 | 10/2014 | Stuebiger et al. |
| 2014/0338672 A1 | 11/2014 | D'Souza et al. |
| 2015/0013678 A1 | 1/2015 | McAuley |
| 2015/0033457 A1 | 2/2015 | Tryner et al. |
| 2015/0090266 A1 | 4/2015 | Melidis et al. |
| 2015/0297855 A1 | 10/2015 | McAuley et al. |
| 2015/0335846 A1 | 11/2015 | Romagnoli et al. |
| 2015/0352308 A1 | 12/2015 | Cullen et al. |
| 2015/0374944 A1 | 12/2015 | Edwards et al. |
| 2015/0374946 A1 | 12/2015 | McAuley et al. |
| 2016/0001028 A1 | 1/2016 | McAuley et al. |
| 2016/0008558 A1 | 1/2016 | Huddart et al. |
| 2016/0038705 A1 | 2/2016 | McAuley et al. |
| 2016/0038706 A1 | 2/2016 | McAuley et al. |
| 2016/0038707 A1 | 2/2016 | Allan et al. |
| 2016/0051786 A1 | 2/2016 | McAuley et al. |
| 2016/0106944 A1 | 4/2016 | McAuley et al. |
| 2016/0213873 A1 | 7/2016 | McAuley et al. |
| 2016/0213874 A1 | 7/2016 | Davidson et al. |
| 2016/0296720 A1 | 10/2016 | Henry et al. |
| 2017/0028148 A1 | 2/2017 | McAuley et al. |
| 2017/0072155 A1 | 3/2017 | Allan et al. |
| 2017/0119988 A1 | 5/2017 | Allan et al. |
| 2017/0143925 A1 | 5/2017 | McAuley et al. |
| 2017/0239438 A1 | 8/2017 | McAuley et al. |
| 2017/0304574 A1 | 10/2017 | McAuley et al. |
| 2017/0326324 A1 | 11/2017 | McAuley et al. |
| 2017/0326325 A1 | 11/2017 | Allan et al. |
| 2018/0221613 A1 | 8/2018 | McAuley et al. |
| 2019/0030273 A1 | 1/2019 | McAuley et al. |

FOREIGN PATENT DOCUMENTS

| | | |
|---|---|---|
| CD | 000966064-0001 | 9/2008 |
| CD | 000966064-0002 | 9/2008 |
| CD | 000966064-0003 | 9/2008 |
| CD | 000966064-0004 | 9/2008 |
| CD | 000966064-0017 | 9/2008 |
| CN | 217 253 8 | 7/1994 |
| CN | 1784250 | 6/2006 |
| CN | 1901961 A | 1/2007 |

(56) References Cited

FOREIGN PATENT DOCUMENTS

| | | |
|---|---|---|
| CN | 1988930 A | 6/2007 |
| CN | 101115521 | 1/2008 |
| CN | 101214402 | 7/2008 |
| CN | 101516300 | 8/2009 |
| CN | 101541380 | 9/2009 |
| DE | 895682 C | 11/1953 |
| DE | 29723101 U1 | 7/1998 |
| DE | 19603949 | 11/1998 |
| DE | 10312881 B3 | 5/2004 |
| DE | 102006011151 A1 | 9/2007 |
| EP | 0 350 322 | 1/1990 |
| EP | 0 427 474 | 5/1991 |
| EP | 0 462 701 | 12/1991 |
| EP | 0747078 | 12/1996 |
| EP | 1 099 452 | 5/2001 |
| EP | 0 830 180 | 3/2002 |
| EP | 1 258 266 | 11/2002 |
| EP | 1 582 231 | 10/2005 |
| EP | 2 042 209 | 4/2009 |
| EP | 1488820 B1 | 9/2009 |
| EP | 2 130 563 A1 | 12/2009 |
| EP | 2 145 645 | 1/2010 |
| EP | 1 753 495 | 9/2010 |
| EP | 1 481 702 | 9/2012 |
| EP | 2 658 725 | 11/2013 |
| EP | 2 749 176 | 7/2014 |
| EP | 1646910 | 8/2015 |
| EP | 2 022 528 | 3/2016 |
| FR | 2658725 | 8/1991 |
| FR | 2749176 | 12/1997 |
| GB | 190 224 431 | 12/1902 |
| GB | 880 824 | 10/1961 |
| GB | 979357 | 1/1965 |
| GB | 1 467 828 | 3/1977 |
| GB | 2133275 A | 7/1984 |
| GB | 2186801 | 8/1987 |
| GB | 2173274 | 12/1997 |
| JP | H09-010311 | 1/1997 |
| JP | 2000-325481 | 11/2000 |
| JP | 2004-016488 | 1/2004 |
| JP | 2005-529687 | 10/2005 |
| JP | 2005-537906 | 12/2005 |
| JP | 2007-516750 | 6/2007 |
| JP | 2007-527271 | 9/2007 |
| NZ | 531332 | 2/2004 |
| NZ | 534606 | 8/2004 |
| NZ | 528029 | 3/2005 |
| NZ | 548575 | 7/2006 |
| NZ | 551103 | 11/2006 |
| WO | WO 82/003548 | 10/1982 |
| WO | WO 97/32494 | 9/1997 |
| WO | WO 1998/04310 | 2/1998 |
| WO | WO 1998/04311 | 2/1998 |
| WO | WO 98/18514 | 5/1998 |
| WO | WO 1998/018514 | 5/1998 |
| WO | WO 98/024499 | 6/1998 |
| WO | WO 98/048878 | 11/1998 |
| WO | WO 1998/57691 | 12/1998 |
| WO | WO 1999/04842 | 2/1999 |
| WO | WO 99/43375 | 9/1999 |
| WO | WO 99/58181 | 11/1999 |
| WO | WO 99/058198 | 11/1999 |
| WO | WO 1999/058181 | 11/1999 |
| WO | WO 00/050122 | 8/2000 |
| WO | WO 00/57942 | 10/2000 |
| WO | WO 2000/057942 | 10/2000 |
| WO | WO 00/69497 | 11/2000 |
| WO | WO 2000/069497 | 11/2000 |
| WO | WO 00/74758 | 12/2000 |
| WO | WO 00/78384 | 12/2000 |
| WO | WO 2000/074758 | 12/2000 |
| WO | WO 2000/078384 | 12/2000 |
| WO | WO 2001/000266 | 1/2001 |
| WO | WO 01/32250 | 5/2001 |
| WO | WO 01/41854 | 6/2001 |
| WO | WO 2001/041854 | 6/2001 |
| WO | WO 01/058293 | 8/2001 |
| WO | WO 01/62326 | 8/2001 |
| WO | WO 2001/062326 | 8/2001 |
| WO | WO 01/097892 | 12/2001 |
| WO | WO 01/097893 | 12/2001 |
| WO | WO 2001/097892 | 12/2001 |
| WO | WO 02/005883 | 1/2002 |
| WO | WO 02/011804 | 2/2002 |
| WO | WO 02/047749 | 6/2002 |
| WO | WO 2002/074372 | 9/2002 |
| WO | WO 03/035156 | 5/2003 |
| WO | WO 03/092755 | 11/2003 |
| WO | WO 2004/007010 | 1/2004 |
| WO | WO 2004/022147 | 3/2004 |
| WO | WO 04/030736 | 4/2004 |
| WO | WO 2004/041341 | 5/2004 |
| WO | WO 2004/041342 | 5/2004 |
| WO | WO 04/073777 | 9/2004 |
| WO | WO 2004/073778 | 9/2004 |
| WO | WO 05/010608 | 2/2005 |
| WO | WO 05/016403 | 2/2005 |
| WO | WO 05/018523 | 3/2005 |
| WO | WO 2005/021075 | 3/2005 |
| WO | WO 2005/051468 | 6/2005 |
| WO | WO 04/096332 | 7/2005 |
| WO | WO 05/063326 | 7/2005 |
| WO | WO 05/063328 | 7/2005 |
| WO | WO 2005/079726 | 9/2005 |
| WO | WO 2005/086946 | 9/2005 |
| WO | WO 05/097247 | 10/2005 |
| WO | WO 05/123166 | 12/2005 |
| WO | WO 06/000046 | 1/2006 |
| WO | WO 06/050559 | 5/2006 |
| WO | WO 06/074513 | 7/2006 |
| WO | WO 06/074514 | 7/2006 |
| WO | WO 06/074515 | 7/2006 |
| WO | WO 2006/069415 | 7/2006 |
| WO | WO 2006/096924 | 9/2006 |
| WO | WO 06/130903 | 12/2006 |
| WO | WO 06/138346 | 12/2006 |
| WO | WO 06/138416 | 12/2006 |
| WO | WO 07/006089 | 1/2007 |
| WO | WO 07/009182 | 1/2007 |
| WO | WO 07/021777 | 2/2007 |
| WO | WO 2007/022562 | 3/2007 |
| WO | WO 2007/041751 | 4/2007 |
| WO | WO 2007/041786 | 4/2007 |
| WO | WO 2007/045008 | 4/2007 |
| WO | WO 07/048174 | 5/2007 |
| WO | WO 07/053878 | 5/2007 |
| WO | WO 2007/147088 | 12/2007 |
| WO | WO 2008/007985 | 1/2008 |
| WO | WO 08/014543 | 2/2008 |
| WO | WO 2008/030831 | 3/2008 |
| WO | WO 2008/060295 | 5/2008 |
| WO | WO 08/068966 | 6/2008 |
| WO | WO 2008/070929 | 6/2008 |
| WO | WO 2008/106716 | 9/2008 |
| WO | WO 2008/148086 | 12/2008 |
| WO | WO 09/026627 | 3/2009 |
| WO | WO 2009/052560 | 4/2009 |
| WO | WO 2009/059353 | 5/2009 |
| WO | WO 2009/092057 | 7/2009 |
| WO | WO 2009/139647 | 11/2009 |
| WO | WO 10/066004 | 6/2010 |
| WO | WO 10/131189 | 11/2010 |
| WO | WO 10/135785 | 12/2010 |
| WO | WO 2011/014931 | 2/2011 |
| WO | WO 11/059346 | 5/2011 |
| WO | WO 11/060479 | 5/2011 |
| WO | WO 12/045127 | 4/2012 |
| WO | WO 2012/052902 | 4/2012 |
| WO | WO 12/143822 | 10/2012 |
| WO | WO 14/020469 | 2/2014 |
| WO | WO 14/175752 | 10/2014 |
| WO | WO 14/175753 | 10/2014 |
| WO | WO 2015/033287 | 3/2015 |

(56) References Cited

FOREIGN PATENT DOCUMENTS

| WO | WO 16/000040 | 1/2016 |
|---|---|---|
| WO | WO 2017/049356 | 3/2017 |
| WO | WO 2017/049357 | 3/2017 |

OTHER PUBLICATIONS

International Search Report, International Application No. PCT/NZ2009/000219, dated Feb. 2, 2010, 3 pages.
English Translation of Chinese Examination Report; Application No. 2007800266164; 5 pages.
English Translation of First Office Action for Chinese Application No. 201210080441.8 dated Mar. 24, 2014, in 4 pages.
Examination Report; Australian Application No. 2007273324; dated May 22, 2012; 3 pages.
International Search Report for International Application No. PCT/NZ2007/000185, dated Oct. 31, 2007, in 3 pages.
Second Chinese Office Action for Chinese Patent Application No. 201210080441.8 dated Dec. 1, 2014 in 11 pages (with English translation).
Australian Examination Report for Patent Application No. 2012265597 dated Dec. 19, 2013, in 5 pages.
Canadian Examination Report for Application No. 2655839 dated Oct. 4, 2013, in 2 pages.
English Translation of Chinese Examination Report; Chinese Application No. 2007800266164; 5 pages.
International Search Report; PCT/NZ2009/000072; dated Jul. 28, 2009; 3 pages.
UK Search and Examination Report; dated Mar. 14, 2013; Application No. GB1210075.6; 2 pages.
UK Examination Report; dated May 9, 2013; Application No. GB1119385.1; 4 pages.
Australian Examination Report; dated Mar. 4, 2014; Application No. 2010246985; 5 pages.
English Translation of JP Examination Report; dated Feb. 10, 2014; Application No. 2012-510418; 4 pages.
Chinese Examination Report; dated Mar. 27, 2014; Chinese Application No. 201080028029.0; 16 pages.
GB Combined Search and Examination Report; dated May 7, 2014; Application No. GB1406402.6; 6 pages.
GB Combined Search and Examination Report; dated May 7, 2014; Application No. GB1406401.8; 4 pages.
JP Examination Report, Application No. 2012-538784; 3 pages.
Australian Examination Report; dated Aug. 14, 2015; Application No. 2015202814; 8 pages.
Chinese Examination Report; dated Jul. 17, 2015; Application No. 201080061122.1; 10 pages.
Chinese Examination Report; dated Sep. 14, 2015; Application No. 201080028029.0; 3 pages.
European Extended Search Report; dated Sep. 4, 2015; Application No. 10830251.4; 7 pages.
European Extended Search Report; dated Sep. 8, 2015; Application No. 10774623.2; 7 pages.
Japanese Examination Report; dated Jul. 22, 2015; Application No. 2015-098324; 8 pages.
Japanese Examination Report; dated Aug. 5, 2015; Application No. 2012-538784; 8 pages.
Australian Examination Report; dated Jan. 9, 2015; Application No. 2010241390; 4 pages.
English Translation of Chinese Examination Report; dated Sep. 3, 2014; Application No. 201080061122.1; 9 pages.
Second Chinese Office Action; dated Jan. 19, 2015; Application No. 201080028029.0; 16 pages.
EPO Search Report; dated Apr. 2, 2014; Application No. 09819444.2; 8 pages.
Australian Examination Report; dated Jul. 20, 2015; Application No. 20015201920; 3 pages.
EP Office Action; dated Jul. 8, 2015; Application No. 07808683.2; 8 pages.
Canadian Examination Report of Application No. 2890556; dated Jan. 27, 2016; 3 pages.
International Search Report; PCT/NZ2010/000229; dated Mar. 18, 2011; 8 pages.
Written Opinion of the International Searching Authority; PCT/NZ2010/000229; dated Mar. 18, 2011; 13 pages.
International Preliminary Report on Patentability and Written Opinion of the ISA; International Application No. PCT/NZ2010/000229; dated May 22, 2012; 14 pages.
Third Office Action; Chinese Application No. 201080061122.1; dated Apr. 1, 2016; 5 pages.
Declaration of Dr. John Izuchukwu, Ph.D., P.E., U.S. Pat. No. 8,479,741, IPR Nos. 2016-1714 & 2016-1718.
Declaration of Dr. John Izuchukwu, Ph.D., P.E., U.S. Pat. No. 8,443,807, IPR Nos. 2016-1726 & 2016-1734.
File History of U.S. Pat. No. 8,443,807 to McAuley et al.
File History of U.S. Pat. No. 8,479,741 to McAuley et al.
Fisher & Paykel MR810 Manual, Rev. C, 2004.
Fisher & Paykel HC200 Series Nasal CPAP Blower & Heated Humidifier User Manual.
HomeDepot.com—Ring Nut Sales Page (Retrieved Oct. 16, 2015 from http://www.homedepot.com/p/Everbilt-1-2-in-Galvanized-HexNut-804076/204647893).
Malloy, Plastic Part Design for Injection Molding (1994).
Merriam-Webster's Collegiate Dictionary, Eleventh Edition (2004) (selected portions).
Patent Owner's Complaint for *Fisher & Paykel Healthcare Ltd. v. ResMed Corp.*, Case No. 3:16-cv-02068-GPC-WVG (S.D. Cal.).
Patent Owner's Complaint for *Fisher & Paykel Healthcare Ltd. v. ResMed Corp.*, Case No. 2:16-cv-06099-R-AJW (C.D. Cal.).
Patent Owner's Notice of Voluntary Dismissal Without Prejudice for *Fisher & Paykel Healthcare Ltd. v. ResMed Corp.*, Case No. 2:16-cv-06099-R-AJW (C.D. Cal.).
Petitioners' Complaint for *ResMed Inc., et al. v. Fisher & Paykel Healthcare Corp. Ltd., et al.*, Case No. 3:16-cv-02072-JAH-MDD (S.D. Cal.).
Petitioners' Notice of Voluntary Dismissal Without Prejudice for *ResMed Inc., et al. v. Fisher & Paykel Healthcare Corp. Ltd., et al.*, Case No. 3:16-cv-02072-JAH-MDD (S.D. Cal.).
Petition for Inter Partes Review of U.S. Pat. No. 8,479,741 Pursuant to 35 U.S.C. §§ 311-19, 37 C.F.R. § 42, IPR2016-01714.
Petition for Inter Partes Review of U.S. Pat. No. 8,479,741 Pursuant to 35 U.S.C. §§ 311-19, 37 C.F.R. § 42, IPR2016-01718.
Petition for Inter Partes Review of U.S. Pat. No. 8,443,807 Pursuant to 35 U.S.C. §§ 311-19, 37 C.F.R. § 42, IPR2016-01726.
Petition for Inter Partes Review of U.S. Pat. No. 8,443,807 Pursuant to 35 U.S.C. §§ 311-19, 37 C.F.R. § 42, IPR2016-01734.
ResMed Webpage from Jun. 29, 1997 (Source: Wayback Machine Internet Archive); http://web.archive.org/web/19970629053430/http://www.resmed.com/maskframes/mask.htm.
ResMed "Mirage Swift™ Nasal Pillows System from ResMed" publication, © 2004 ResMed Ltd.
ResMed "Mirage Swift™ Nasal Pillows System: User's Guide" publication, © 2004 ResMed Ltd.
ResMed "Mirage Vista™ Nasal Mask: Components Card" publication, © 2005 ResMed Ltd.
ResMed Origins Brochure (Retrieved Apr. 17, 2016 from http://www.resmed.com/us/dam/documents/articles/resmedorigins.pdf).
Statutory Declaration made by Alistair Edwin McAuley, Apr. 9, 2015, in the matter of an Opposition by Fisher & Paykel Healthcare Limited of Australian patent application 2009221630 in the name of ResMed Limited.
The American Heritage Dictionary of the English Language, Fourth Edition (2006) (selected portions).
WeddingBands.com—Men's Wedding Ring Shopping Page (Retrieved Oct. 16, 2015 from http://www.weddingbands.com/ProductPop_wedding_bands_metal/4 8214W.html).
Office Action in corresponding Australian Patent Application No. 2010241390, dated Sep. 28, 2016, in 4 pages.
Office Action in corresponding Australian Patent Application No. 2016204384, dated Aug. 5, 2016, in 2 pages.
Office Action in corresponding Canadian Patent Application No. 2,780,310, dated Jul. 26, 2016, in 4 pages.

(56) References Cited

OTHER PUBLICATIONS

Office Action in corresponding Japanese Patent Application No. 2012-538784, dated Jul. 25, 2016, in 2 pages.
Office Action in corresponding Canadian Patent Application No. 2918167, dated Oct. 3, 2016, in 4 pages.
Chinese Examination Report; dated Apr. 1, 2016; Application No. 201080061122.1; 5 pages.
European Extended Search Report; dated May 12, 2016; Application No. 09746823.5; 11 pages.
International Search Report for International Application No. PCT/NZ2014/000021; filed Feb. 21, 2014.
International Search Report; Application No. PCT/NZ2013/000138; dated Nov. 1, 2013; 5 pages.
Philips Respironics "System One Heated Humidifier-User Manual", 2011, pp. 1-16, [retrivied on Nov. 25, 2013] from the Internet: URL: http://www.cpapxchange.com/cpap-machines-biap-machines/system-one-60-series-cpap-humidifier-manual.pdf front cover, pp. 3-4 and 6.
International Search Report; PCT/NZ2005/000062; dated May 27, 2005;3 pages.
Office Action in corresponding Australian Patent Application No. 2016202799, dated May 31, 2016, in 2 pages.
Office Action in corresponding Australian Patent Application No. 2016202801, dated Jun. 20, 2016, in 2 pages.
EP Examination Report dated Apr. 3, 2017; Application No. 09746823.5; 4 pages.
U.S. Appl. No. 60/493,515, dated Aug. 8, 2002, Sleeper et al.
U.S. Appl. No. 60/496,059, dated Aug. 18, 2003, Ho et al.
U.S. Appl. No. 60/529,696, dated Dec. 16, 2003, Lithgow et al.
U.S. Appl. No. 61/064,406, dated Mar. 4, 2008, Wehbeh.
U.S. Appl. No. 61/071,893, dated May 22, 2008, Wehbeh et al.
U.S. Appl. No. 61/136,617, dated Sep. 19, 2008, Wehbeh et al.
Resmed Mirage Swift™II Nasal Pillows System prosuct page (http://www.resmed.com/en-us/products/masks/mirage swift II nasal pillows. system/Mirage-Swift-II-Nasal-Pillows-System.html?menu=products); archived Jul. 21, 2008, 2 pp.
Resmed Mirage Swift™II user brochure (http://www.resmed.com/en us/products/masks/mirage-swift _II _nasal _pillows _system/documents/mirage-swift-ii-np-brochure-patient-english-USA.pdf) copyright 2007, 4 pp.
ResMed Mirage Swift II Fitting guide (http://www:resmed.com/en-us/products/masks/mirage swift II nasal pillows system/documents/mirage-swift ii np-fitting English.pdf) copyright 2006, 2 pp,.
ResMed Mirage Swift II comparison to older Swift patient interface (http://vavw,resmed.com/en-us/products/masks/mirage _swift _II _nasal _pillows _system/documents/mirage-swift-ii-np-comparison-guide.pdf, 2007, 6 pp.
ResMed Mirage Swift II user guide (http://www.resmed.com/en-us/products/service _and _support/documents/60893r1_mirage_swiftll_nasal_userglide_us_multi.pdf) copyright 2006, 1 p.
ResMed Mirage Swift II component card (http://www.resmed.com/ed-us/products/maskd/mirage _swift _II _pillows _system/documents/mirage-swift- copyright 2006, 2 pp.
Resmed Swift LT Nasal Pillows System, product page, (http://www.resmed.com/en-us/products/masks/mirage _swift _II _nasal _pillows _system/Mirage-Swift-II-Nasal _Pillows-System.html?menu=products), Jul. 3, 2008, 2 pp.
Resmed Swift LT user brochure, (http://www.resmed.com/en-us/products/masks/mirage _swift _II _nasal _pillows _system/documents/mirage-swift-ii-np-brochure-patient-english-USA.pdf), copyright 2008, 4 pp.
Resmed Swift™LT component card (http://www.resmed.com/en-us/assets/documents/product/swift _lt/components _card/1012463_swift-It _components-card _USA _eng.pdf) copyright 2008, 46 pp,
Resmed Swift™LT fitting guide, (http://wvvw.resmed.com/en-us/assets/documents/product/swift-II/clinical_fact _sheet/1012406 swift-ii _fact-sheet _USA _eng.pdf), 2008, 2pp.
Resmed Swift™LT fact sheet (http://www.resmcd.com/en-us/assets/documents/product/swift-It/clinicalfact _sheet/1012406 swiftlt _fact-sheet _USA _eng.pdf, copyright 2008, 4 pp.

Resmed Swift™LT image gallery (http://www.resmed.com/en- us/products/masks/swift._lt_nasal_pillows_system/imagegallery.html?menu=products, Apr. 25, 2008, 2 pp.
Resmed Swift™LT interactive fitting guide—screenshot from troubleshooting part (http://www.resmed.com/enus/assets/multimedia/product/swifit-It/flash/swift-It-fitting-eng.swf), Jul. 3. 2008, 2 pp.
Puritan Bennett Breeze® SleepGear® CPAP Interface, product page (http://puritanbennett.com/prod/productaspx?id=233); archived Oct. 19, 2007, 2 pp.
Puritan Bennett Breeze® SleepGear® User's Guide (http://puritanbenneft.com/ _catalog/pdf/dfu/107598a00[1].pdf); copyright 2007, 18 pp.
Puritan Bennett Breeze® SleepGear® sales sheet (http://www.puritanbennett.coml _Catalog/PDF/Product/BreezeSleepGear.pdf) copyright 2016, 7 PP.
Puritan Bennett mask coding matrix (http://www.puritanbennett.com/ _Catalog/PDF/Product/BreezeSlpGear(ST03700).pdf) copyright 2006, 3 pp.
Puritan Bennett Breeze fitting guide (http://www.puritanbenneft.com/ _Catalog/PDF/Product/BreezeFiftingPoster.pdf, Oct. 19, 2007, 1 p.
Respironics Optilife Pillows mask product page (http://!optilife.respironics,com:80/); archived Nov. 21, 2007, 2 pp.
Respironics Optilife Pillows mask part Nos.product page (http://optilife.respironics.com:80/Parts.aspx); archived Nov. 23, 2007, 4 pp.
Respironics Optilife Pillows mask FAQ (http://optilife.respironics.com:80/fags.aspx); archived Nov. 23, 2007, 6 pp.
Respironics Optilife Pillows mask feature page (http://optilife.respironics.com:80/features.aspx); archived Nov. 23, 2007, 4 pp.
Respironics Optilife Pillows mask fitting guide screen shot (http://optilife.respironics.com:80/fittingGuide,aspx); archived Aug. 7, 2008, 1 p.
Respironics Optilife Pillows mask adjustment video screenshots, https://www.youtube.com/watch?v=shjcNmvvcBA); uploaded Aug. 3, 2008, 2 pp,.
Puritan Bennett Breeze description; copyright 2000 by Mallinckrodt Inc., 4 pp.
Fisher & Paykel opus product page, archived Sep. 3, 2009, 2 pp.
Fisher & Paykel Opus patient interface product photographs, Jul. 2007, 6 pp.
Photographs of Opus 360 nasal pillows mask patient nstructions RevB, Jul. 2007, 4 pp.
Respironics Optilife brochure detailing updates; copyright 2008; dated Mar. 26, 2008, 3 pp.
Fisher & Paykel Opus product page, archived Sep. 7, 2009, 2pp.
Fisher & Paykel Opus "Off-the-lips" pillows explanation page, archived Aug. 23, 2009, 2 pp.
Fisher & Paykel Opus "Off-the-lips" patient interface brochure, archived Oct. 14, 2009, 6 pp.
Fisher & Paykel Opus user-guide, archived Nov. 17, 2009, 2 pp.
Australian Examination Report No. 1, in patent application No. AU 2013300237, dated Jun. 8, 2017, in 4 pages.
Australian Examination Report in patent application No. 2016238904 dated May 4, 2018, 5 pages.
Australian examination report in patent application No. 2018202409, dated Jan. 21, 2019, 4 pages.
Australian examination report in patent application No, 2018201975, dated Mar. 30, 2019, 4 pages.
Canadian Examination Report in patent application No, 2780310, dated Jan. 25, 2018 4 pages.
Canadian Examination Report in patent application No. 2780310, dated Oct. 9, 2018, 3 pages.
Canadian Examination Report in patent application No. 2998247, dated Jan. 8, 2019, 4 pages.
Chinese Examination Report in patent application No. 201610114706.X, dated Jul. 30, 2018, 9 pp., with translation.
Chinese Examination Report dated Feb. 22, 2019 in patent application No. 201611251618.0.
European Examination Report in patent application No. 07808683.2, dated May 9, 2018, 3 pages.
European Examination Report, European Application 13828380.9, dated Apr. 7, 2017, 7 pp.

(56) References Cited

OTHER PUBLICATIONS

European Examination Report, European Application 13828380.9, dated Jul. 27, 2018, 8 pp.
European extended search report dated Jul. 23, 2018 in patent application No. 18163847.9, 7 pp.
European extended search report dated Sep. 21, 2018 in patent application No. 18178220.2, 7 pp.
European extended search report dated Oct. 31, 2018 in patent application No. 18171619.2, 9 pp.
European Extended Search Report dated Feb. 14, 2019 in patent application No. 18195537.8.
Great Britain Combined Search and Examination Report in patent application No. GB1719334.3, dated Nov. 30, 2017, in 9 pages.
Great Britain examination report dated May 30, 2018 in patent application No. GB17 9334,3, 4 pp.
Great Britain examination report dated Jul. 20. 2018 in patent application No. GB1719334.3, 3 pp,.
Great Britain combined search and examination report dated May 11, 2018 in patent application No. GB1805606.9, 7 pp.
Great Britain examination report dated Jul. 5, 2018 in patent application No. GB1805606.9, 3 pp.
Great Britain examination report dated May 11, 2018 in patent application No. GB1803255.7, 7 pp.
Great Britain examination report dated May 11, 2018 in patent application No. GB1805605.1, 7 pp.
Great Britain examination report in patent application No. GB1501499.6, dated Jun. 1, 2017, in 8 pages.
Great Britain Combined Search and Examination Report under Section 18(3), Application No. GB1501499.6, dated Oct. 12, 2017, in 4 pges.
Indian Examination Report received Mar. 14, 2019 in patent application No. 1431/KOLNO/2012.
Japanese examination report in patent application No. 2015-526496, dated Apr. 17, 2017, in 13 pages.
Statutory Declaration made by Alistair Edwin McAuley, Apr. 14, 2015, in the matter of an Opposition by Fisher & Paykel Healthcare Limited of Australian patent application 2009221630 in the name of ResMed Limited.
Statutory Declaration made by Alistair Edwin McAuley, Apr. 17, 2015, in the matter of an Opposition by Fisher & Paykel Healthcare Limited of Australian patent application 2009221630 in the name of ResMed Limited.
Statutory Declaration made by Alistair Edwin McAuley, Sep. 16, 2015, in the matter of an Opposition by Fisher & Paykel Healthcare Limited of Australian patent application 2009221630 in the name of ResMed Limited.
First Affidavit of Alistair Edwin McAuley, Dec. 5, 2016, in the matter of Fisher and Paykel Healthcare Limited v. ResMed Limited filed in the Federal Court of Australia.
Second Affidavit of Alistair Edwin McAuley, Dec, 21, 2016, in the matter of Fisher and Paykel Healthcare Limited v. ResMed Limited filed in the Federal Court of Australia.
Third Affidavit of Alistair Edwin McAuley, Jan 31, 2017, in the matter of Fisher and Paykel Healthcare Limited v. ResMed Limited filed in the Federal Court of Australia, 284 pp.
Declaration of Anthony Michael Ging in IPR 2019-000172, IPR 2019-000173, IPR 2019-000177, IPR 2019-000178, dated Nov. 8, 2018, 329 pp.
McGraw-Hill Dictionary of Scientific and Technical Terms, Sixth Edition, 2003, Tube, p. 2200.
Claim Chart for AirFit P10, U.S. Appl. No. 9333315. dated Nov. 7, 2018, 3 pp.
Fisher & Paykel Healthcare, FlexiFit®431 Full Face Mask instructions, 2010, 4 pp.
Fisher & Paykel Healthcare, FlexiFit™431 Full Face Mask, specification sheet, 2004, 2 pp.
Fisher & Paykel Healthcare, Interface Solutions Product Profile, 2006, 12 pp.
ResMed Exhibit FlexiFit™431, product brochure, web pages (Wayback Machine), 2006, 23 pp.
ResMed Ultra Mirage™Full Face Mask, product brochure, 2004, 2 pp.
ResMed Ultra Mirage™Full Face Mask, product brochure, web pages (Wayback Machine), 2006, 9 pp.
Australian Examination Report in patent application No. 2010241390, dated Jan. 9, 2015, 4 pages.
Australian examination report in patent application No. 2017200991, dated Oct. 13, 2017, 3 pages.
Australian examination report in patent application No. 2017201021, dated Apr. 7, 2017, 6 pages.
Canadian Examination Report in patent application No. 2890556, dated Nov. 28, 2016, 4 pages.
Chinese Office Action in patent application No. 201610116121.1, dated Sep. 28, 2017, 5 pages.
European Summons to Attend Oral Proceedings and Written Opinion dated Dec. 13, 2017 in patent application No. 09746823.5; 7 pages.
European Extended Search Report in patent application No. 17179765.7, dated Dec. 11, 2017.
European Search Report in patent application No. 11830981.4, dated Aug. 24, 2015, 6 pages.
Great Britain Combined Search and Examination Report in patent application No. GB1406402.6, dated May 7, 2014, 6 pages.
International Search Report for application No. PCT/NZ2005/000062 dated May 27, 2005.
International Search Report, PCT/NZ2011/000211, dated Feb. 17, 2012, 4 pages.
Written Opinion, PCT/NZ2011/000211, dated Feb. 17, 2012, 7 pages.
Written Opinion of the International Searching Authority, PCT/NZ2013/000139, dated Nov. 1 2013.
Indian Office Action in Patent Application No. 5250/KOLNP/2008, dated May 23, 2017, 8 pages.
Provisional Application, No. 61064406, 34 pages, copy provided by USPTO on Feb. 23, 2009.
Provisional Application, No. 61071893, 43 pages, copy provided by USPTO on Feb. 23, 2009.
Provisional Application, No. 61136617, 82 pages, copy provided by USPTO on Feb. 23, 2009.
Patent Owner Preliminary Response to Petition for Inter Partes Review of U.S. Appl. No. 8,479,741, IPR2016-01714, filed Dec. 14, 2016.
Decision Denying Institution of Inter Partes Review of U.S. Appl. No. 8,479,741 Pursuant to 37 C.F.R. § 42.108, IPR2016-01714, entered Mar. 10, 2017.
Patent Owner Preliminary Response to Petition for Inter Partes Review of U.S. Appl. No. 8,479,741, IPR2016-01718, filed Dec. 16, 2016.
Decision Denying Institution of Inter Partes Review of U.S. Appl. No. 8,479,741 Pursuant to 37 C.F.R. § 42.108, IPR2016-01718, entered Mar. 13, 2017.
Patent Owner Preliminary Response to Petition for Inter Partes Review of U.S. Appl. No. 8,443,807, IPR2016-01726, filed Dec. 13, 2016.
Decision Denying Institution of Inter Partes Review of U.S. Appl. No. 8,443,807 Pursuant to 37 C.F.R. § 42.108, IPR2016-01726, entered Mar. 6, 2017.
Patent Owner Preliminary Response to Petition for Inter Partes Review of U.S. Appl. No. 8,443,807, IPR2016-01734, filed Dec. 22, 2016.
Decision Denying Institution of Inter Partes Review of U.S. Appl. No. 8,443,807 Pursuant to 37 C.F.R. § 42.108, IPR2016-01734, entered Mar. 13, 2017.

\* cited by examiner

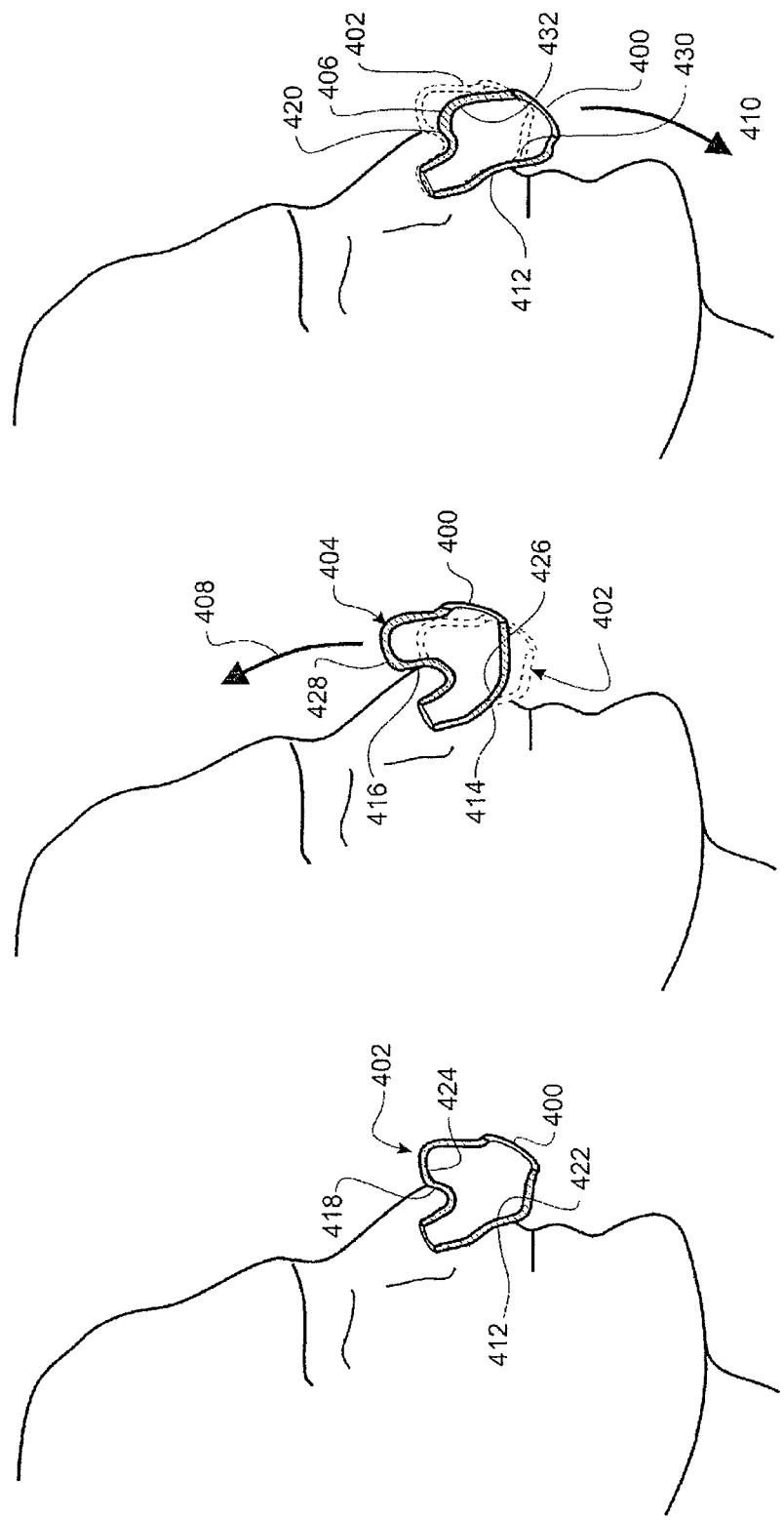

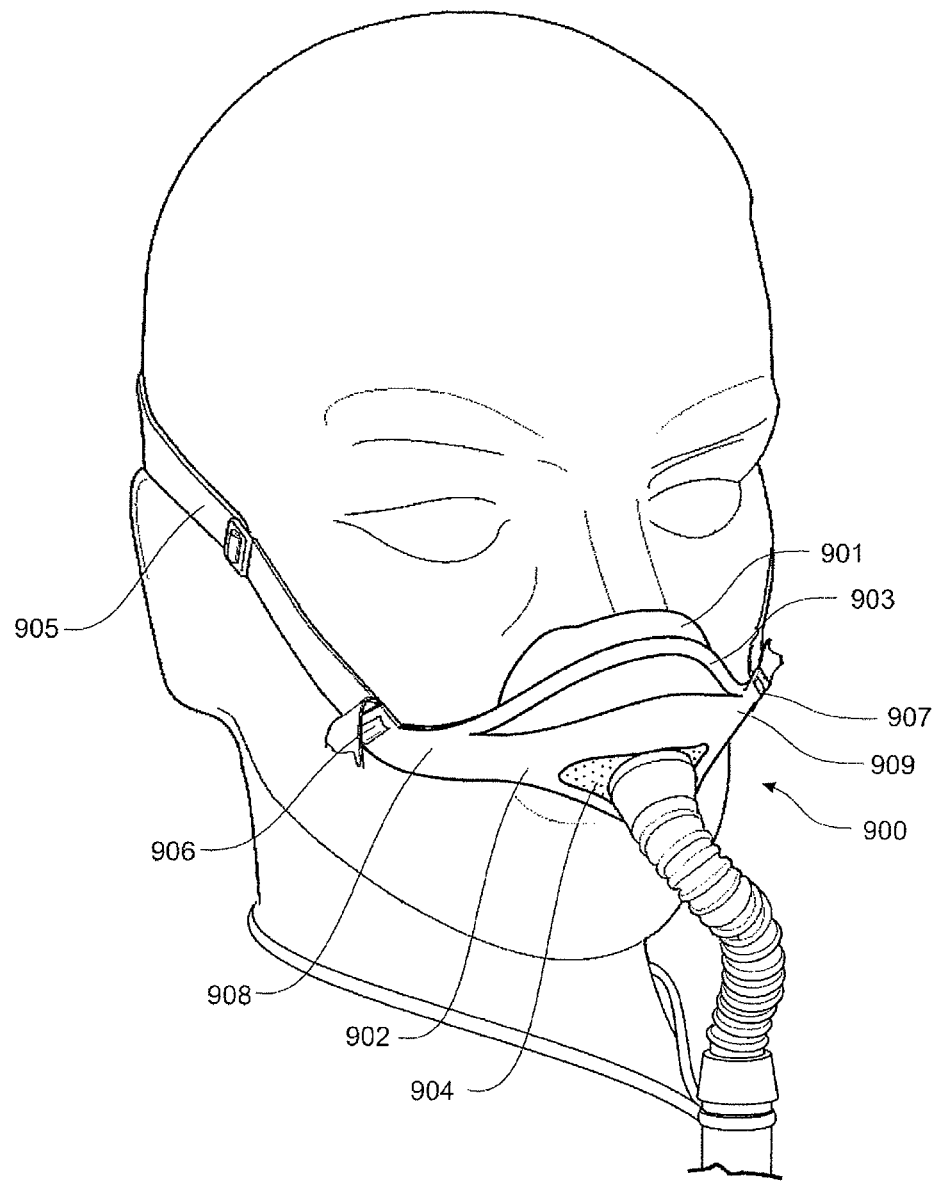
FIGURE 1т

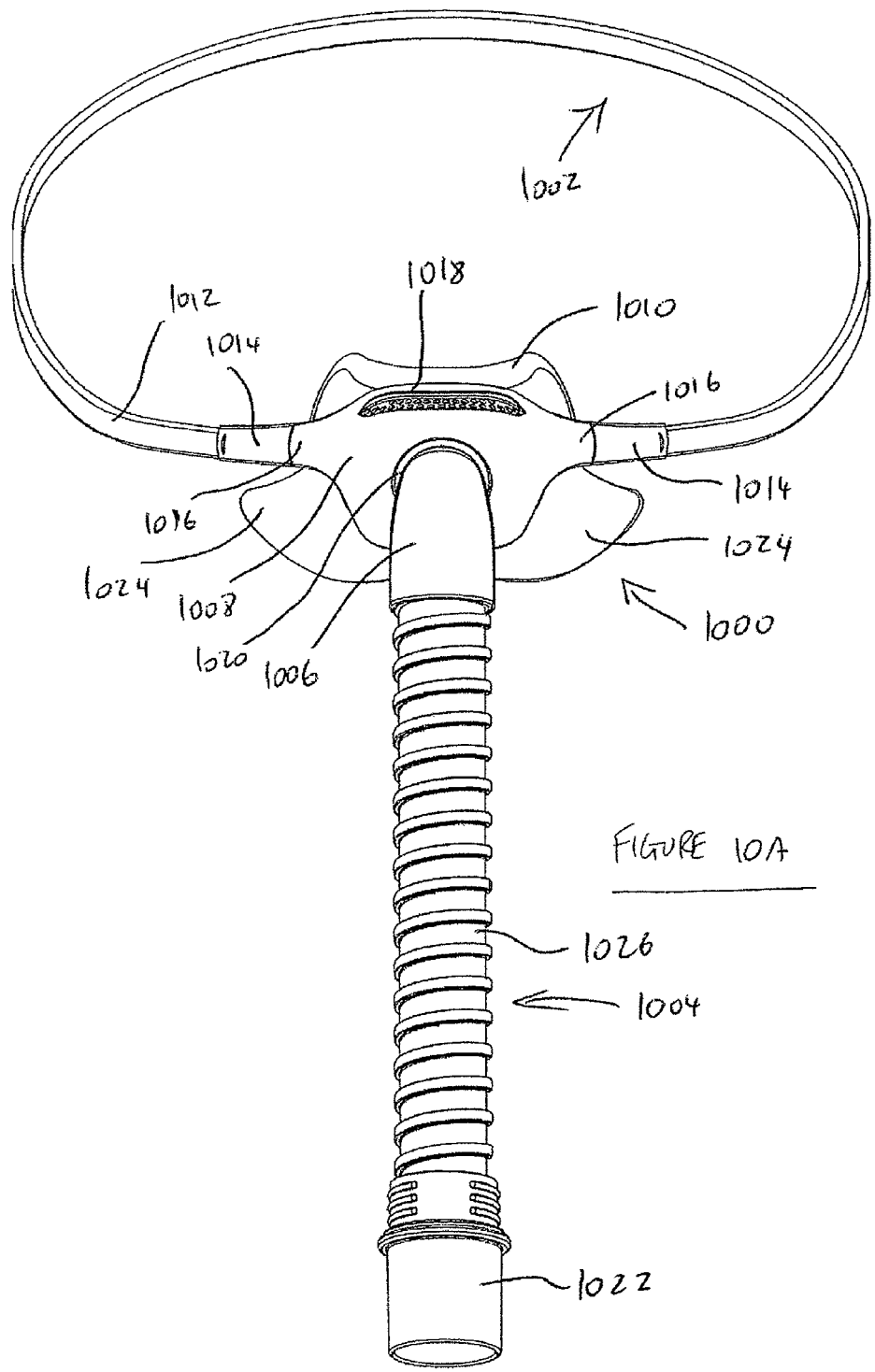

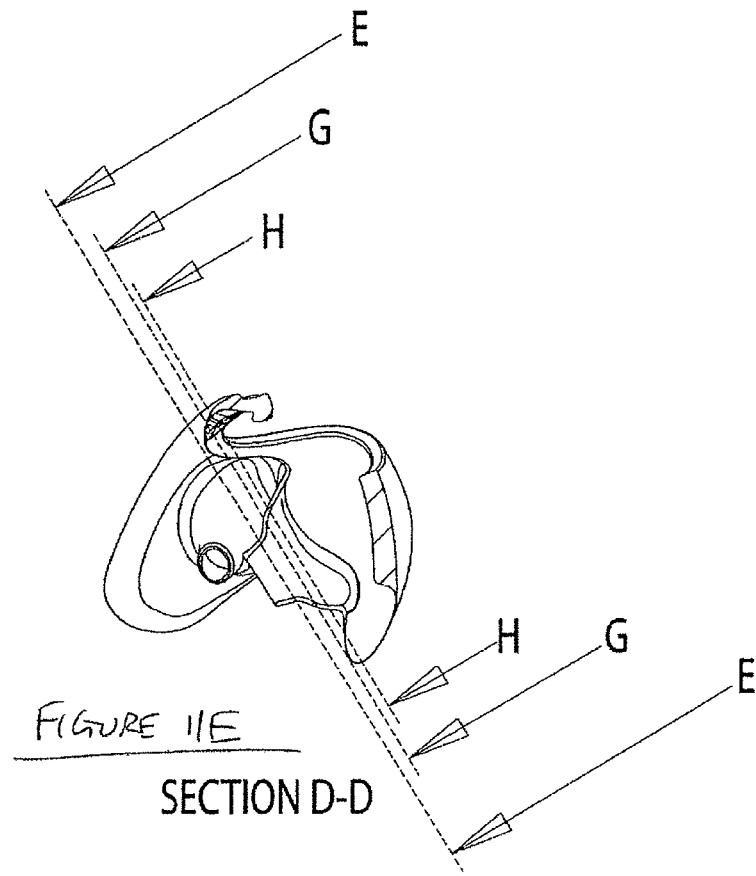
FIGURE 11E
SECTION D-D
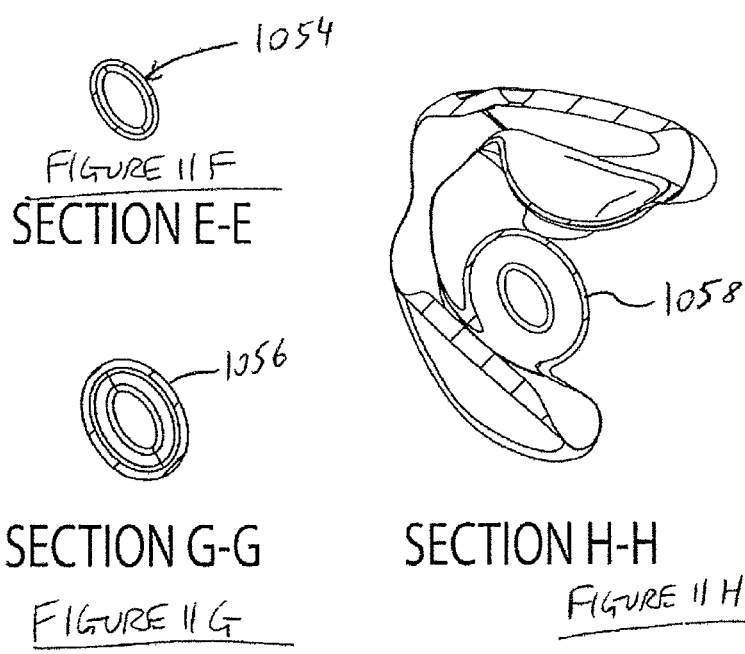
FIGURE 11F
SECTION E-E
SECTION G-G
FIGURE 11G
SECTION H-H
FIGURE 11H

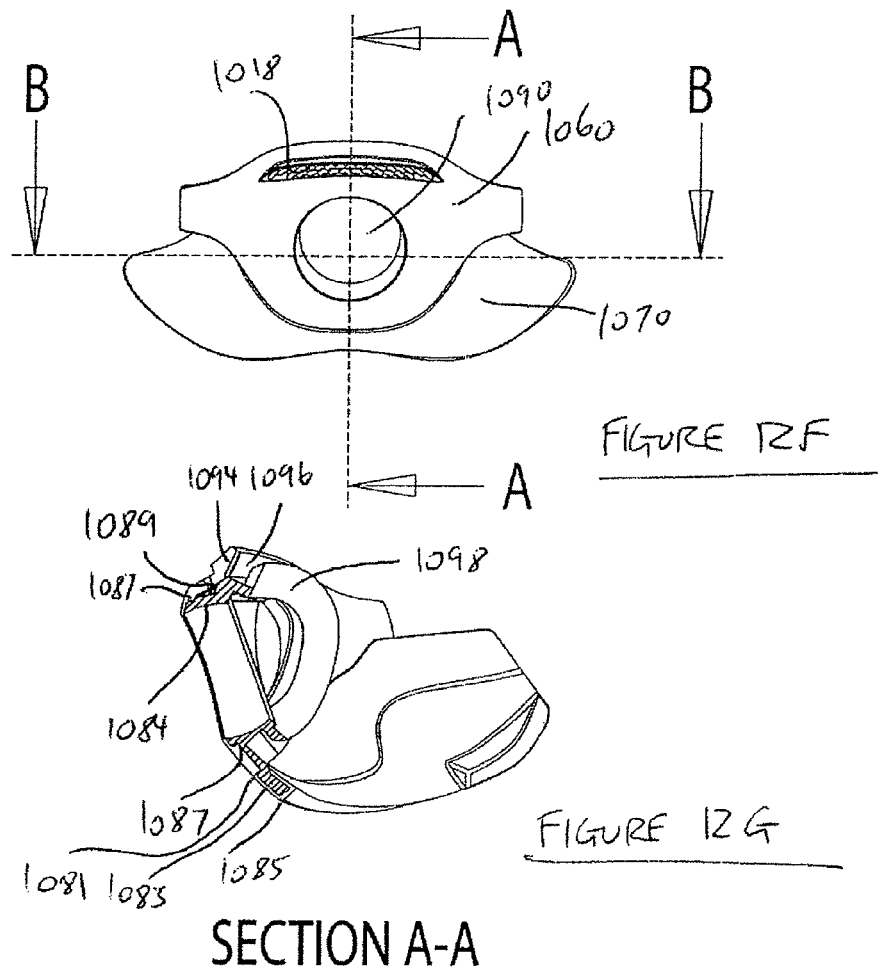
FIGURE 12F
SECTION A-A
FIGURE 12G
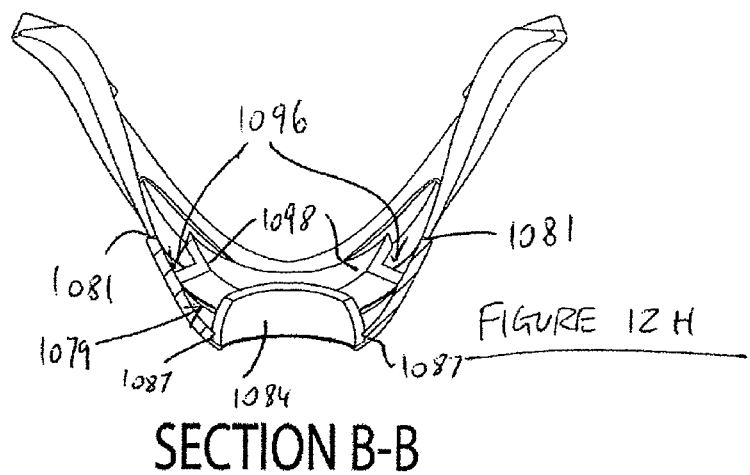
SECTION B-B
FIGURE 12H

FIG. 26
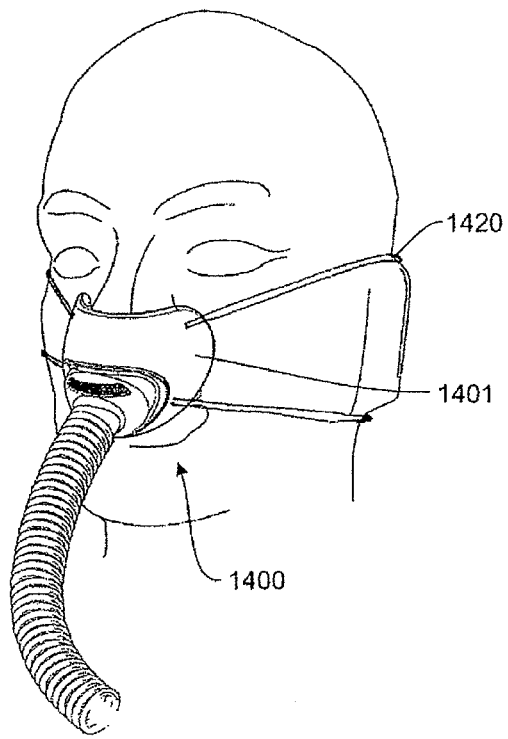
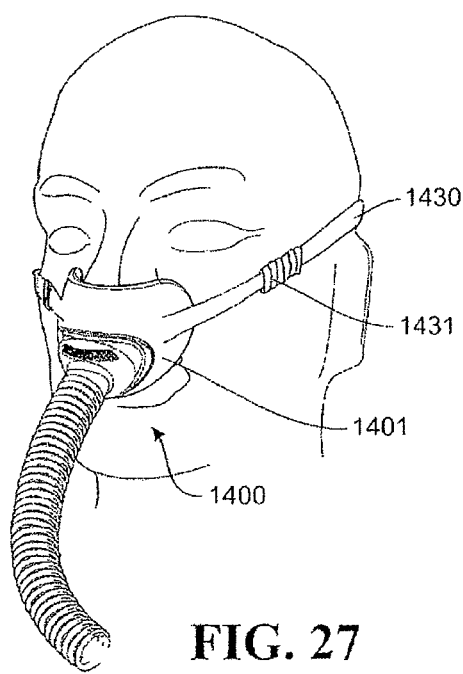
FIG. 27
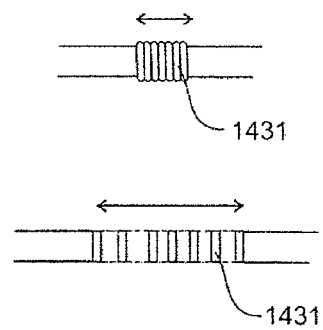
FIG. 27a

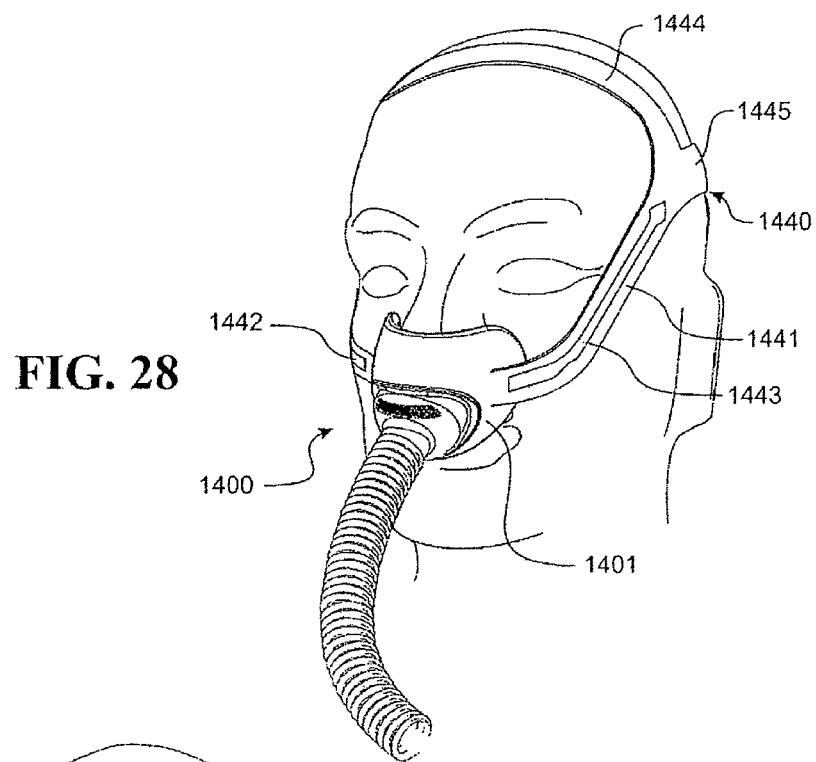
FIG. 28
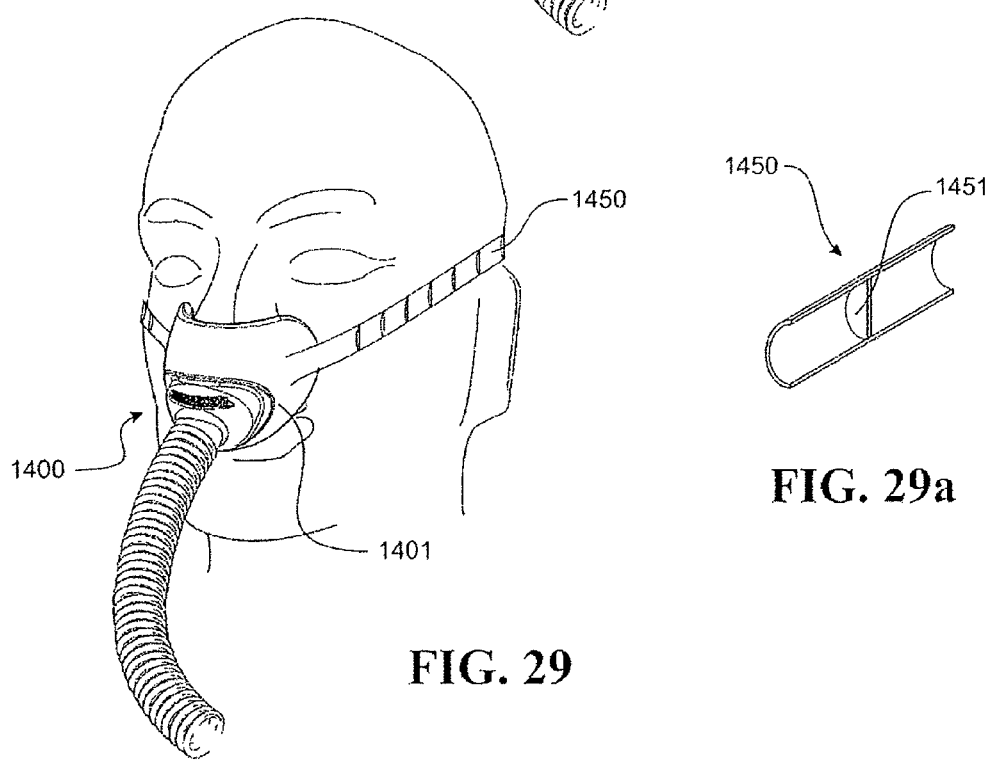
FIG. 29
FIG. 29a

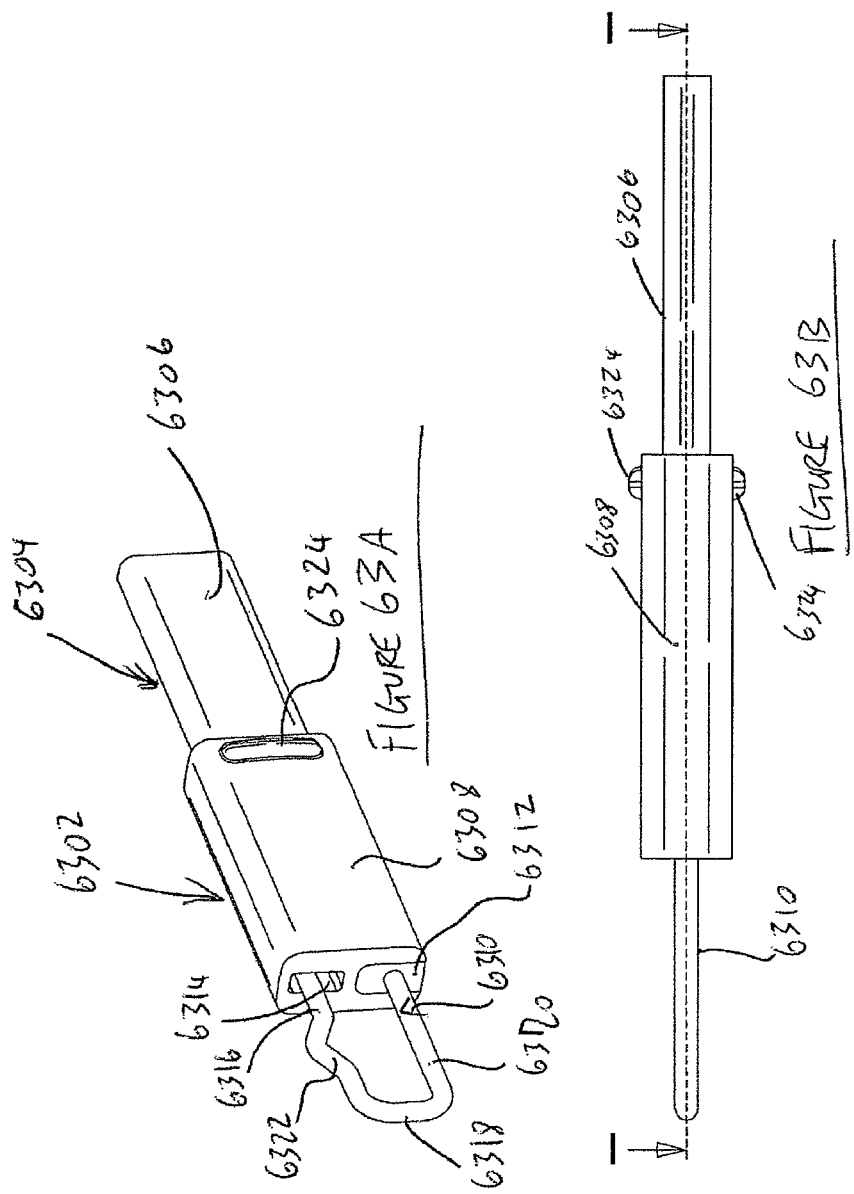

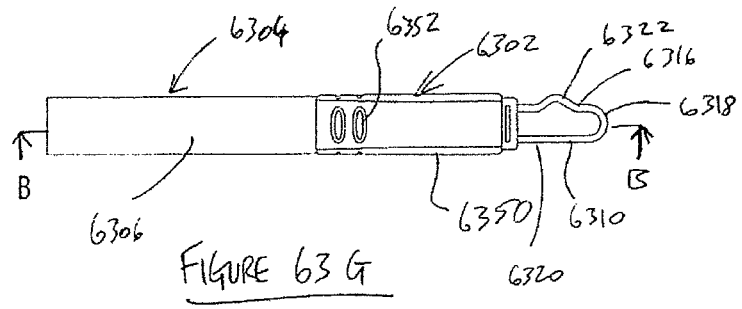
FIGURE 63 G
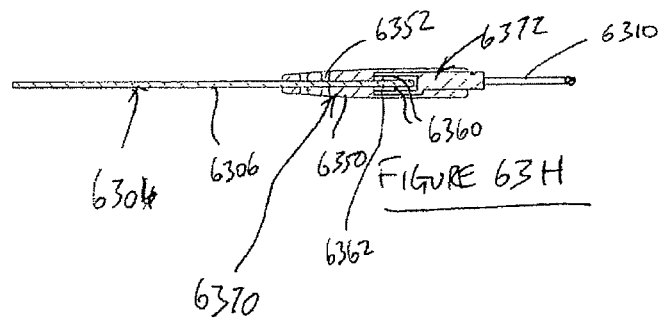
FIGURE 63 H
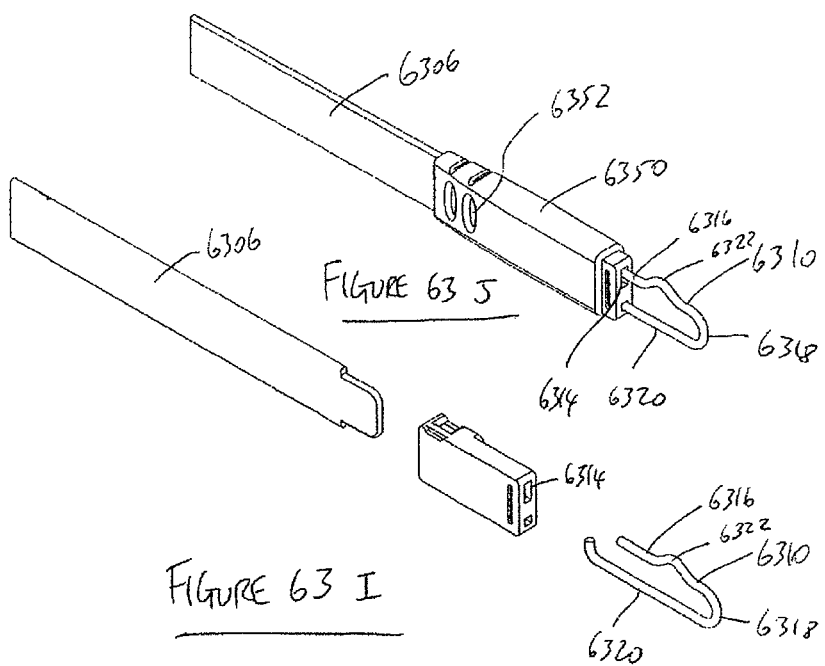
FIGURE 63 J
FIGURE 63 I

PATIENT INTERFACE AND ASPECTS THEREOF

INCORPORATION BY REFERENCE TO ANY PRIORITY APPLICATIONS

Any and all applications for which a foreign or domestic priority claim is identified in the Application Data Sheet as filed with the present application are hereby incorporated by reference and made a part of the present disclosure.

BACKGROUND OF THE INVENTION

Field of the Invention

The present invention generally relates to interfaces for providing a supply of pressurised gas to a recipient via the nasal passages. The present invention also generally relates to devices that also supply gas to the oral passages, for example, by incorporation into a broader full face mask.

Description of the Related Art

The prior art includes a wide variety of interfaces for supplying gases to a recipient. For example, the prior art includes a nasal mask that can be used for supplying gases to a recipient. The nasal mask includes a perimeter seal that seals across, down each cheek alongside the nose and along the surface of the upper lip. The entire enclosed space is pressurised and the recipient may inhale the pressurised gas from the enclosed space. An example is the Flexifit 405™ nasal mask sold by Fisher & Paykel Healthcare.

The prior art also includes a full face mask. The full face mask includes a perimeter seal that extends across the bridge of the nose downward along each cheek beside the nose to the jaw and along the jaw below the lower lip. The perimeter thereby encloses both the nose and mouth. The entire space within the mask frame is pressurised. The recipient may breathe the pressurised gas from the space through either the nose or mouth. An example is the Flexifit 431™ interface sold by Fisher & Paykel Healthcare.

The prior art includes an oral interface including an oral appliance that fits within the user's mouth. An example is the Fisher & Paykel Healthcare Oracle interface.

The prior art includes a nasal pillows interface in which headgear retains a soft plenum in the vicinity of the user's nose. A pair of flexible protrusions engage against the nares of the recipient. Typically, the protrusions are able to axially compress and have a lateral freedom of movement relative to the supporting cushion. An example is the ResMed Swift™ nasal pillows interface.

The prior art includes a nasal cannula interface. The nasal canal interface includes a plenum portion that rests against the upper lip of the user and a pair of prongs. Each prong extends into the nostril of the user. An example is the Nasal-Aire™ interface made by Innomed.

Interfaces such as these are frequently used for delivering pressurised gases to a person being treated for obstructive sleep apnea (OSA) or other sleep disorders. These users typically wear the interface in a home sleeping environment. Comfort and effective sealing even under conditions of patient movement are major considerations.

SUMMARY OF THE INVENTION

An object of the present invention is to provide an interface which will at least provide the industry and users with useful choice.

Certain features, aspects and advantages of an embodiment of the invention comprises a patient interface comprising a supple envelope, bag or balloon, with an air supply aperture and a pair of protruding nostril locators protruding from the envelope, each nasal locator including an outlet aperture, the envelope, bag or balloon inflating under internal pressure from a pressurised gases supply and when pressed against the face of a user, creating a seal with the nose or face of the user in addition to any seal provided by the nasal locators.

According to a further aspect the envelope has at least two integral connectors to attach a head strap to the envelope.

According to a further aspect the interface includes a frame having a gases inlet for connection with a gases supply conduit and a gases outlet including a protruding lip, where the gases supply aperture of the envelope is engaged or engagable over the protruding lip of the frame.

According to a further aspect the frame has at least two integral connectors to attach a head strap to the frame.

According to a further aspect the frame includes a strap to stabilise the envelope, the strap extending above the frame.

According to a further aspect the strap is integrally formed with the frame.

According to a further aspect the strap is separate to the frame yet fastened to said frame.

According to a further aspect the envelope includes an elongate strip integrally formed in the envelope to stabilise the envelope, the strip extending in an arc above the frame.

According to a further aspect the envelope, when inflated without stretch, will not pass through a circular aperture of 40 mm diameter without contact.

According to a further aspect the envelope collapses when not inflated.

According to a further aspect the envelope or the body of the envelope, in use, forms a substantially continuous seal against the user's nose and face that surrounds the nostril locators.

According to a further aspect the envelope wraps completely about the user's nose.

According to a further aspect the envelope has side portions that extend completely about the sides of the user's nose and at least partially over the user's cheeks.

According to a further aspect the envelope has a cut out in the nasal bridge region of the user.

According to a further aspect wherein, in use, the side wall of the envelope rolls to accommodate movement of the mask frame relative to the nose, wherein rolls means that the portion of the envelope adjacent to the frame reduces at one side and extends at the other, and the corresponding portions adjacent the face extend at one side and reduce at the other.

According to a further aspect the envelope allows for this movement in any direction relative to the nose.

According to a further aspect the envelope allows for a roll of at least 10 mm without exposing the nostril locators.

According to a further aspect substantially the entire envelope, except for a region immediately adjacent and including the nostril locators and immediately adjacent and including the inlet opening, is supple, and the region immediately adjacent and including the area immediately adjacent the inlet opening has any suitable stiffness.

According to a further aspect the region immediately adjacent the inlet opening is stiffer than the rest of the envelope.

According to a further aspect the region immediately adjacent the nostril locators is stiffer than the rest of the envelope.

According to a further aspect a connector is engaged with or formed in the interface frame.

According to a further aspect the interface includes a short length of supple breathing conduit that is connectable to the frame.

According to a further aspect the interface includes a including a short length of breathable conduit that is connectable to the frame.

According to a further aspect the interface includes a lanyard or tether connected to a length of breathing conduit connected to the frame.

According to a further aspect the lanyard or tether is connected to the conduit at a location between 10 cm and 50 cm from the frame.

According to a further aspect the interface includes a frame supporting the envelope, the frame including at least one soft or flexible portion at the perimeter.

According to a further aspect the frame includes at least a pair of extended support members at the perimeter, the support members located either side of the frame such that they may, but do not necessarily, contact portions of the face of the user in use.

According to a further aspect the interface includes at least one strap extending from one side portion of the frame to the other side portion of the frame, the strap being sufficient to pass around the back of the head of the user.

According to a further aspect the strap is adjustable in length.

According to a further aspect each end of the strap is bifurcated and the two limbs of the bifurcated end connect to the side portion of the frame at spaced apart locations.

According to a further aspect the interface includes a bias flow outlet in one or more of the envelope, a frame or connector.

According to a further aspect the envelope is inflated and holds its shape against the force of gravity with an elevated internal pressure equivalent to 3 cm $H_2O$.

Certain features, aspects and advantages of an embodiment of the invention comprises an interface that includes an inflatable envelope (that could also be referred to as a bag or balloon) having a supple wall structure. The inflatable envelope has a pair of locating protrusions that engage in the nostrils of the user. The locating protrusions supply gases flow to the user from inside the envelope. The envelope is so supple, and of sufficient dimension and shape, that when the inflated envelope is pressed against the face of a user, with the locating protrusions engaged in the nostrils of the user, the envelope contacts the surfaces of the user's face (the nose, the upper lip and the cheeks) and provides a seal.

Certain features, aspects and advantages of an embodiment of the invention comprises a patient interface comprising: a single loop headstrap, a mask for covering at least the nostrils of the user, the single loop headstrap extending from the mask at either end, a swivel or ball joint at the mask to couple a supply conduit to the mask in use to allow rotation of the supply conduit through different angles and orientations relative to the mask.

According to a further aspect, the mask includes an inflatable seal with an air supply aperture and a pair of protruding nostril locators protruding from the seal, each nasal locator including an outlet aperture.

According to a further aspect, the seal inflates under internal pressure from a pressurised gases supply and when pressed against the face of a user, creating a seal with the nose or face of the user in addition to any seal provided by the nasal locators.

According to a further aspect, the interface includes a frame having a gases inlet for connection with a gases supply conduit, and a gases outlet including a protruding lip, and the gases supply aperture of the seal is engaged or engagable over the protruding lip of the frame.

According to a further aspect, the seal, in use, forms a substantially continuous seal against the user's nose and face that surrounds the nostril locators.

According to a further aspect, except for a region immediately adjacent and including the nostril locators and immediately adjacent and including the air supply aperture, the seal is supple, and the region immediately adjacent and including, the inlet opening and has any suitable stiffness.

According to a further aspect, the patient interface includes at least a pair of extended support members at the perimeter of the mask, the support members located either side of the mask such that they may, but do not necessarily, contact portions of the face of the user in use.

According to a further aspect, the strap extends from one side portion of the frame to the other side portion of the frame, the strap being sufficient to pass around the back of the head of the user.

According to a further aspect, the patient interface includes a short length of supple conduit connected to the swivel or ball joint.

According to a further aspect, the patient interface includes a laterally extended support that can press on a lower facial portion of the user outside the periphery of the seal.

According to a further aspect, the laterally extended support can press on the lower cheek portion of the user.

According to a further aspect, the laterally extended support may only occasionally contact the face of the user in use.

Certain features, aspects and advantages of an embodiment of the invention comprises a patient interface including a mask including seal means for sealing with the face of a user and frame means for supporting the seal, and means for securing he mask to the head of a user.

According to a further aspect, the patient interface includes a conduit for delivering gases to the mask, and means for supporting the weight of the conduit from substantially affecting the mask in use.

Certain features, aspects and advantages of an embodiment of the invention comprises a patient interface comprising: a mask for covering at least the nostrils of the user, and including a seal body and a frame connected with the seal and a laterally extended support that can press on a lower facial portion of the user outside the periphery of the seal.

According to a further aspect, the mask includes an inflatable seal with an air supply aperture and a pair of protruding nostril locators protruding from the seal, each nasal locator including an outlet aperture.

According to a further aspect, the seal inflates under internal pressure from a pressurised gases supply and when pressed against the face of a user, creating a seal with the nose or face of the user in addition to any seal provided by the nasal locators.

According to a further aspect, in use, the side wall of the envelope rolls to accommodate movement of the mask frame relative to the nose, wherein rolls means that the portion of the envelope adjacent to the frame reduces at one side and extends at the other, and the corresponding portions adjacent the face extend at one side and reduce at the other.

According to a further aspect, the frame includes at least a pair of extended support members at the perimeter, the support members located either side of the frame such that they may, but do not necessarily, contact portions of the face of the use in use.

According to a further aspect, the patient interface includes a single loop strap extending from one side portion of the frame to the other side portion of the frame, the strap being sufficient to pass around the back of the head of the user.

According to a further aspect, the laterally extended support can press on the lower cheek portion of the user.

According to a further aspect, the laterally extended support may only occasionally contact the face of the user in use.

Certain features, aspects and advantages of an embodiment of the invention comprises a patient interface comprising: a nasal seal including a face contacting side, the nasal seal being formed of a soft flexible material, and including a central portion to extend across the base of the nose, and a side portion extending from each end of the central portion, each side portion extending across the a side of the nose, a face contacting side of the seal being supple to conform under internal pressure to the surfaces of the nose of a wearer, including, at the side portions of the seal, to outside surfaces of the sides of the nose, an exterior side including regions much stiffer than the supple interior side, the regions extending into the side portions of the seal.

According to a further aspect, wherein the side portions of the seal are substantially parallel to each other and substantially normal to the central portion of the seal.

According to a further aspect, the outer walls of the side portions of the seal are aligned to have an angle between their orientations between 0 degrees and 30 degrees.

According to a further aspect, the seal includes a pair of nasal locators on the face contacting side, and the seal is stiffer in the region immediately adjacent and including the nasal locators than in a region surrounding this region, on the face contacting side of the seal.

According to a further aspect, a peripheral portion of the seal, joining the face contacting side to the exterior side is supple and allows the interior side of the seal to displace relative to the exterior side.

According to a further aspect, the exterior side of the central portion of the seal includes an aperture for passing gases to and from the interior of the seal.

According to a further aspect, the supple portions of the seal comprise a silicone material with a thickness between 0.05 mm and 0.5 mm.

According to a further aspect, the supple portions of the seal comprise an elastomer with a thickness between 0.1 mm and 0.2 mm.

According to a further aspect, the stiff portions of the seal comprise a silicone material with a thickness between 2 mm and 5 mm.

According to a further aspect, the stiff portions of the seal comprise an elastomer with a thickness between 2 mm and 3 mm.

According to a further aspect, the region immediately adjacent and including the nasal locators comprises a silicone material with a thickness between 0.5 mm and 2 mm.

According to a further aspect, the seal has an overall width from outside surface of one side portion to outside surface of the other side portion of between 30 mm and 60 mm.

According to a further aspect, the seal has an overall depth, from the outer surface of the central portion to a line joining the extreme ends of each side portion, between 40 mm and 65 mm.

According to a further aspect, the patient interface includes a body assembled to the nasal seal, the body being formed of a material more rigid than the nasal seal, and together with the nasal seal forming an enclosure having an inlet opening and a patient outlet opening, with a swivelling elbow connected to the inlet opening.

According to a further aspect, the connection of the swivel elbow to the body provides for rotation of the swivel elbow relative to the body and pivoting of the swivel elbow relative to the body about at least a transverse axis.

According to a further aspect, the connection comprises a ball joint.

According to a further aspect, the elbow includes a first end and a second end and a flow path between the first end and the second end, the flow path aligned in the first direction at the first end and the second direction at the second end, and the first direction and the second direction including an angle of between 120° and 180°, According to a further aspect, the angle is between 120° and 150°.

According to a further aspect, the angle is between 130° and 140°.

According to a further aspect, the elbow includes a gas washout vent.

According to a further aspect, the gas washout vent is aligned with a gas flow path into the elbow from the nasal seal and body assembly.

According to a further aspect, the gas washout vent comprises a plurality of holes through a wall of the elbow.

According to a further aspect, the patient interface includes a body assembled to the seal, and a strap extending from the assembled body and nasal seal in a loop, the strap departing a first portion of the assembled body and nasal seal at one end and a second portion of the assembled body and nasal seal at its other end.

According to a further aspect, the strap comprises a single undivided band along the length of the strap that engages the head of the wearer.

According to a further aspect, the strap engages the body at either end.

According to a further aspect, the body is formed from a rigid material, the strap is relatively flexible compared to the body and includes a soft portion, a portion of the strap that engages the body formed of a material more flexible than the material of the boy and less flexible than the material of the strap such that, when engaged to the body, the soft portion forms a soft extension of the body.

According to a further aspect, the soft portion extends 5 mm to 60 mm along the strap.

According to a further aspect, the strap engages the body with a releasable connector at either end.

According to a further aspect, the strap includes a soft cover portion extending from the releasable connector for a distance of 5 mm to 60 mm along the strap, the soft cover portion being formed of a material softer than the body.

According to a further aspect, the band is narrow, preferably less than 10 mm wide.

According to a further aspect, the band is less than 6 mm wide.

According to a further aspect, the band has a stiffness less than 2N per 100 mm extension from a relaxed condition.

According to a further aspect, the band is formed from a knitted or braided yarn incorporating filaments of a material with high elasticity and filaments of material of much higher stiffness.

According to a further aspect, the strap includes soft end portions that are more rigid than the strap between the end portions, but softer than the body, the soft end portions also acting as soft extension portions of the body.

According to a further aspect, the patient interface includes a tube depending from the seal and body, and a tube support, connected to the tube and connectable to the neck or clothing of a patient.

According to a further aspect, the tube support includes a collar fastenable about the neck of a wearer.

According to a further aspect, the collar has a first end portion and a second end portion, the first end portion and the second end portion include a fastening arrangement allowing the end portions to be fastened with a selected amount of overlap.

According to a further aspect, the collar includes a third end portion and a fourth end portion and a connector connecting the third end portion to the fourth end portion.

According to a further aspect, the connector is configured to release the third end portion from the fourth end portion upon application of tension across the connector greater than a release tension, wherein the release tension is less than 10N.

According to a further aspect, the collar is between 30 mm and 60 mm wide.

According to a further aspect, the collar has a core material and a cover material surrounding the core material.

According to a further aspect, the core material is a dimensionally stable, breathable mesh.

According to a further aspect, the cover material is a braided or knitted natural fibre.

According to a further aspect, the tube support includes a tether extending from the collar, with a connector at one end secured or securable to the tube.

According to a further aspect, tether includes a connector at the outer end, with the collar passing through the second connector.

According to a further aspect, the tether includes a first end and a second end and a connector connecting the first end and the second end, the connector being configured to release upon application of a tension above a release tension, wherein the release tension is less than 10N.

According to a further aspect, the connector of the strap includes a first portion and a second portion, and in the engaged condition, the first portion can swivel relative to the second portion.

According to a further aspect, the connector to engage with the tube comprises a ring.

According to a further aspect, the patient interface includes a body connected to the seal, and wherein the body includes a nasal seal engaging portion that engages an outward side of the seal, an inlet opening and at least one strap engaging portion from which extends a loop strap to secure the interface to the patient.

According to a further aspect, the patient interface includes a soft intermediate portion where the loop strap extends from the strap engaging portion, the soft intermediate portion being more rigid than the strap but formed of material softer than the material of the body.

According to a further aspect, the body includes two strap engaging portions, each strap engaging portion extending laterally away from the inlet opening, from opposite sides of the inlet opening.

According to a further aspect, each strap engaging portion extends away from the inlet opening in a region where the strap engaging portion overlaps with the outer wall of the seal.

According to a further aspect, a central portion of the body defines a convex shape generally matching a convex shape of the outer wall of the body, with strap engaging portions extending from lateral extremes of the central portion, the strap engaging portions extending away from the central portion at an angle outwardly aligned relative to the general convex shape.

According to a further aspect, the strap engaging portions extend away from the outer wall of the seal with an included angle between them greater than 30 degrees.

According to a further aspect, the strap engaging portion from the point where it diverges from the outer wall of the seal is between 50% and 150% of the length of the equivalent length of the outer wall of the seal.

According to a further aspect, the patient interface includes a body engaged with the nasal seal, the body being more rigid than the nasal seal, wherein a lip support depends from the body, and extends beyond an edge of the seal.

According to a further aspect, the lip support includes one or more pads for engaging against an upper lip portion of the wearer.

According to a further aspect, the lip support includes two depending legs, spaced apart at either lateral region of the seal, each leg extending beyond a lateral portion of the lower edge of the seal.

According to a further aspect, each leg carries a pad portion oriented to present a face against the upper lip.

According to a further aspect, the legs are moulded to have lower stiffness about an axis parallel to the lip portion of the wearer which they will contact, than about an axis normal to the plane of the lips.

Certain features, aspects and advantages of an embodiment of the invention comprises headgear for a patient interface, the headgear comprising: resilient band having a width between 3 mm and 6 mm, a stiffness providing an extension of 150 mm with a force less than 2N, a first end connected or connectable to a first lateral portion of a mask, and a second end connected or connectable to a second lateral portion of a mask.

According to a further aspect, the band is between 350 mm and 450 mm long in its relaxed length.

According to a further aspect, the band is between 60 mm and 110 mm longer upon application of an extension force of 1N.

According to a further aspect, the band is constructed from a knitted or braided yarn, where the yarn includes filaments of a first material and filaments of a second material of high elasticity but much lower stiffness than the first material.

According to a further aspect, the band comprises a braided yarn, and the yarn comprises an elastane filament with a spun wrapper.

According to a further aspect, the band comprises a plurality of braided thread bundles, and each thread bundle comprises at least two threads, and each thread comprises an elastane core and spun wrapper.

According to a further aspect, the first strap end, the second strap end or both include a soft cover portion, extending 5 mm to 60 mm along the strap, the soft cover portion being more rigid than the strap.

According to a further aspect, the cover portion is of a softer material than the lateral portion of the mask to which it is intended to connect.

According to a further aspect, the headgear includes a first connector at the first end and a second connector at the second end.

According to a further aspect, the connector includes a resiliently deformable spring clip engaged in a clip body.

According to a further aspect, the connector includes a cover surrounding and at least substantially encapsulating the clip body and a portion of the band, the cover being more rigid than the band and being formed of a material softer than the material of the clip body.

Certain features, aspects and advantages of an embodiment of the invention comprises a patient interface including a strap according to any one or more of the above paragraphs.

Certain features, aspects and advantages of an embodiment of the invention comprises a patient interface comprising: a nasal seal including a face contacting side, the nasal seal being formed of a soft flexible material, a body assembled to the nasal seal, the body being formed of a material more rigid than the nasal seal, and together with the nasal seal forming an enclosure having an inlet opening and a patient outlet opening, and a lip support depends from the body, and extends beyond an edge of the seal.

According to a further aspect, the lip support includes one or more pads for engaging against an upper lip portion of the wearer.

According to a further aspect, the lip support includes two depending legs, spaced apart at either lateral region of the seal, each leg extending beyond a lateral portion of the lower edge of the seal.

According to a further aspect, each leg carries a pad portion oriented to present a face against the upper lip.

According to a further aspect, the legs are moulded to have lower stiffness about an axis parallel to the lip portion of the wearer which they will contact, than about an axis normal to the plane of the lips.

According to a further aspect, the patient interface includes a gases supply tube depending from the body and a strap extending from the assembled frame and nasal seal in a loop, the strap departing a first portion of the assembled body and nasal seal at one end and a second portion of the assembled body and nasal seal at its other end.

Certain features, aspects and advantages of an embodiment of the invention comprises a patient interface comprising: a mask, a tube depending from the mask, and a tube support, connected to the tube and including a collar fastenable about the neck of a wearer.

According to a further aspect, the collar has a first end portion and a second end portion, the first end portion and the second end portion including a fastening arrangement allowing the end portions to be fastened with a selected amount of overlap.

According to a further aspect, the collar includes a third end portion and a fourth end portion and a connector connecting the third end portion to the fourth end portion.

According to a further aspect, the connector is configured to release the third end portion from the fourth end portion upon application of tension across the connector greater than a release tension, wherein the release tension is less than 10N.

According to a further aspect, the collar is between 30 mm and 60 mm wide.

According to a further aspect, the collar has a core material and a cover material surrounding the core material.

According to a further aspect, the core material is a dimensionally stable, breathable mesh.

According to a further aspect, the cover material is a braided or knitted natural fibre.

According to a further aspect, the tube support includes a tether extending from the collar, with a connector at one end secured or securable to the tube.

According to a further aspect, the tether includes a connector at the outer end, with the collar passing through the second connector.

According to a further aspect, the tether includes a first end and a second end and a connector connecting the first end and the second end, the connector being configured to release upon application of a tension above a release tension, wherein the release tension is less than 10N.

According to a further aspect, the connector of the tether includes a first portion and a second portion, and in the engaged condition, the first portion can swivel relative to the second portion.

Certain features, aspects and advantages of an embodiment of the invention comprises a patient interface comprising: a nasal seal including a face contacting side, the nasal seal being formed of a soft flexible material, and including a central portion to extend across the base of the nose, and a side portion extending from each end of the central portion, each side portion extending across the a side of the nose, a body connected to the seal, including a nasal seal engaging portion that engages an outward side of the seal, an inlet opening and at least two strap engaging portions, each strap engaging portion extending laterally away from the inlet opening, from opposite sides of the inlet opening, and a strap extending between the strap engaging portions; and wherein a central portion of the body defines a convex shape generally matching a convex shape of the outer wall of the body, with strap engaging portions extending from lateral extremes of the central portion, the strap engaging portions extending away from the central portion at an angle outwardly aligned relative to the general convex shape.

According to a further aspect, the strap engaging portions extend away from the outer wall of the seal with an included angle between them greater than 30 degrees.

According to a further aspect, the strap engaging portion from the point where it diverges from the outer wall of the seal is between 50% and 150% of the length of the equivalent length of the outer wall of the seal.

According to a further aspect, the patient interface includes a soft intermediate portion where the loop strap extends from the strap engaging portion, the soft intermediate portion being more rigid than the strap but formed of material softer than the material of the body.

Certain features, aspects and advantages of an embodiment of the invention comprises a patient interface comprising: a single loop headstrap, a mask for covering at least the nostrils of the user, the single loop headstrap extending from the mask at either end, a supply conduit less than 200 mm long, coupled to the mask for free swivelling movement including substantial rotation about multiple orthogonal axes.

According to a further aspect, the supply tube is flexible to an extent that the tube passes the test described herein with reference to FIG. 64.

Certain features, aspects and advantages of an embodiment of the invention comprises a patient interface comprising: a mask for covering at least the nostrils of the user, a supply port on the mask for receiving a supply of gases, a bias flow vent on the mask extending from an inside of the mask to an outside of the mask, the bias flow vent directing flow in a direction less than 45° to the coronal plane of the head of a hypothetical wearer, and in a direction generally toward the forehead.

According to a further aspect, the bias flow vent comprises at least one bias flow aperture in a wall of the mask, the portion of the wall having the bias flow aperture being aligned more than 45° to the coronal plane of the wearer.

According to a further aspect, the portion of the wall having the bias flow holes is located within a front wall of the mask, and the portion forms a shelf relative to a surrounding portion of the front wall.

According to a further aspect, a plurality of bias flow holes are distributed in a curve around the upper front portion of the interface.

According to a further aspect, the mask has a general U-shape or V-shape to wrap around the nose of the user, and the bias flow vent is located at the base of the U or V.

According to a further aspect, the seal does not cover the nasal bridge of the wearer.

Certain features, aspects and advantages of an embodiment of the invention comprises a patient interface comprising: a frame and a seal, the seal including a patient-facing side with at least one patient opening and a frame-facing side with at least one frame-facing opening, the seal engaging with the frame at a lip defined by the perimeter of the frame-facing opening, the frame including a first component part and a second component part, the first component part including a first portion of a channel for engaging the lip of the seal, the second component part including a second portion of the channel for engaging the lip of the seal, the seal being engageable and disengageable from the channel with the first and second component parts connected to form the channel.

Certain features, aspects and advantages of an embodiment of the invention comprises a patient interface comprising: a frame and a seal, the frame including a first component part and a second component part engaged together, the first component part including a portion forming a socket with surfaces for contacting moving parts of a freely swivelling connector, the second part comprising a outer cover, with an opening at the location of the socket of the first part, and the patient interface further including a connector with a joining part projecting past the cover into the socket of the first part to be engaged in the socket of the first part for free swivelling movement.

According to a further aspect, the first component is formed from a different material to the cover, and the cover and the connector are formed from the same material.

According to a further aspect, the patient interface includes a seal including a pair of nasal locators extending from a supple background, each nasal locator including a tip, the nasal locator becoming narrower moving from the background to the tip, and an opening in the tip of the nasal locator, the opening, and the cross-sectional profile of the tip portion of the nasal locator, being oval or elliptical and having a ratio of the length of the major axis to the length of the minor axis greater than 1.5.

According to a further aspect, the ratio of the length of the major axis to the length of the minor axis is between 1.5 and 3.

According to a further aspect, the tip portion of the nasal locator includes a lip adjacent the tip opening, the lip being thickened relative to adjacent portions of the tubular portion.

According to a further aspect, the nasal locator includes a dome portion adjacent the background and a tubular portion extending from an apex of the dome portion.

According to a further aspect, the tubular portion is tapered, extending from the dome portion to the tip portion.

According to a further aspect, the cross-section of the nasal locator in planes parallel to the plane of the tip opening is oval or elliptical throughout the tubular portion and upper parts of the dome portion.

According to a further aspect, the ratio of the length of the major axis of the oval cross-section to the length of the minor axis of the oval cross-section reduces, gradually extending from the tip of the tubular portion to the base of the dome portion.

According to a further aspect, the flow projecting axes of the two nasal locators converge at a location between 10 mm or 40 mm from the tips of the nasal locators.

According to a further aspect, the central axis of the nasal locator, projected beyond the tips of the locators, converge to become closest at a location 10 mm to 20 mm beyond the tips of the nasal locators.

According to a further aspect, if the tip openings of the nasal locators are projected on to the coronal plane of a hypothetical wearer, the oval shapes of the tip openings are aligned to such that the major axes converge at an angle between 60 degrees and 120 degrees.

Certain features, aspects and advantages of an embodiment of the invention comprises a patient interface comprising: a frame and a seal, the seal including a patient-facing side with at least one patient opening and a frame-facing side with at least one frame-facing opening, the seal engaging with the frame at a lip defined by the perimeter of the frame-facing opening, the frame including a front face portion in the region of a swivel connection to a supply conduit, the front face portion being inclined relative to the coronal plane of the hypothetical wearer of the interface such that the lower edge of the portion is closer to the coronal plane than the upper edge of the portion, and the connector turning flow from an entry to the connector to an exit of the connector through an angle between 30 degrees and 70 degrees, the connector and the inclined outward face portion of the mask frame together allowing for free swivelling movement of the conduit, the conduit to adopt a position more or less parallel to the coronal plane of the hypothetical wearer, and the connector remaining close to the face of the wearer.

According to a further aspect, the connector does not include a bias flow vent.

Certain features, aspects and advantages of an embodiment of the invention comprises a patient interface comprising: a frame and a seal, the seal including a patient-facing side with at least one patient opening and a frame-facing side with at least one frame-facing opening, the seal engaging with the frame at a lip defined by the perimeter of the frame-facing opening, the frame including a supply opening through a front wall of the frame, a ring portion extending from the front wall to define a passage projecting from the inside surface of the front wall of the frame, and a projecting wall passing around the internally open end of the ring portion and engaging the lip of the seal, the front wall of the frame and the ring portion, together with other portions of the frame, defining a plenum chamber, with a bias flow vent through a wall of the plenum chamber, and an open area between the ring portion and the structure of the channel providing a flow path between the interior of the seal and the plenum chamber.

According to a further aspect, the bias flow holes are arranged through the wall of the frame in an area of the upper portion of the plenum chamber.

According to a further aspect, the ring portion is formed as part of a first component of the frame, and the front wall of the frame is formed as part of a second component, the two components being secured together to define the plenum chamber.

According to a further aspect, the projecting wall comprises a channel, the channel receiving the lip of the seal.

According to a further aspect, the channel follows a closed curved path of overall width greater than height, such that the plenum chamber is predominantly formed to either side of the ring portion.

According to a further aspect, the ring portion connects to the upper and lower central portions of the projecting wall and the flow path from the seal to the plenum chamber passes either side of the ring portion.

According to a further aspect, the projecting wall is formed as part of the same component as the ring portion.

According to a further aspect, the bias flow vent is formed through the front wall of the second component.

According to a further aspect, the first component includes laterally projecting shield portions, the internal surfaces of the shield portions fitting against outer surfaces of an outward wall of the seal to constrain the outward deflection of the seal.

According to a further aspect, the second component includes downwardly and laterally depending stabilisers for stabilising on the upper lip region of a wearer.

According to a further aspect, the first frame component comprises a skeletal frame, with a least a portion of the stabiliser parts of the component comprising an over-moulded soft material.

Certain features, aspects and advantages of an embodiment of the invention comprises a patient interface including a soft resilient seal, a rigid frame, headgear connecting to the frame, rigid projections at the connection of the headgear to the frame, the headgear being very floppy within 60 mm of the frame, and, between this location and the projections, a soft portion, more rigid than the floppy portion of the headgear but made of a softer material than the rigid frame.

According to a further aspect, the projections are alike to prongs, long and slender.

According to a further aspect, the soft portion extends from the general path of the prongs.

According to a further aspect, the projection is made up of a combination of a portion of the mask frame and a clip portion of the headgear.

According to a further aspect, the soft portion is part of the headgear.

According to a further aspect, the headgear is a simple single loop strap.

According to a further aspect, the projections project laterally beyond the breadth of the seal.

Certain features, aspects and advantages of an embodiment of the invention comprises an interface according to any plurality of the preceding paragraphs.

The term "comprising" is used in the specification and claims, means "consisting at least in part of". When interpreting a statement in this specification and claims that includes "comprising", features other than that or those prefaced by the term may also be present. Related terms such as "comprise" and "comprises" are to be interpreted in the same manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

BRIEF DESCRIPTION OF THE DRAWINGS

Various forms of the interface will be described with reference to the accompanying drawings. One form will be described with reference to FIGS. 1A and 1B. Behavioural and sealing characteristics of this example will be described with reference to FIGS. 1C to 1E. Additional examples of the form of the inflating envelope will be described with reference to FIGS. 1F to 1H. An additional example of an interface with an alternative frame is described with reference to FIG. 1I. A further example of an interface with an alternative envelope and frame is described with reference to FIGS. 2A to 2C. Other examples of interfaces and parts of interfaces are described with reference to FIGS. 3 to 65.

FIG. 1CA shows the seal limp and deflated. FIGS. 1CB and 1CC show the envelope with progressively greater inflation. FIG. 1CD shows the envelope inflated.

FIGS. 1DA to 1DC show how the envelope retains a seal despite substantial vertical movement. FIG. 1DA shows an intended position on the user's face. FIG. 1DB shows a less than ideal position that might occur if the frame was moved upward. FIG. 1DC shows a less than ideal position that might occur if the frame was moved downward.

FIG. 1E FIG. 1EA shows an intended position on the user's face. FIG. 1EB shows a less than ideal position that might occur if the frame was moved to the user's right. FIG. 1EC shows a less than ideal position that might occur if the frame was moved to the user's left.

FIG. 1I shows an interface with an alternative frame with a stabilising strap.

FIG. 4A shows the seal component from an outward facing side, FIG. 4B shows the seal from a patient-facing side and FIG. 4C shows a side view of the seal.

FIGS. 10A to 10C are perspective views illustrating a patient interface. FIG. 10A is a front view, FIG. 10B is a profile view, and FIG. 10C is a back view.

FIGS. 11A to 11H are views of the soft seal component of the interface of FIGS. 10A to 10C. FIG. 11 A is a top view. FIG. 11B is a front view. FIG. 11C is a rear view taken from a position directly facing the open end of a nasal locator. FIG. 11D is a cross section through section CC in FIG. 11C. FIG. 11E is a cross section through line DD in FIG. 11C. FIG. 11F is a cross section through line EE in FIG. 11E. FIG. 11G is a cross section through line GG in FIG. 11E. FIG. 11H is a cross section through line HH in FIG. 11E.

FIG. 12A is a front perspective view of the frame assembly. FIG. 12B is a rear perspective view of the frame assembly. FIG. 12C is a side profile of the frame assembly. FIG. 12D is an assembly view of two components of the frame assembly. FIG. 12E is a back view of the frame assembly. FIG. 12F is a front view of the frame assembly. FIG. 12G is a cross sectional side view taken through line AA of FIG. 12F. FIG. 12H is a cross sectional top view, taken through line BB in FIG. 12F.

FIG. 26 shows a third embodiment of a head strap that may be used with an interface.

FIG. 27 shows a fourth embodiment of a head strap that may be used with an interface.

FIG. 27a shows the extendible portion of the head strap of FIG. 27 in extended and contracted conditions.

FIG. 28 shows a fifth embodiment of a head strap that may be used with an interface.

FIGS. 29 and 29A shows a sixth embodiment of a head strap that may be used with an interface.

FIGS. 63A to 63C illustrate aspects of a preferred headgear of the interface of FIGS. 10A to 10C. FIG. 63A is a perspective view of a portion of a headgear, including an end of a headstrap and a connector. FIG. 63B is a top view of the strap and connector. FIG. 63C is a view showing both (in cross-section) the connector and the socket of the frame assembly which receives the connector in use.

FIGS. 63D to 63J illustrate another preferred headgear. FIG. 63D shows a portion of the headgear, connector and a portion of the frame assembly to which it connects. FIG. 63E is a top view of the assembly of FIG. 63D. FIG. 63F is a sectional view through line AA of FIG. 63E.

FIG. 63G is a side elevation of the strap portion and connector of FIG. 63G. FIG. 63H is a cross-section through line BB of the connector and strap portion of FIG. 63G. FIG. 63I is an assembly drawing of an exploded view of the strap portion and connector of FIG. 63G. FIG. 63J is a perspective view of the strap portion and connector of FIG. 63B.

DETAILED DESCRIPTION OF THE PREFERRED EMBODIMENT

According to one or more examples, an interface includes an inflatable envelope (that could also be referred to as a bag or balloon) having a supple wall structure. The inflatable envelope has a pair of locating protrusions that engage in the nostrils of the user. The locating protrusions supply gases flow to the user from inside the envelope. The envelope is so supple, and of sufficient dimension and shape, that when the inflated envelope is pressed against the face of a user, with the locating protrusions engaged in the nostrils of the user, the envelope contacts the surfaces of the user's face (the nose, the upper lip and the cheeks) and provides a seal.

An example of the interface will be described in detail. Many variations are possible to both the seal part of the interface and to the supporting frame and straps. For example, the seal part of the interface could be supported by the type of frames and straps that have been described previously for use with nasal masks, or nasal pillows interfaces. Though not explicitly described these variations are within the scope of certain features, aspects and advantages of an embodiment of the present invention. Many variations on the shape of the envelope and the shape of the nasal locators also are possible. Some variations are illustrated in FIGS. 1F to 1H for example but without limitation.

Figure 1A:
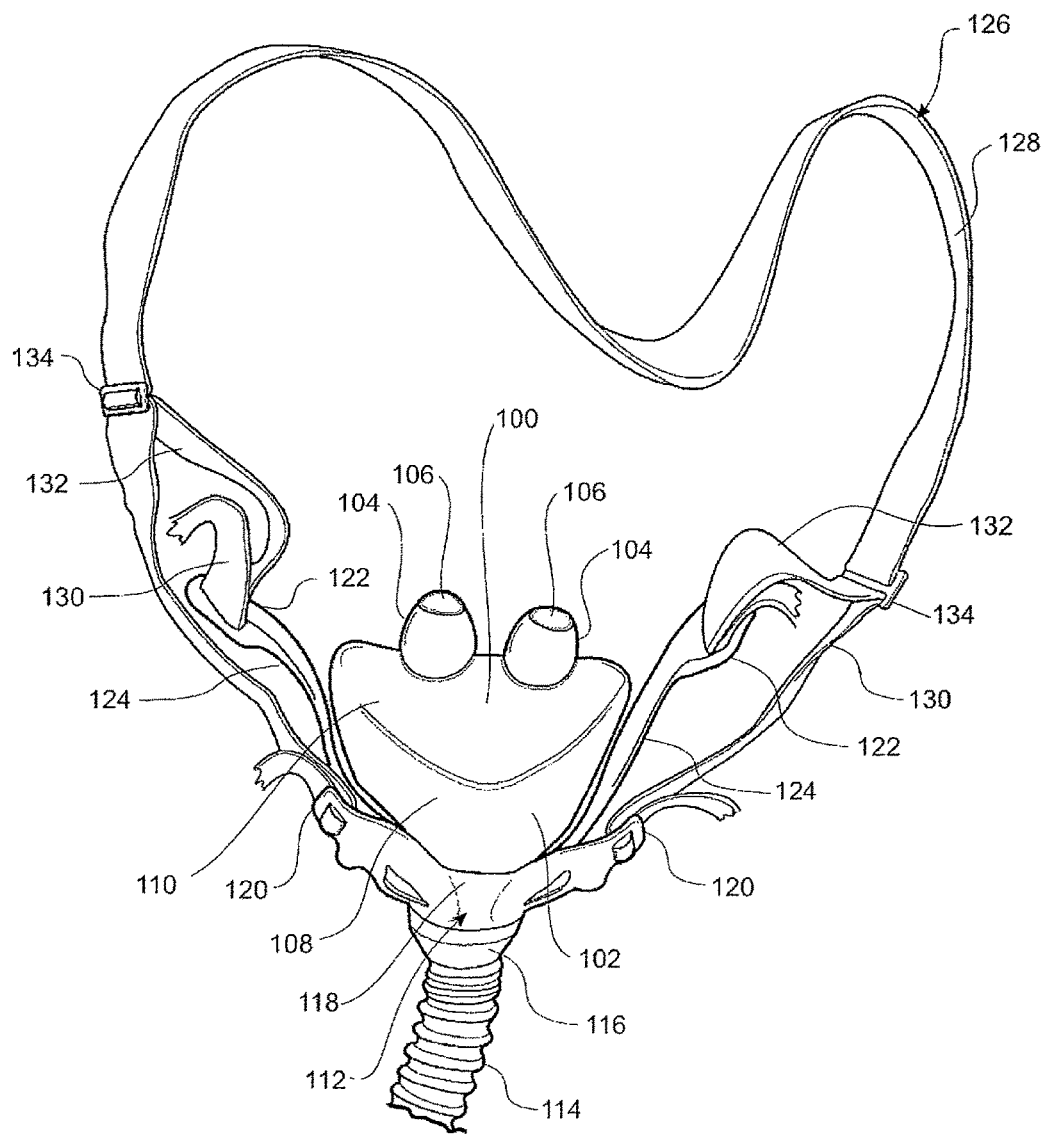
FIG. 1A is a view from above of an example interface including inflatable envelope, supporting frame, and straps.
Figure 1B:
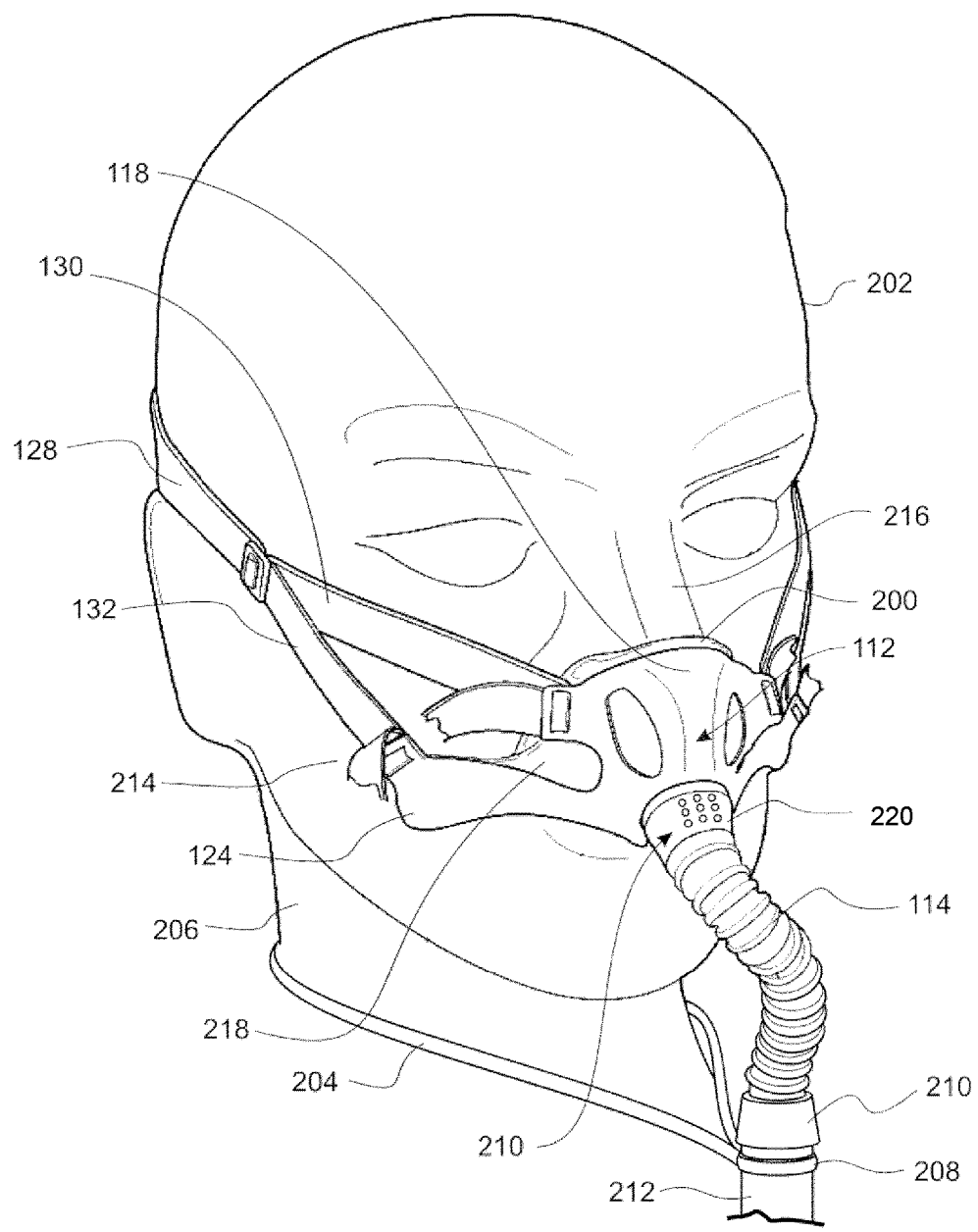
FIG. 1B is an illustration showing the interface of FIG. 1A in position on the head of a user.

FIG. 1A is a view from above of an example interface including an inflatable envelope, a supporting frame, and straps. FIG. 1B is an illustration showing the interface of FIG. 1A in position on the head 202 of a user.

The interface includes a seal body 100. The seal body 100 includes a supple envelope 102. When inflated, the supple envelope 102 has a general blob shape with a substantially uniform aspect ratio. The envelope has a low wall thickness. The envelope is formed from a material having sufficient elasticity and yield strength that the combination renders the envelope supple. The envelope is capable of repeated drastic deformations without failure. Possible materials include latex, vinyl, silicone and polyurethane. Typically, wall thickness would be below about 0.5 mm and could be lower than about 0.2 mm.

The seal body includes a pair of nostril locators 104 protruding from the envelope. Preferably the nostril locators are formed integral with the envelope. Each nostril locator includes an outlet aperture for supplying gas from inside the envelope to a user wearing the interface.

The seal body may broadly be shaped to have a sidewall 108 and a seal surface 110. The sidewall 108 extends all around the body. In use, either or both of the sidewall 108 and the seal surface 110 may press against surfaces of the user's face to form a seal that conforms around the nose and that surrounds the nostril locators. The nostril locators may or may not be formed to also seal with the nostrils of the user.

The seal body 100 includes an inlet opening at the base, which is approximately opposite the nostril locators 104 in the illustrated configuration.

The seal body may be formed, for example, by coating over a male mould. Coating may be performed by spraying the desired material over the male mould in a sequence of coats, or by dipping the male mould into a bath of the desired material one or more times to build up the desired thickness. Apertures in the seal body (for example for the outlet apertures in the nostril locators) may be subsequently cut. The seal body may be pressure tested prior to cutting the apertures.

A substantial extent of the seal body or envelope is supple. A region immediately adjacent and including the nostril locators and immediately adjacent and including the inlet opening are less supple than other regions. These less supple areas desirably have a shape and can be of any suitable stiffness. It is preferred that these less supple areas are stiffer and, as such, they may be formed of a thicker less pliant material or they may be formed thicker in the same material as the rest of the envelope.

The envelope may be so supple that, when not pressurised with gases, the envelope, bag or balloon hangs limp and does not hold its shape. However, in some embodiments, it is desired that the envelope retain some shape when not in use (i.e., when not pressurised). Therefore, the envelope may have some natural shape. For an example, see the embodiment of FIGS. 2A to 2C.

The seal body 100 is supported by a frame 112. In some configurations, the inlet opening of the seal body is fitted to the frame. In some configurations, the inlet opening of the seal body is fitted directly to a conduit extending through the frame.

The frame 112 is preferably a minimal design to provide little visual obstructions, allowing a clear field of view and which allows the user to wear glasses while wearing the interface. Preferably, the frame is formed from an elastomeric material. This allows the frame to flex to conform slightly to the user's face, while still providing support for the seal body to keep the seal effectively against the face and around the nose of the user.

The frame may be formed by injection moulding, preferably from an elastomeric material such as silicone or polyurethane, for example but without limitation. However, more rigid materials may be used.

The illustrated frame presses the inflated seal body against the face of the user out to the periphery of the frame. For example, a nasal bridge of the frame may press the uppermost periphery 200 of the compressed seal against the bridge 216 of the nose of the user. Side peripheral portions of the frame press side peripheral portions of the seal body against the lower cheeks of the user.

The illustrated frame includes connection points for connecting straps 126 to the frame. The strap attachment points provide for anchoring the straps, and preferably for adjusting the strap lengths.

In other forms, the envelope may include integral strap attachment points. These attachments may be points on the surface of the envelope. However, they could be integral straps or wings formed in the envelope that extend out either side of the envelope. The strap attachment points are similar to those shown in FIG. 1A or 1B and/or described above but are formed on the envelope.

The interface can be supported by a single strap 128 passing around the back of the head. To improve stability of the frame on the face, the straps 126 can be bifurcated at the forward ends of a strap 128. Each end of the strap 128 divides at a clip 134 into an upper strap 130 and a lower strap 132. The straps may be formed from an elastic or elastomeric material. For example, suitable strap materials may include a woven elastic strip or a narrow strip of foam and fabric, such as Breathoprene™, for example but without limitation. The strap extending around the back of the head provides pressure on the mask and helps seal the envelope to the user's face.

The connection points on the frame may include lower connection points 122 for receiving ends of the lower strap 132 and upper connection points 120 for receiving the ends of the upper strap 130. The connection between the frame 112 and the straps may be by any suitable buckle, strap bar or clip, for example but without limitation. In the illustrated embodiment the connection points are provided close to the extreme side limits of the frame.

In the illustrated embodiment of FIGS. 1A and 1B, the frame 112 includes laterally extended supporting arms 124 that can press on the lower cheek portions 214 of the user, possibly outside the periphery of the seal body. The side arms 124 preferably are flexible but stiffer than the seal body or straps.

The lower strap connection points are preferably provided at the extreme ends of the supporting arms.

The support arms may be provided with some cushioning on their inside surface to contact the user's face. The cushioning could be formed from silicone or from a foam material, for example but without limitation.

A web 218 of elastic material may span between the flexible support arms 214 and the upper connection points 122. The web 218 provides support to the inflated envelope, pushing it against the face to create a mobile seal in the side peripheral region. The web may be thin relative to the rest of the mask frame.

A flexible tube 114 extends from the frame 112. The flexible tube delivers breathable gas. The distal end of the flexible tube 114 connects to a main CPAP delivery tube 212, for example, at a connector 210. The flexible tube 114 is preferably made of breathable material such as that tube constructions described in U.S. Pat. No. 6,769,431 and U.S. Pat. No. 7,140,366, except the tube 114 is an inspiratory conduit not an expiratory limb. The contents of each of U.S. Pat. No. 6,769,431 and U.S. Pat. No. 7,140,366 are incorporated herein by reference in its entirety.

A lanyard 204 may be connected to the distal end of the flexible tube 114, the connector 210 or the delivery tube 212. The lanyard is to be connected to the body of the user of the interface. For example, the lanyard may be worn around the neck 206 of the user. The lanyard carries the weight of the main delivery tube allowing less pressure to hold the interface in place. This may allow a single head strap to hold the interface in place.

The lanyard may connect to the conduit, for example, by a clip 208 that clips into a corrugation of the conduit. Preferably, the lanyard or tether is connected to the conduit at a location between 10 cm and 50 cm from the frame.

A connector 116 may connect the tube and the frame. The connection mechanism may be any suitable connection. For example but without limitation, this could include a snap fit, hooks in to the silicone, keyhole inserts, over moulding, insert moulding, screw attachments or gluing, or any combination.

The connector 116 may include a limited flow outlet (or bias flow outlet) 220 for providing gas washout from the interface. The outlet 220 may be in the form of a collection of small apertures in the connector. Internally, the connector may include a funnel or extension leading from the vent into the mouth of the envelope.

The frame may have any suitable arrangement for securing the envelope. An example is an annular wall extending from the inside of the frame around the perimeter of an opening that extends to the connector 116. The wall includes an outwardly extending lip. The inlet opening of the envelope engages over the outwardly extending lip of the wall. The inlet opening of the envelope is preferably is stretched to fit over the lip. The inlet opening of the envelope may be provided with a thickened or reinforced wall section, for example by rolling up an extended section of the envelope.

Alternatively, the envelope may be fitted with one part of a connector (for example but without limitation, by adhesive or over moulding) and the frame or the end of the conduit may include a complimentary connector portion.

The frame could be varied substantially and still provide suitable support for the inflatable envelope. The frame could include fewer or additional supporting arms against the face. The frame could incorporate rigid bodies to provide better support. The frame could incorporate a swivel or ball joint for the flexible conduit to allow rotation through different angles and orientations. The frame could include mechanisms to adjust size or shape or both to different users. The frame could support more than one inflatable envelope.

The interface could include more straps to provide support around the user's head. The frame and straps could be moulded from a continuous body of elastomeric material.

Figure 1C:
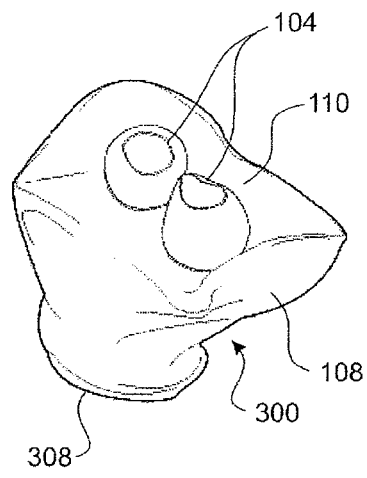
FIG. 1CA to 1CD are a sequence of illustrations showing inflation of the inflatable envelope.
Figure 1C:
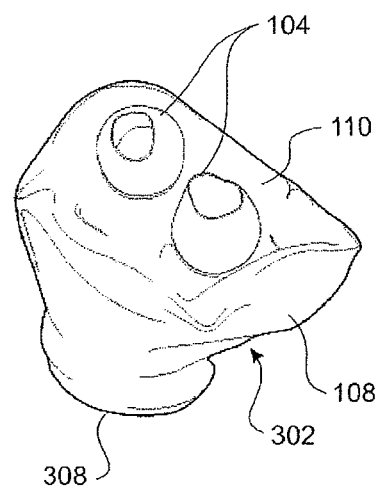
Figure 1C:
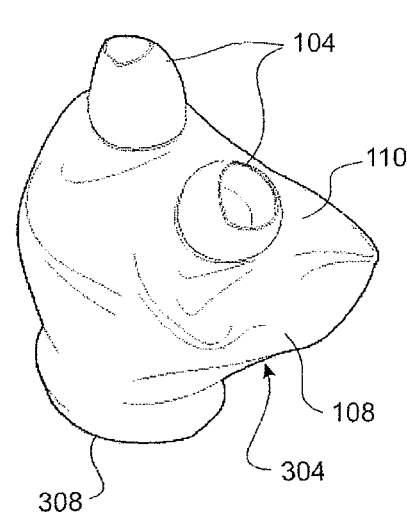
Figure 1C:
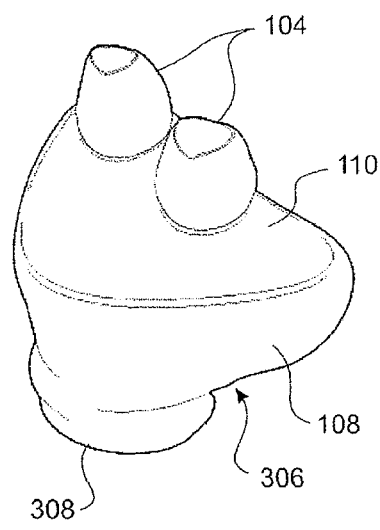

FIGS. 1CA to 1CD are a sequence of illustrations showing inflation of the inflatable envelope.

FIG. 1CA shows the seal 300 limp and deflated. The side wall and seal portion of the seal body are collapsed toward the inlet perimeter 308.

FIG. 1CB shows the envelope 302 slightly inflated.

FIG. 1CC shows the envelope 304 further inflated.

FIG. 1CD shows the envelope 306 inflated to substantially the final form in which the internal pressure supports the shape against the effect of gravity. This shows the nostril locators 104 protruding and aligned, ready for positioning in the user's nostrils as the first step in donning the interface.

When inflated without stretch the envelope desirably will not pass through a circular aperture having a diameter of about 40 mm without contact.

When the envelope is inflated it holds its shape with an internal pressure equivalent to about 3 cm $H_2O$.

The next stage in donning the interface is to press the frame toward the face to compress the seal body around the region of the nose. The user then passes the strap over their head to hold the frame in place, pressing against the seal body.

In use, the frame may move relative to the head of the user. This may result from movements of the user during sleep, from changing the shape of their face, from changing the orientation of (and therefore gravity effects on) the interface, from forces on the conduit connected to the interface causing tugging at the frame, or from forces directly applied to the frame or straps.

FIGS. 1DA to 1DC show how the envelope retains a seal despite substantial vertical movement of the frame relative to the head. The wall thickness of the seal body is exaggerated for clarity. The seal is retained by the seal body conforming to the user's face to retain a sealing area. The seal body conforms to the user's face due at least in part to the suppleness and extent of the envelope. In addition, the seal body conforms to the user's face due at least in part to the treatment pressure inside the seal body pressing the seal body against the facial contours.

FIG. 1DA shows a desired position 402 of the seal body relative to the user's face. The position and orientation of the frame (which is not shown) is indicated by the inlet 400 of the seal body. The upper seal portion 424 of the seal body is wrapped around the tip of the nose 418. The lower seal portion 422 of the seal body is pressed against the upper lip of the user.

FIG. 1DB shows a less desired position 404 of the seal body relative to the user that might occur if the frame was moved upward as indicated by arrow 408. The more desired position 402 is shown in ghost for comparison. The upper wall seal and the wall portion 428 have rolled upward. The seal now extends to a higher location 416 on end of the nose. The lower wall seal portion 426 has pealed somewhat away from the upper lip of the user, but abundant supple material still maintains a seal just below the nose at 414.

FIG. 1DC shows a less desired position 406 of the seal body relative to the user that might occur if the frame was moved downward as indicated by arrow 410. The more desired position 402 is shown in ghost for comparison. The upper seal portion 432 has rolled upward, pealing way from the tip of the nose, but the abundant supple material still maintains a seal at 420. The lower wall seal portion 430 now covers the upper lip and maintains a seal at 412.

Figure 1E:
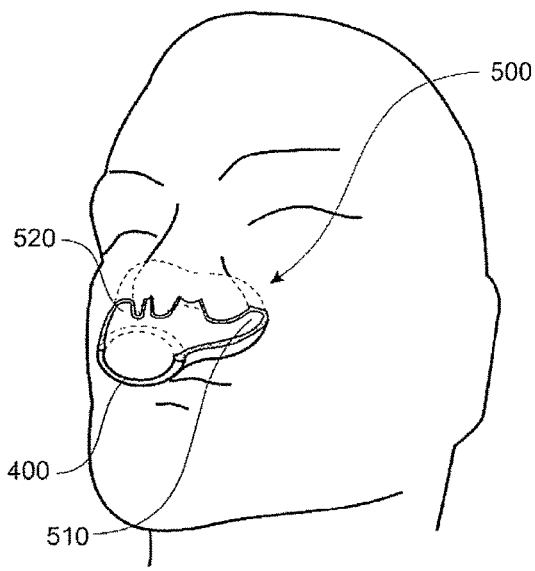
FIGS. 1EA to 1EC show how the envelope retains a seal despite substantial lateral movement.
Figure 1E:
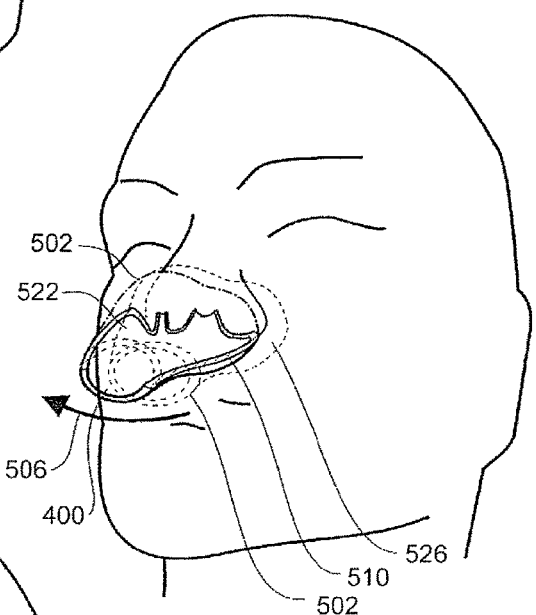
Figure 1E:
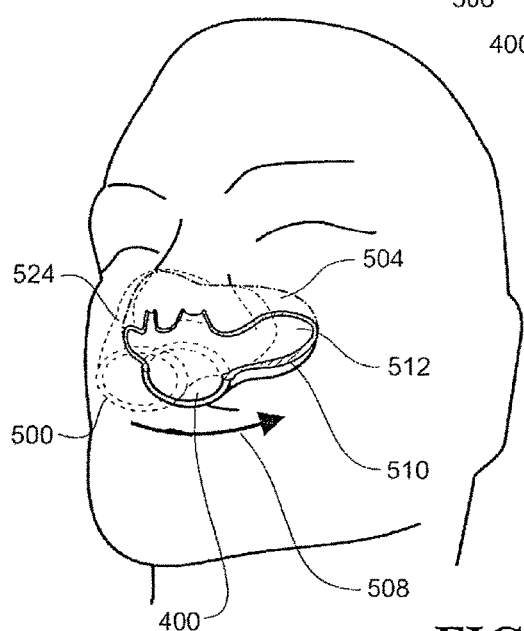
Figure 1F:
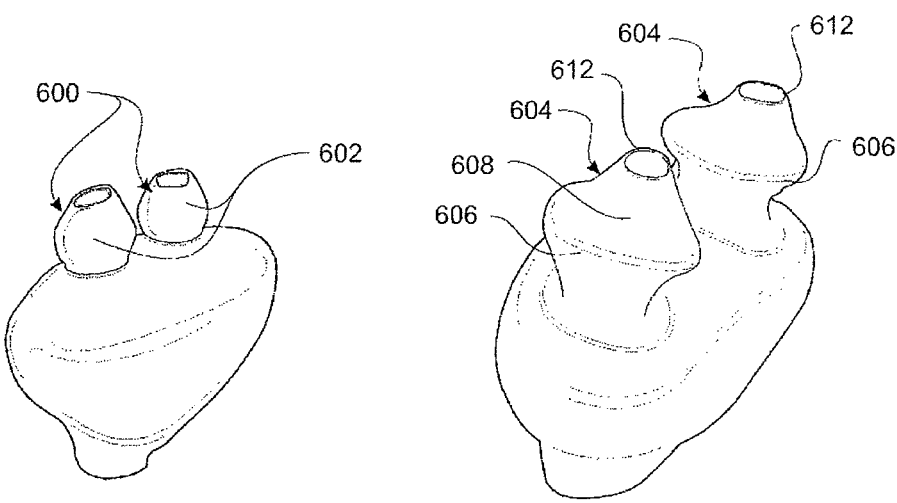
FIGS. 1FA to 1FE show views of a number of interface variations. The interface variations include variation of the shape of the envelope and the shape of the nasal locators.
Figure 1F:
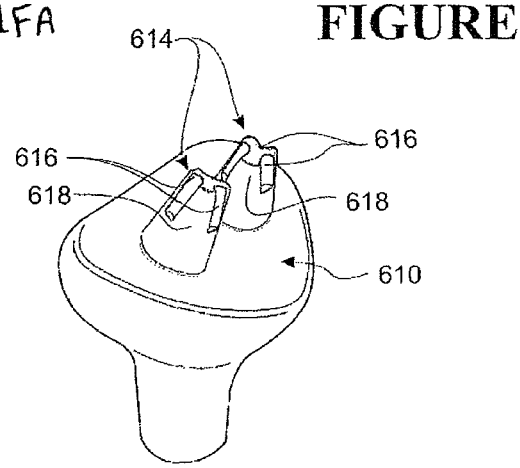
Figure 1F:
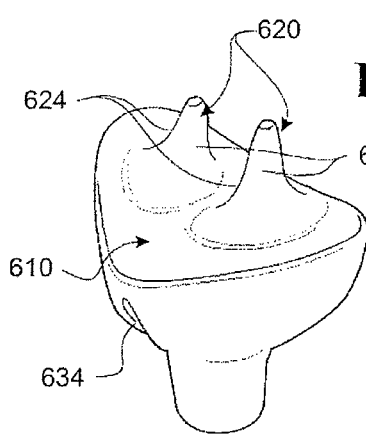
Figure 1F:
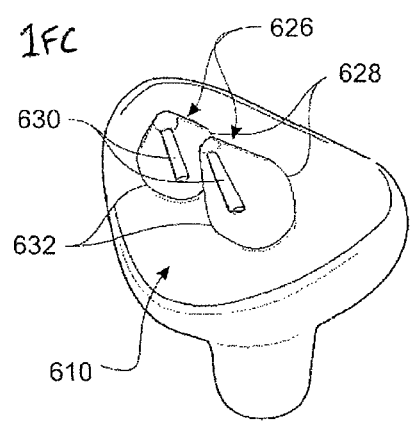
Figure 1G:
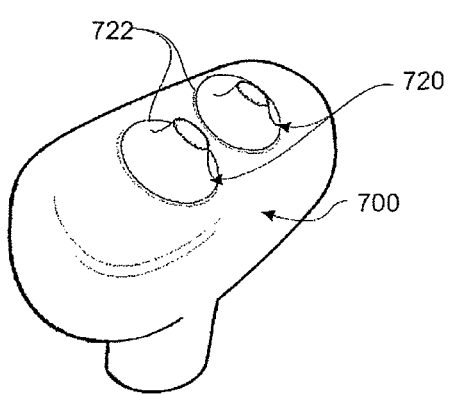
FIGS. 1GA to 1GE show views of a number of interface variations. The interface variations include variation of the shape of the envelope and the shape of the nasal locators.
Figure 1G:
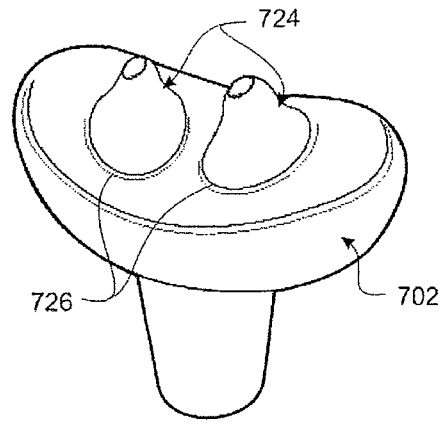
Figure 1G:
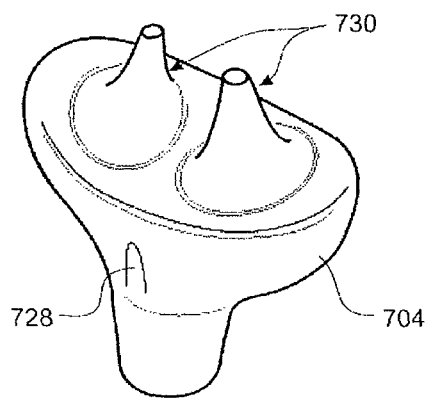
Figure 1G:
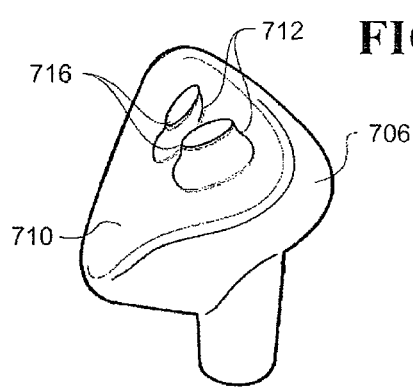
Figure 1G:
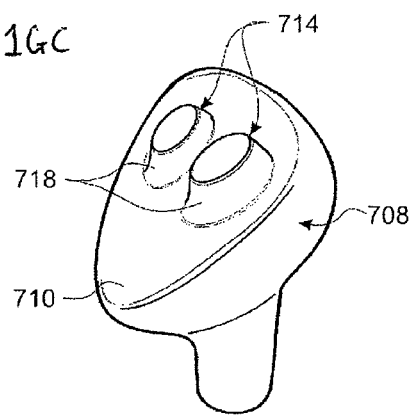
Figure 1H:
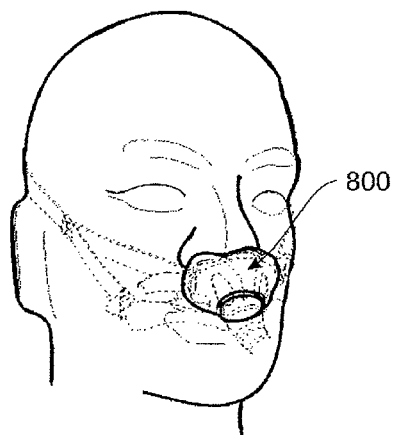
FIGS. 1HA to 1HG show views of a number of interface variations. The interface variations include variation of the shape of the envelope, which are illustrated relative to features of a user's face.
Figure 1H:
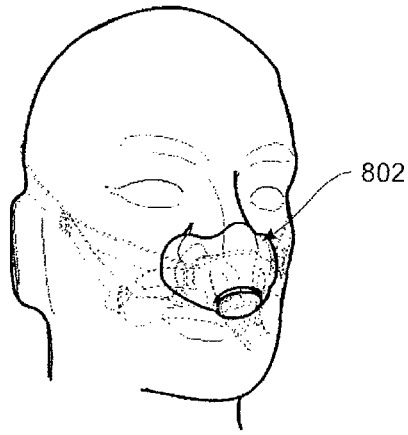
Figure 1H:
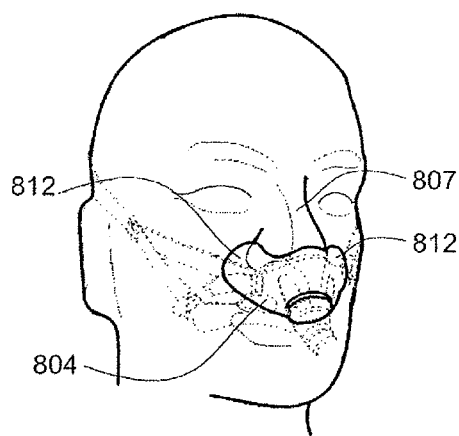
Figure 1H:
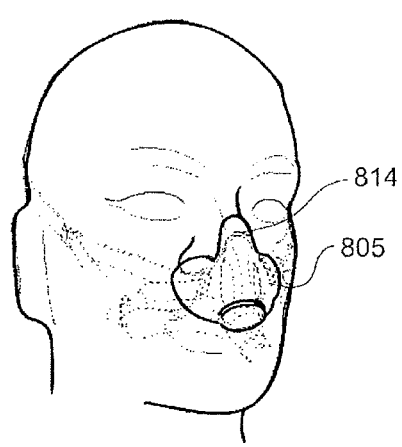
Figure 1H:
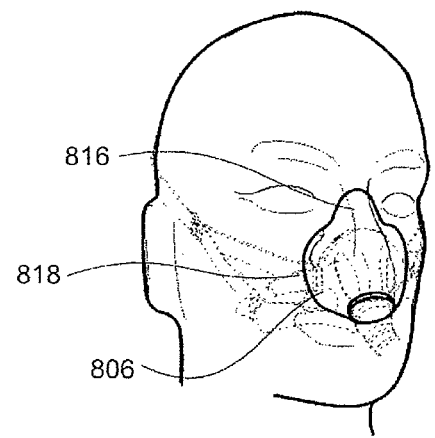
Figure 1H:
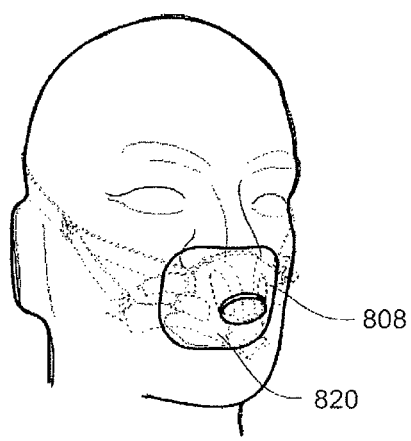
Figure 1H:
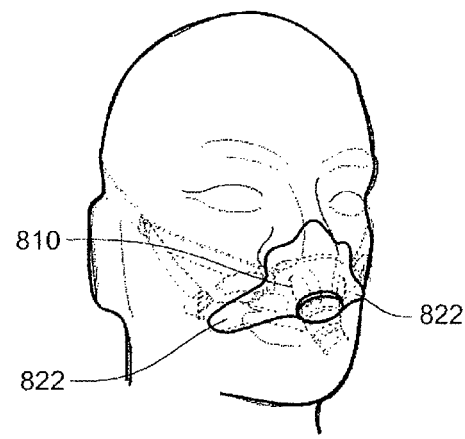

FIGS. 1EA to 1EC show how the envelope retains a seal despite substantial lateral movement of the frame relative to the head. The wall thickness of the seal body is exaggerated for clarity. The seal is retained by the seal body conforming to the user's face to retain a sealing area. The seal body conforms to the user's face due at least in part to the suppleness and extent of the envelope. The seal body also conforms to the user's face due at least in part to the treatment pressure inside the seal body pressing the seal body against the facial contours.

FIG. 1EA shows a desired position 500 of the seal body relative to the user's face. The position and orientation of the frame (which is not shown) is indicated by the inlet 400 of the seal body. The left and right side seal body portions 510 and 520 respectively cover the cheeks to an equal extent on each side of the nose.

FIG. 1EB shows a less desired position 502 that might occur if the frame was moved to the user's right, as indicated by arrow 506. The left side portion 510 of the seal has peeled away from the face at region 526 but still retains a seal in the region of the nares. The right side portion of the seal has rolled out to cover additional area 522 of the right cheek of the user.

FIG. 1EC shows a less desired position 504 that might occur if the frame was moved to the user's left, as indicated by arrow 508. The right side portion of the seal has peeled away from the face at region 524, but still retains a seal in the region of the nares. The left side portion 510 of the seal has rolled out to cover additional area 512 of the left cheek of the user.

One inflating seal arranged and configured in accordance with certain features, aspects and advantages of an embodiment of the present invention has been particularly described above. A number of variations, which variations are by no means the limit of variation, are illustrated in FIGS. 1E to 1H. These variations display a number of individual features that may be selected and combined in many combinations. The combinations illustrated are selected only for exemplification and other combinations are also possible.

FIGS. 1FA to 1FE show views of a number of interface variations. The interface variations include variation of the shape of the envelope and the shape of the nasal locators.

The seal body of FIG. 1FA includes nasal locators that are shaped to locate in the nares. The locators 600 include a bulge 602 between where they join the envelope and their outlet ends. The bulge helps secure the locators within the nares on inflation with internal air pressure. The narrower base where they join the envelope increases flexibility.

The seal body of FIG. 1FB includes nasal locators that are shaped to locate against the nares. The locators 604 include a flange between where they join the envelope and their outlet ends. The flange is broader than the nares opening and presses against the lower surfaces of the nose. The flange is pressed against the nares by inflation with internal air pressure. The narrower base where they join the envelope increases flexibility. The narrower tip portion 608 locates inside the nares to locate the seal body.

The seal body of FIG. 1FC includes nasal locators 614 that are shaped to locate in the nares. The locators 614 include an alternating series of gussets 616 and ridges 618 adjacent their outlet ends. The gussets assist the locators to expand on inflation with internal air pressure.

The seal body of FIG. 1FD includes nasal locators that are shaped to locate in the nares. The locators 620 have a wide base 624 adjacent the envelope and taper to a narrow tip 622.

The narrow tip allows for an easy fit into the nares. The flared base portion 624 provides a comfortable transition to seal in the nares.

The seal body of FIG. 1FD also illustrates the possibility of providing one or more areas 634 of the envelope shaped to deform in a controlled manner when the seal is compressed against the user's face by the frame. Preferably these areas deform in a predictable way that assists the seal to maintain seal as the frame moves relative to the face.

The seal body of FIG. 1FE includes nasal locators that are shaped to locate in the nares. The locators 626 include a bulge 628 between where they join the envelope and their outlet ends. The bulge helps secure the locators within the nares on inflation with internal air pressure. The narrower base 632 where they join the envelope increases flexibility. The locators 626 also include one or more gussets 630 to assist the locators to expand when inside the nostrils.

The seal bodies of FIGS. 1FC to 1FD have a substantially triangular seal surface 610 to increase the amount of supple seal material available to cover the user's nose. The seal bodies of FIGS. 1FA to 1FB have a more oblong or oval shaped seal surface.

FIGS. 1GA to 1GE show views of a number of interface variations. The interface variations include variation of the shape of the envelope and the shape of the nasal locators.

The seal body 700 of FIG. 1GA includes nasal locators that are shaped to locate in and against the nares. The locators 720 have a wide flange 722 adjacent the envelope and taper to a narrower tip. The tip fits into the nares. The flared portion 722 presses against the lower surfaces of the nose. The nasal locator may have a short stalk recessed inside the envelope. The stalk provides flexibility.

The seal body 702 of FIG. 1GB includes nasal locators that are shaped to locate in and against the nares. The locators 724 have a wide flange 726 adjacent the envelope and taper to a narrower tip. The tip of locator 724 is narrower than the tip of locator 720 of FIG. 1GA. The narrow tip fits into the nares. The flared portion 724 presses against the lower surfaces of the nose. The nasal locator may have a short stalk recessed inside the envelope. The stalk provides flexibility.

The seal body 704 of FIG. 1GC is like the seal body of FIG. 1FD except for an ovoid form rather than a triangular form. The locators 730 have a wide base adjacent the envelope and taper to a narrow tip. The narrow tip allows for an easy fit into the nares. The flared base portion provides a comfortable transition to seal in the nares.

The seal body 706 of FIG. 1GD includes nasal locators that are shaped to locate in the nares. The locators 712 are gently flared to their base. The locators 712 have oval outlet apertures 716, which match the typical anatomic shape of the nostril entrance. The ovals may be angled relative to each other. The flared base portion may be steeper on the inward facing wall than on the outward facing wall.

The seal body 708 of FIG. 1GE is like that of FIG. 1GD. The nasal locators are shaped to locate in the nares. The locators 714 are gently flared to their base. The locators 718 have oval outlet apertures that match the typical anatomic shape of the nostril entrance for a larger nose. The ovals may be angled relative to each other. The flared base portion may be steeper on the inward facing wall than on the outward facing wall.

The seal body of FIG. 1GC also illustrates the possibility of providing one or more areas 728 of the envelope shaped to deform in a controlled manner when the seal is compressed against the user's face by the frame. Preferably, these areas deform in a predictable way that assists the seal to maintain seal as the frame moves relative to the face.

The seal bodies of FIGS. 1GD and 1GE have a substantially triangular seal surface 710 to increase the amount of supple seal material available to cover the user's nose. The seal bodies of FIGS. 1GA to 1GC have a more oblong or oval shaped seal surface.

FIGS. 1HA to 1HG show views of a number of interface variations. The interface variations include variation of the shape of the envelope, which are illustrated relative to features of a user's face, in the form they would take under compression by the interface frame.

The envelope 800 of FIG. 1HA is shaped to have a smaller overall size which seals generally around the bottom of the nose and the nares. The small minimal form still conforms to the user's face due to the CPAP delivery pressure inside the body. However, the limited lateral and vertical extent of the envelope means it will not retain seal through as large of a displacement range as other configurations that are illustrated.

The envelope 802 of FIG. 1HB is shaped to have a larger overall size to encompass more of the area around the nose. The larger extent of the envelope suggests it will retain seal through larger displacements than the seal of FIG. 1HA.

The envelope 804 of FIG. 1HC is shaped to have a larger lateral size to accommodate users with wider noses and to provide more lateral support. The larger lateral extent 812 of the envelope suggests it will retain the seal through larger lateral displacements than the seal of FIG. 1HA. Also, the lack of seal over the user's nasal bridge 807 means there is very limited or no pressure on the user's bridge, thereby increasing the user's comfort in that area.

The envelope 805 of FIG. 1HD is shaped to be more upwardly extended with a definite protruding portion 814. The protruding portion 814 wraps over the nose tip and around the sides of the nose to accommodate longer noses.

The envelope 806 of FIG. 1HE is sized to encompass the whole nose having more vertical extent 816 and more lateral extent 818 than the envelope of FIG. 1HA. This envelope may be used with a larger and more extensive frame to provide a wider seal.

The envelope 808 of FIG. 1HF includes a downwardly extending portion 820 that covers the mouth of the user. This downward extension may include an oral interface portion for supplying therapy orally as well as, or instead of, nasally.

The envelope 810 of FIG. 1HG includes wing portions 822 that exemplify the possibility that the seal body could provide cushioning under extended parts of the frame. For example, the wing portions could provide cushioning under the support members 124 of the frame of FIG. 1A.

The described and/or illustrated variations of envelope shape and nostril locating members are provided for the purpose of illustrating a number of possibilities that could be applied to the inflatable seal. The inflatable seal concept is intended to encompass these and other variations.

FIG. 1I shows a further alternative embodiment of an interface. The interface 900 has a seal body and a supple envelope 901 having any suitable configuration, including a configuration such as any described above.

The envelope 901 is supported by a frame. The illustrated frame 902 cups about the envelope 901. Extending above the frame 902 and the envelope 901 is a strap. The strap 903 further stabilises the envelope 901. Preferably, the strap reduces the likelihood of the envelope extending out too far from the user's face and helps the envelope to be pushed against the user's face and more particularly the user's nose. The strap can be made from a flexible material similar to that of the frame but can be made with any desired stiffness. Therefore, a more stiff material could be used or a substantially more flexible material can be used relative to the material used for the frame.

The illustrated frame has bias flow holes 904 formed about a connector for the conduit, which conduit provides gases to the interface. The bias flow holes 904 provide gas washout from the interface.

A single head strap 905 extends about the user's head in use. The head strap 905 attaches on either side of the user's head to connectors 906, 907 formed in the frame. The connectors 906, 907 are formed in laterally extending support arms 908, 909 of the frame.

In other forms the strap 903 may be formed in the envelope 901. In this form, the strap is integrally formed in the envelope and provides additional stability to the envelope. Therefore, the integral strap effectively forms an elongate strip in the envelope, wherein the strip extends in an arc above the frame.

Figure 2A:
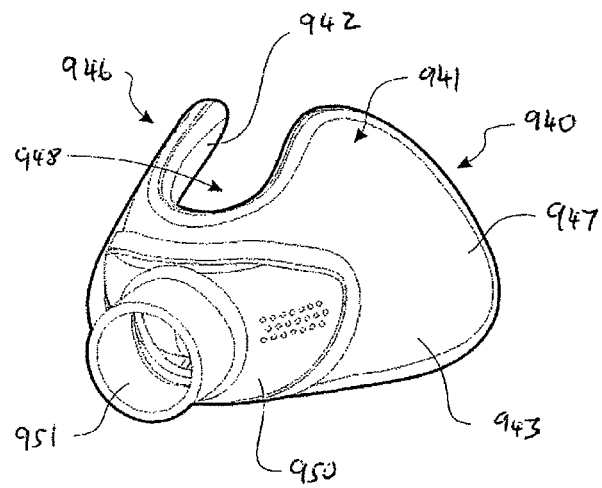
FIGS. 2A and 2B show views of a further embodiment of an interface with an inflatable envelope and frame. The envelope is shaped to wrap around the user's nose in use.
Figure 2B:
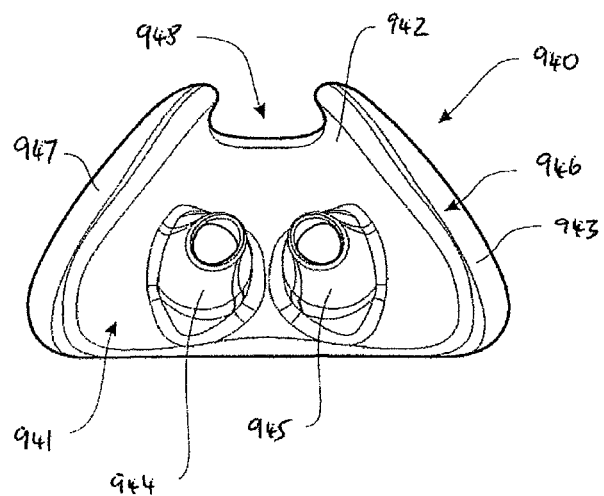
Figure 2C:
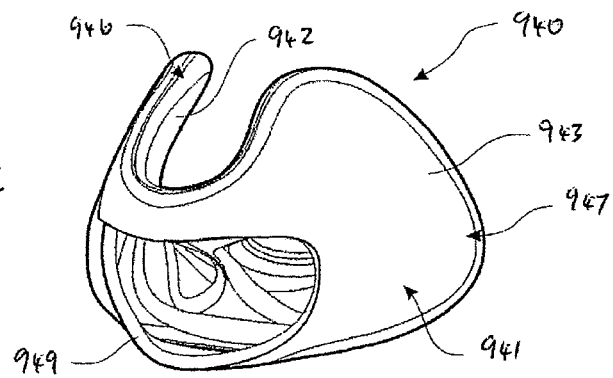
FIG. 2C shows the envelope of FIGS. 2A and 2B with the frame removed.

FIGS. 2A to 2C show a further example of an interface with an inflatable envelope, bag or balloon. The interface includes a seal body 940. The seal body 940 includes a supple envelope 941. The seal body 940 has a curved shape that preferably is configured to substantially match the contours of a human face. The illustrated seal body 940 has an inner surface 942 and an outer surface 943. The inner surface 942 includes nostril locators 944, 945. The nostril locators 944, 945 each have outlets to allow gases to pass to the user. In use, the inner surface 942 presses against the user's face and the nostril locators 944, 945 extend into or sit about the user's nostrils.

The seal body 940 is shaped to wrap around the user's nose. The seal body 940 has side portions or wings 946, 947 that extend completely or substantially completely over the sides of the user's nose and may also extend at least partially over the user's cheeks. The seal body 940 is missing in the region of the user's nasal bridge. Accordingly, it can be said that there is a cut out region 948 in the seal body. The cut out region 948 means the seal body, when in use, does not put direct pressure on the user's nasal bridge region, a common area of complaint by users of interfaces that extend over a user's nasal bridge.

The illustrated seal body 940 includes an inlet opening 949. The inlet opening 949 is opposite the nostril locators and receives a frame 950. The illustrated frame 950 is curved to match the seal body and provides support to the seal body. The frame 950 includes a connector 951 that attaches in use to the tubing (for example tubing 114 as shown in FIGS. 1A and 1B) that receives pressurised gases to supply to the user.

The frame 950 is made from a plastics material. The plastics material may be a flexible material or maybe a more rigid type material, for example but without limitation. For example but without limitation, the frame may be made from a polycarbonate or the frame could be made from a more flexible material, such as silicone.

In use, the interface of FIGS. 2A to 2C is supplied with pressurised gases via tubing and the connector 951 on the frame 950. The gases inflate the seal body 940 and cause it to press against and about the user's nose. The nostril locators 944, 945 are caused to seal in or about the user's nostrils and the pressurised gases pass through the locator outlets into the user's nostrils.

The illustrated frame or seal body includes at least two strap connectors similar to those described above. The connectors allow a head strap to be attached to the interface 940. The head strap will extend about the back of the user's head and provide additional tension on the interface to help seal the interface against the user's face.

The seal body can be made from a flexible material. Nonlimiting examples of possible materials include latex, vinyl, silicone and polyurethane. In a preferred form, the seal body's outer surface is made from a thicker material than the inner surface. In this way the seal body has a better ability to hold a predetermined shape.

Figure 65:
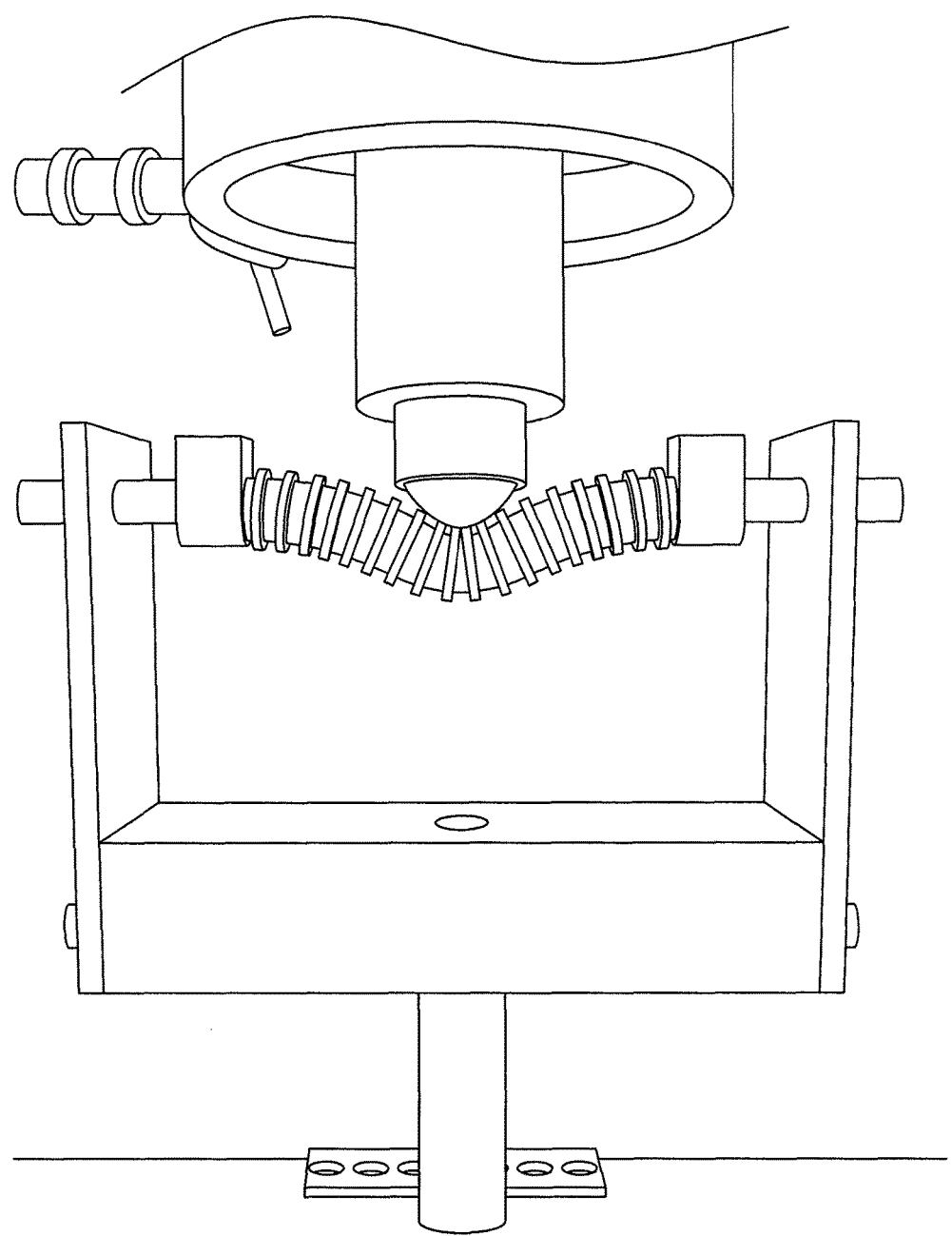
FIG. 65 is a diagram illustrating a test apparatus for measuring the flexibility of a breathing tube.

FIGS. 3 to 65 illustrate interface configurations that include an inflatable nasal seal having a supple wall structure. FIGS. 1 to 2 described above disclose other forms of seals of this type.

The inflatable seal may have a pair of locating protrusions that engage in the nostrils of the user. The locating protrusions supply gases flow to the user from inside the seal. The patient side of the seal may be so supple, and of sufficient dimension and shape, that when the inflated seal is pressed against the face of a user with the locating protrusions engaged in the nostrils of the user, the seal conforms to the surfaces of the user's face (particularly the sides of the nose and the upper lip) and provides a seal. An outwardly facing wall of the seal may be more rigid, and support the inner wall of the seal in a position wrapped around the wearer's nose.

The seal is formed from a material having sufficient elasticity and yield strength that the combination renders the envelope supple. The supple portion is capable of repeated drastic deformations without failure. Possible materials include latex, vinyl, silicone and polyurethane, for example but without limitation. Typical wall thicknesses of the supple portions of the seal would be below about 0.5 mm and could be lower than about 0.2 mm.

The seal body includes a pair of nasal locators protruding from the patient facing wall. Preferably, the nasal locators are formed integral with the seal. Each nasal locator includes an outlet aperture for supplying gas from inside the envelope to a user wearing the interface.

The seal body includes an inlet opening that is approximately opposite the nasal locators.

A substantial extent of the seal body or envelope is supple. A region adjacent and including the nasal locators and a region adjacent and including the inlet opening are much stiffer. These areas hold the overall shape of the seal and can be of any suitable stiffness. These areas may be formed of a stiffer material than, or may be formed thicker in the same material as, the rest of the envelope.

The seal is supported by a mask body or frame. The inlet opening of the seal is fitted to the frame or the inlet opening of the seal can be fitted directly to a conduit extending through the frame.

The frame is preferably a minimal design to provide little visual obstruction, allowing a substantially clear field of view and allowing the user to wear glasses while wearing the interface.

The frame may be formed by injection moulding, for example but without limitation, from an elastomeric material, such as silicone or polyurethane, also for example but without limitation. Alternatively, more rigid materials such as polycarbonate, or polyester, polystyrene or nylon, for example but without limitation, may be used.

The frame can include connection points for connecting straps to the frame. The strap attachment points provide for anchoring the straps.

In other forms, the nasal seal body may include integral strap attachment points. These attachment points may be connection elements on the surface of the envelope. However, the attachment points could be integral straps or wings formed in the envelope that extend out either side of the envelope.

The interface can be supported by a single strap passing around the back of the head. The strap can be formed from an elastic or elastomeric material. For example, suitable strap materials may include a woven elastic strip or a narrow strip of foam and fabric, such as Breathoprene™, for example but without limitation. The strap extending around the back of the head provides pressure on the mask and helps keep the seal against the user's face.

A preferred strap is described later in this specification.

A flexible tube extends from the frame. The flexible tube delivers breathable gas. The distal end of the flexible tube connects to the main CPAP delivery tube.

A connector may connect the tube and the frame. The connection mechanism may be any suitable connection mechanism. For example but without limitation, the connection mechanism could include a snap fit, hooks into the silicone, keyhole inserts, over moulding, insert moulding, screw attachments or gluing, or any combination of these or others.

The connector may include a limited flow outlet (or bias flow outlet) for providing gas washout from the interface. The outlet may be in the form of a collection of small apertures in the connector. Internally, the connector may include a funnel or extension leading from the vent into the mouth of the envelope. Alternatively, the connector may not include a bias flow vent.

Figure 3A:
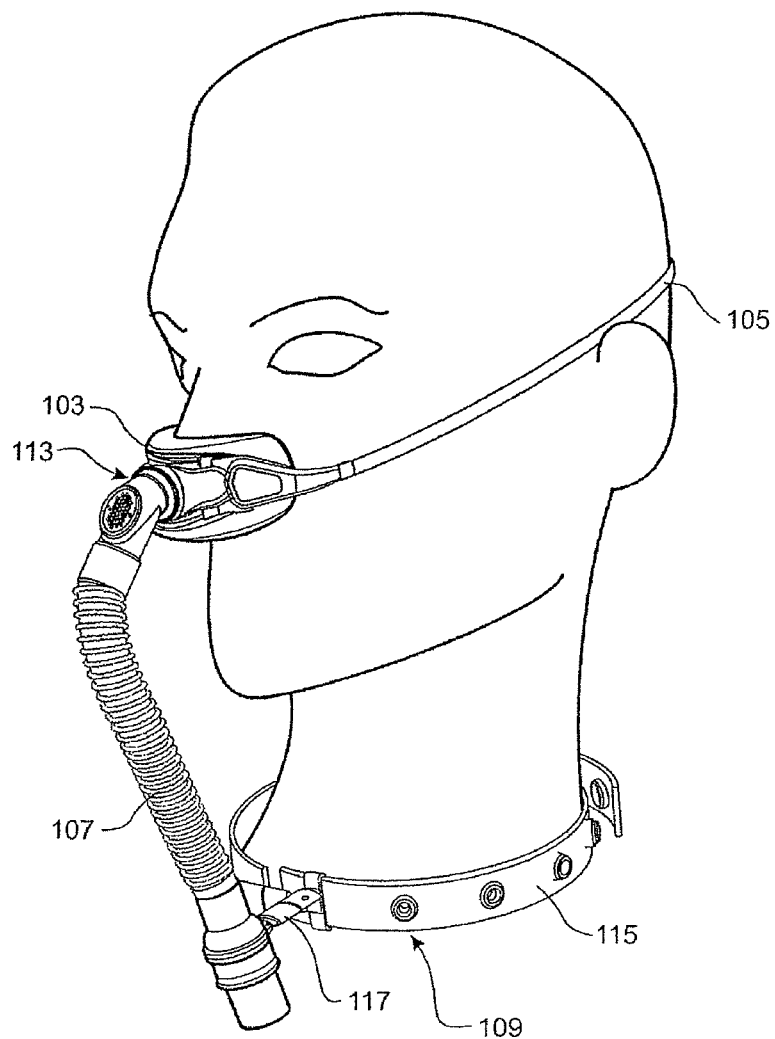
FIG. 3A is a perspective view of a person wearing a patient interface.
Figure 3B:
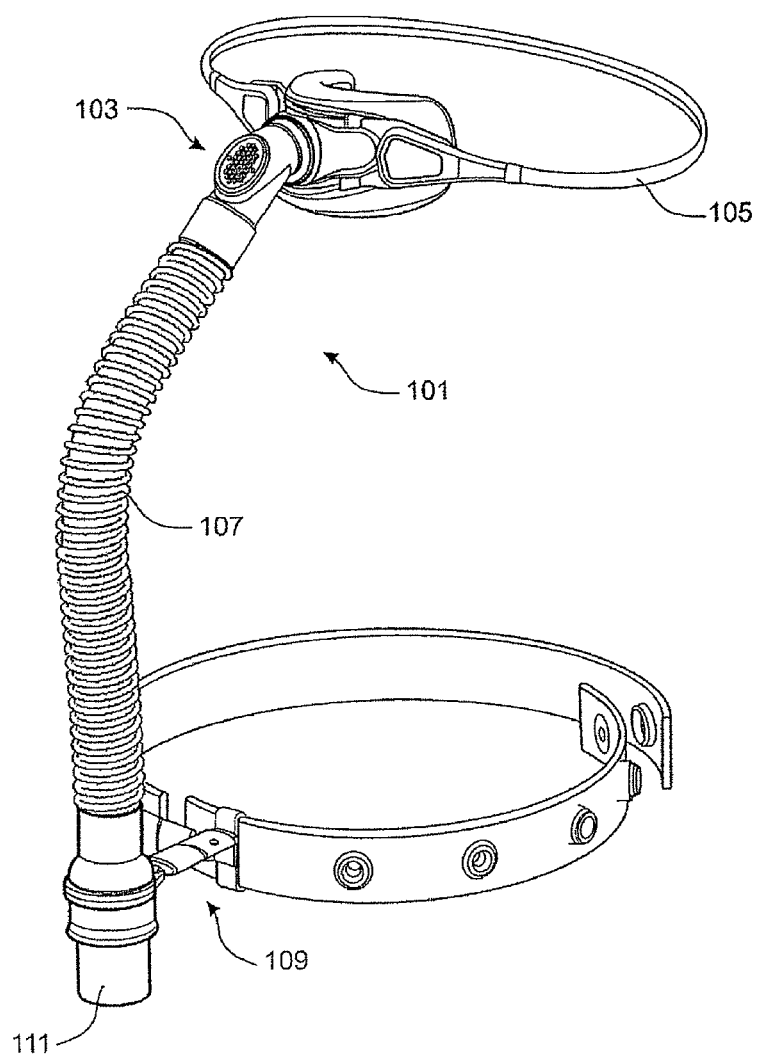
FIG. 3B is a perspective view of the patient interface of FIG. 3A without the patient.

FIGS. 3A and 3B illustrate an example of patient interface embodiment that is arranged and configured in accordance with certain features, aspects and advantages of the present invention. For clarity, the patient interface is shown separate from the patient in FIG. 3B and as worn by a patient in FIG. 3A.

The patient interface 101 broadly includes a mask 103, a strap 104 for securing the mask to the patient, a flexible supply conduit 107 connecting to the mask 103 and a conduit support structure 109 that attaches to a patient and that supports the weight of the conduit portion 107 and of any connected conduit supplying gases to the inlet end 111 of conduit portion 107.

Particular aspects of this patient interface, and variations on each aspect, will be (or have already been) discussed with reference to other Figures. An interface may incorporate some aspects but not other aspects. For example, an interface might incorporate aspects of the mask while using a different arrangement for securing the mask to the user. An interface might include a different mask while using aspects of the strap to secure that mask to the user. An interface may incorporate aspects of the mask but not make use of a similar, or any, structure for supporting the weight of the conduit from the body of the patient. All of these variations are considered within the scope of this application.

Referring to FIG. 3A, the mask 103 fits over the nostrils of the patient and includes lateral portions that curve around either side of the nose. These lateral portions provide form a perimeter seal on the outwardly facing surfaces of the flanks of the nose. The strap 105 passes around the user's head in a simple loop above the user's ears.

The conduit portion 107 depends from a central connection 113 at the front of mask 103. The central connection 113 is preferably a swiveling elbow so that the path of the conduit relative to the positioning of the mask on the face of the patient can adapt to the sleeping position of the patient. The swiveling elbow may be in the form of a ball joint so that the elbow can pivot about axes parallel to and perpendicular to its connection with the mask.

The illustrated conduit support 109 comprises a collar 115 connected around the neck of the user. A tether 117 connects between the collar and the conduit 107.

Figure 3C:
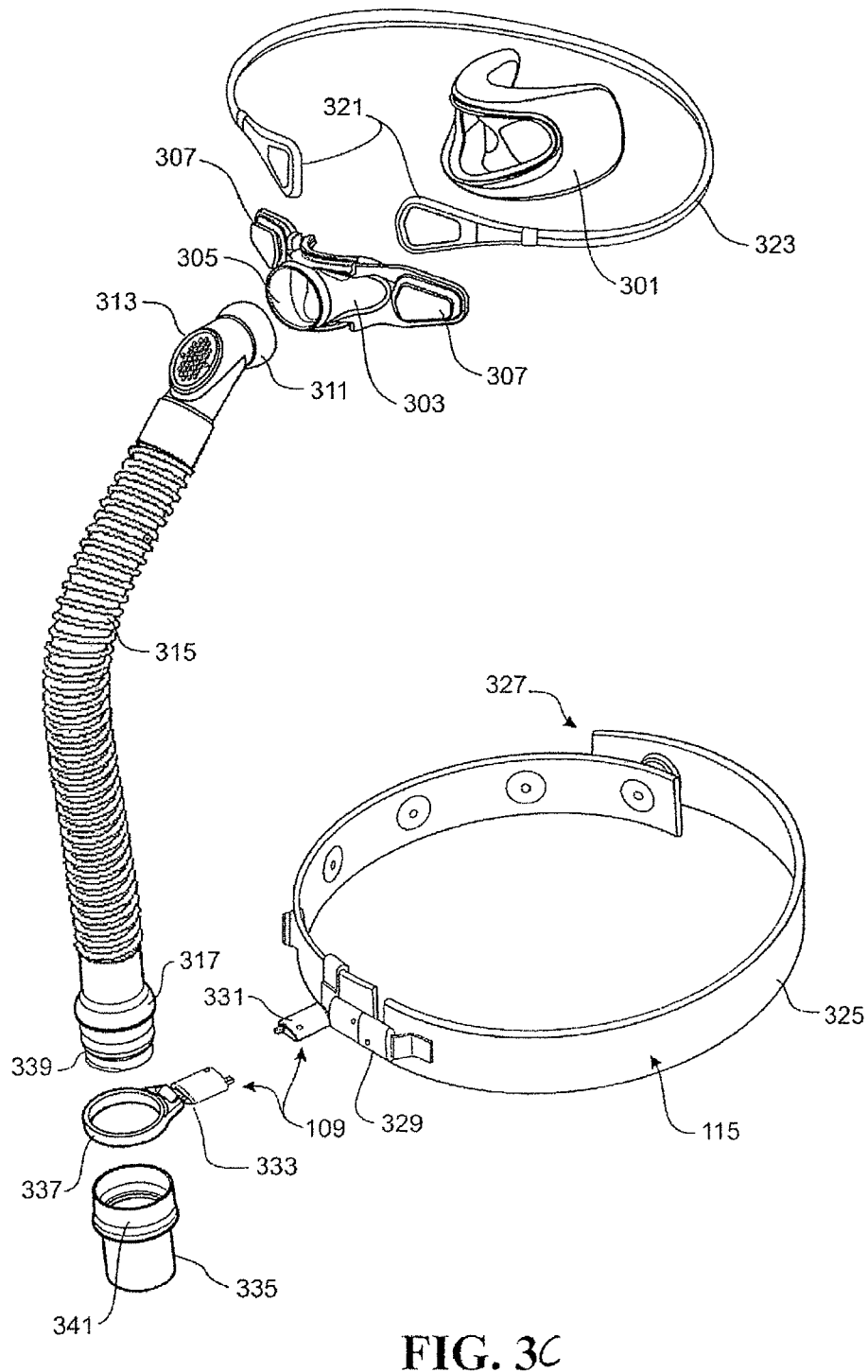
FIG. 3C is an exploded view illustrating several components of the interface of FIG. 3B.

Some of the component parts of this exemplary interface are illustrated in FIG. 3C. The mask 103 generally includes a seal 301 and a body or frame 303. The seal and body are illustrated in more detail in FIG. 5A. Their engagement will be described in more detail with reference to FIG. 5A and FIG. 8.

The body 303 includes a socket 305 and connector portions 307. The socket 305 receives an engagement portion 311 of the elbow 333. The elbow 333 is connected to the end of a length of flexible tubing 315. The other end of flexible tubing 315 is terminated with a cuff 317. The connector portions 307 of the mask body 303 engage with connector portions 321 of the head strap 105. The head strap 105 includes a single length 323 of stretchable material. The connector portions 321 are provided at either end of the length 323.

The collar 115 includes a band 325 of a material intended to be comfortable when worn during periods of sleep. The band includes a first adjustable connection 327 and a second non-adjustable connection 329. At the adjustable connection 327, free ends of the band overlap, and the degree of this overlap may be varied to a desired amount and fixed at this desired amount. At the non-adjustable connection 329, free ends of the band may simply be secured or released. Once the adjustable connection 327 has been adjusted, the collar may be opened for fitting to the patient or removal from the client and secured after fitting to the client, by disconnecting or connecting the non-adjustable connection 329. The non-adjustable connection 329 may be a quick release connector that disconnects with applied tension within a predetermined range. Thus, the collar will quickly and easily release if desired.

The tether 109 includes a first portion 331 attached to the collar and a second portion 333 attached to the conduit. These portions preferably are releasably engaged by another quick release connector, which preferably disconnects with application of a tension within a predetermined range.

The tether portion 333 connects to the conduit 315. The tether portion 333 includes a portion of the quick release connector and a fitting 337 that engages the conduit. The fitting 337 may be an open clip to engage a corrugation of the conduit, to engage a recess of the cuff 317, to engage around the generally cylindrical shape of the conduit, or to engage around a generally cylindrical portion of the cuff. Alternatively, and as illustrated, the portion 337 may comprise a ring that fits around a portion of the conduit or a portion of the cuff. In the illustrated embodiment, the ring 337 is captive between the cuff 317 and a connector portion of a swivel 335. The ring fits over a portion 339 of the cuff 317 and is held captive by an end portion 341 of the swivel 335, which has a larger diameter than the internal diameter of the ring.

Figure 4A:
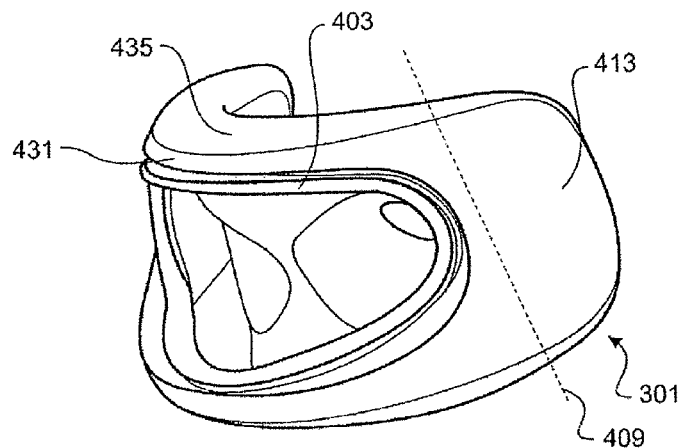
FIGS. 4A to 4C illustrate, from different angles, a seal component of the patient interface of FIG. 3B.
Figure 4B:
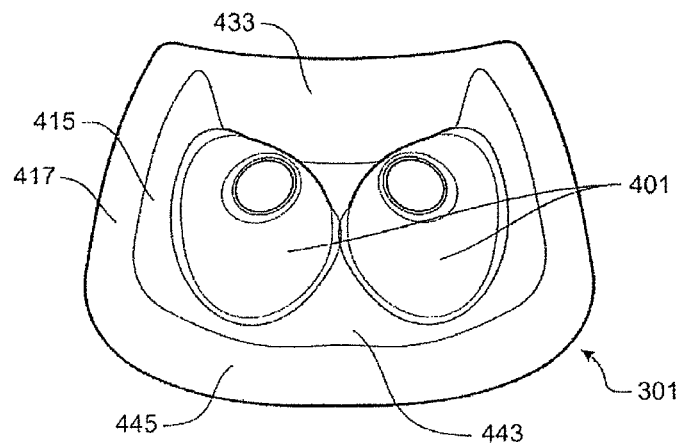
Figure 4C:
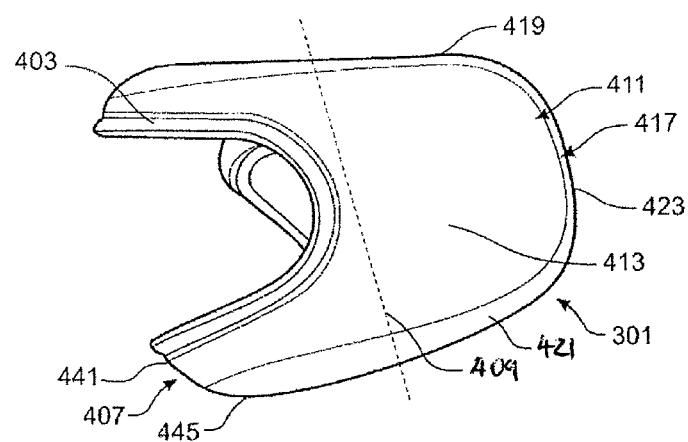

The external form of a seal is illustrated in FIGS. 4A to 4C. The seal 301 includes a patient-facing side, which is broadly illustrated in FIG. 4B, and an outward-facing side, which is broadly illustrated in FIG. 4A. A pair of nasal locators 401 protrude from the patient-facing side. Broadly speaking, the wall of the seal forming the patient-facing side is very supple with the exception of the nasal locators, the area immediately adjacent the nasal locators, or both. Variations in the suppleness will be described in more detail with reference to the cross sections illustrated in FIG. 7D, FIG. 8 and FIGS. 9A and 9B.

In overall form, the seal has a central portion including nasal locators on the patient-facing side and an opening 403 on the outward-facing side. The extent of this central portion 407 is broadly indicated by broken line 409 in FIGS. 4C and 4A. For clarity, broken line 409 is also included in FIG. 7A, which comprises a top view of the mask portion of the interface.

Lateral or side portions 411 extend from the central portion 407. Each side portion includes an outward face 413, an inward face 415 and a peripheral edge portion 417 that joins the inward face portion and the outward face portion. The peripheral edge portion 417 extends around a top edge 419, an end edge 423 and a lower edge 421. Accordingly, considered from inside the seal, the side portions 411 resemble a pocket.

Each side portion is quite extensive. Preferably, the side portion extends greater than about 10 mm (most preferably greater than about 20 mm) or at least a distance of about 70% of the distance separating the centres of the nostril locators 401 beyond the base of each nostril locator.

At least the inside wall 415 and the perimeter wall 417 of each side portion are very supple, so that they can conform to contours of the user's face, and in particular, to contours of the outside of the sides of the user's nose. At least portions of the outside facing wall 413 of the side portion are also supple, but may be progressively less supple moving toward the central portion 407.

The central portion 407 of the seal includes the opening 403 to pass a gases flow to and from the mask body 303. The opening 403 may include features such as lips and/or channels to engage with features such as channels and/or lips on the body 303. The opening 403 may be formed with clip portions, or clip portions may be attached to or overmoulded to the perimeter of the opening 403 to facilitate engagement with the frame 303. Typically, the opening 403 will be substantially thicker and more rigid than the supple sealing portions of the seal 301. The opening 403 can be at least the size of the interior cross section of the supply conduit 315. Preferably, and as illustrated, the opening 403 is generally commensurate with the extent of the body 303 of the mask, this extent being generally commensurate with the general width of the interface and approximately with the width of the nose of the intended wearer.

The interface can be of small size with the body portion 303 of the mask curving to follow approximately the contour of the upper lip of the wearer. The seal can be formed such that the opening 403 follows this approximate curve, in plan view.

The central portion 407 of the seal extends above and below the opening 403. Above the opening 403, and the nostril locators 401, the central portion includes an outward-facing wall 431, an inward-facing wall 433 and a perimeter portion 435. At least the inward-facing wall portion 433 and the outward-facing portion 435 are preferably thin and supple.

Below the opening 403, the central portion 407 includes an outer wall portion 441, an inner wall portion 443 and a peripheral portion 445. At least the inner wall portion 443 and the peripheral portion 445 are preferably thin and supple.

In use, the supple interior wall portions above, below and to each side of the nasal locators are inflated by pressure inside the seal (i.e., inflated from the flow of gases supplied to the patient interface) to press against the skin of the wearer and conform to contours of the outside surfaces of the nose of the wearer, to surfaces of the lower face of the nose of the wearer and to surfaces of the upper lip of the wearer immediately below the nose. Movement of the mask body is not likely to significantly break this seal because the supple perimeter or periphery of the seal allows the mask body to move in the direction of movement to at least a small extent. The supple perimeter decouples the position of the nostril locators from the position of the mask body, which decoupling allows the mask body to displace somewhat in at least one or both of lateral and vertical directions (relative to axes of the patient's face). The side portions 411 engage the sides of the patient's nose and form an additional seal against them. The side portions 411 also support the location of the mask.

Figure 5A:
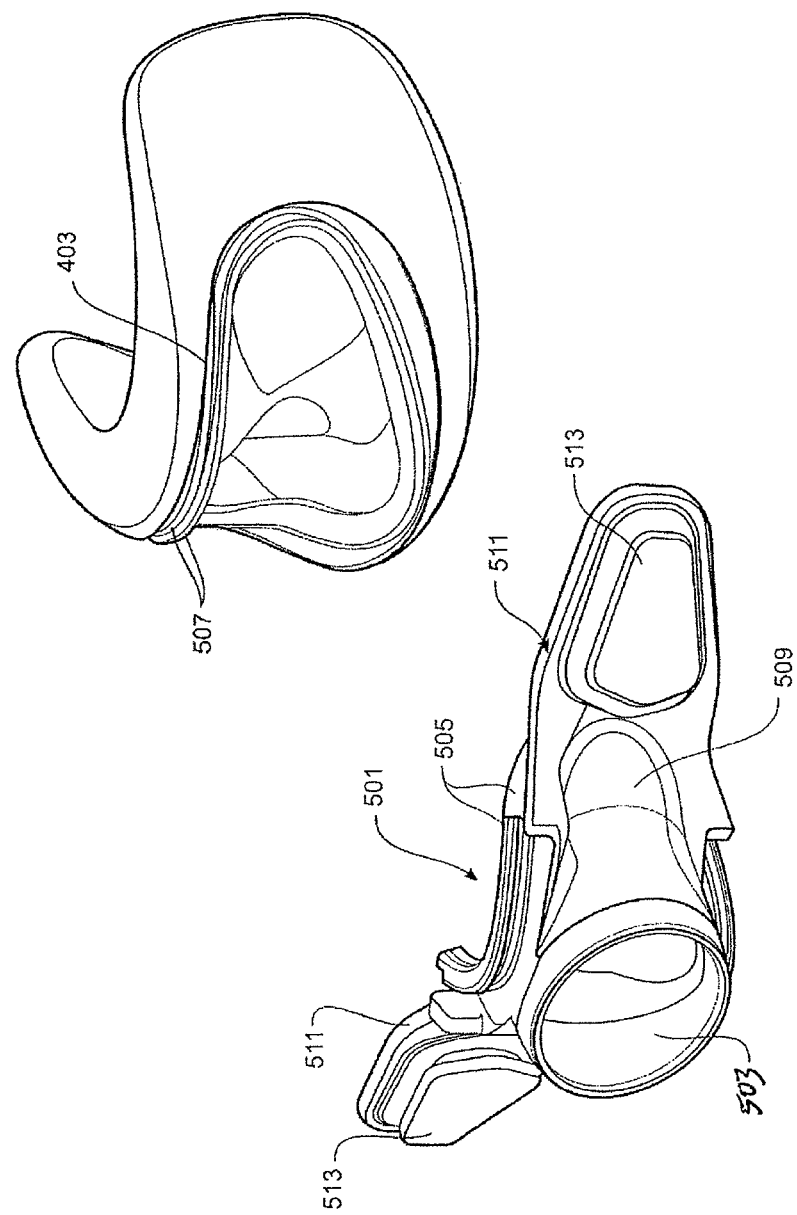
FIG. 5A is an exploded view of the seal and mask frame showing how they can be brought together to be assembled.
Figure 5B:
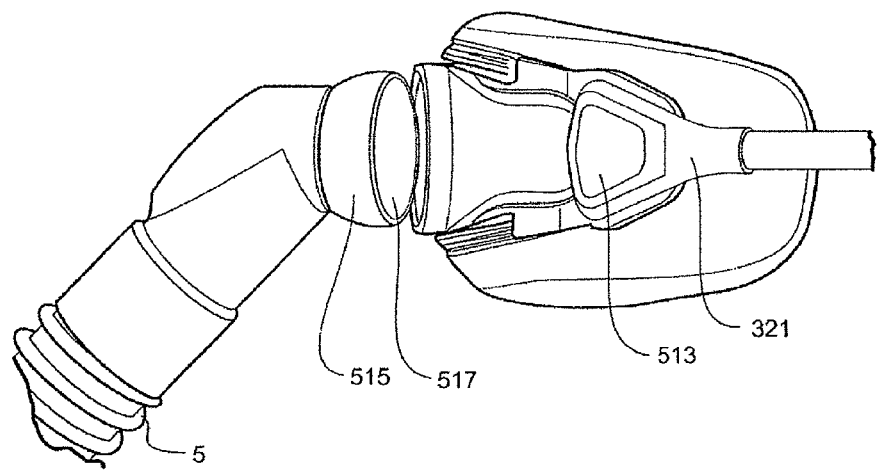
FIG. 5B is a side view of the interface of FIG. 3B, partially disassembled to show the connection of an elbow to the mask frame.
Figure 5C:
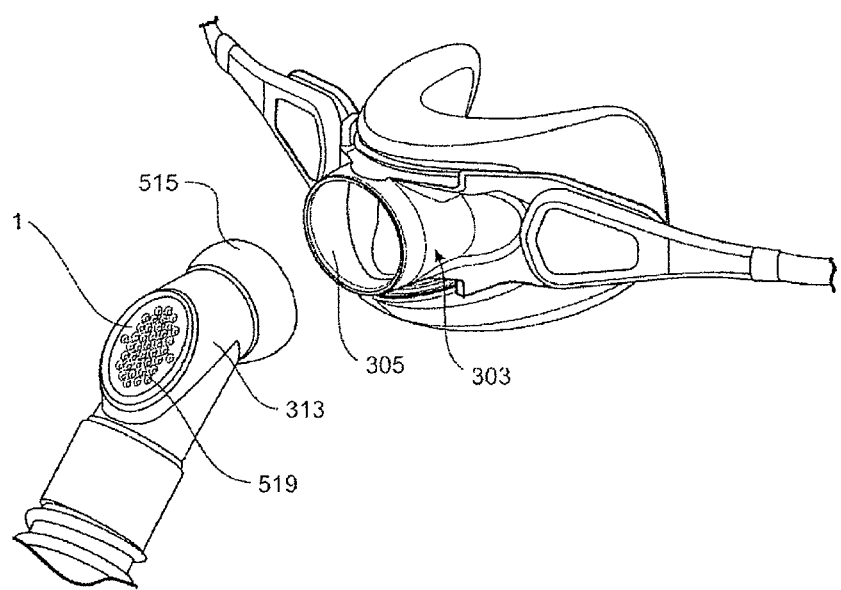
FIG. 5C is a front perspective view of the interface of FIG. 3B illustrating assembly of the elbow with the mask frame, with a gas washout vent present in the elbow.
Figure 6:
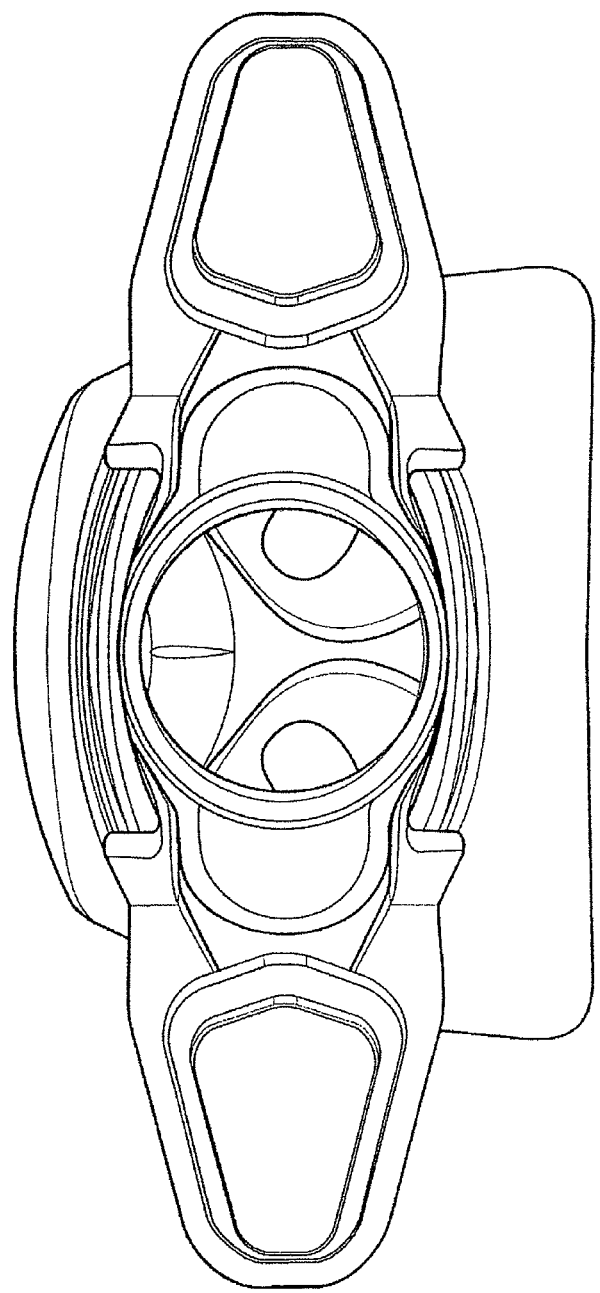
FIG. 6 is a front view of the assembled seal and mask frame.

The mask body and the seal are illustrated in larger format in FIGS. 5A through 5C. As previously described, the seal includes the opening 403 and includes structures that can be used to secure the seal to the mask body. The mask body preferably comprises a socket 503 that is used to connect with the supply conduit. The mask body also comprises a seal opening 501 that engages with the opening 403 of the seal. In the illustrated configuration, the seal opening 501 and the opening 403 of the seal each comprise complementary features that engage the seal and the mask body together. In the illustrated form, the seal opening 403 comprises a connection structure 507 (i.e., lip and channels) and the periphery of the seal opening 501 of the mask body comprises a complementary structure 505 (i.e., channels and lips). The connection structures 505, 507 advantageously define a gasket-like structure. The arrangement of channels and lips reduces the likelihood of leaks at the junction when the seal is properly fitted to the mask body and supplied with gases under pressure. Any other suitable connection structure 507 can be used to connect the seal and the mask body.

In the mask body, the outlet opening 501 to the seal is directly opposite the opening of the socket 503 such that the opening 503 is substantially centrally located. A central side portion 509 extends to either side of the opening 503. The central side portion 509 may be a plain covering wall that encloses a portion of the opening 403 of the seal. In some configurations, the central side portions 509 may include small apertures as part of a gas washout vent.

Figure 7A:
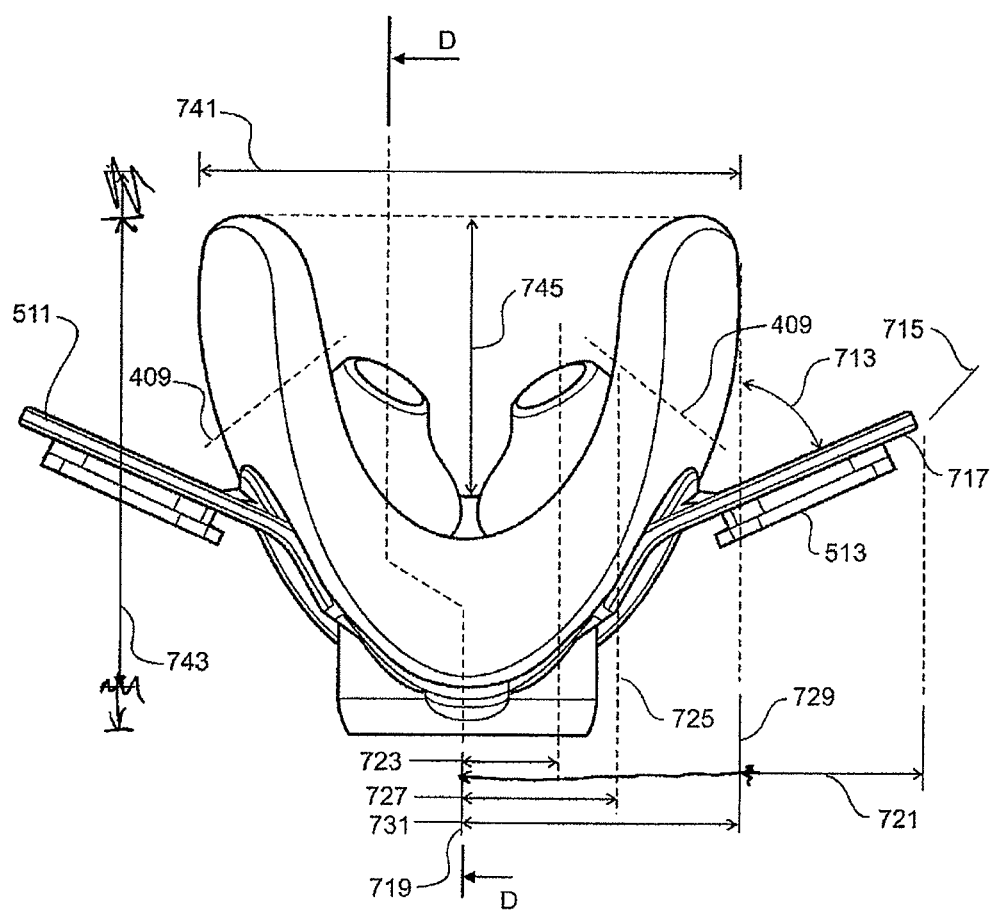
FIG. 7A is a top view of the assembled seal and mask frame.
Figure 7B:
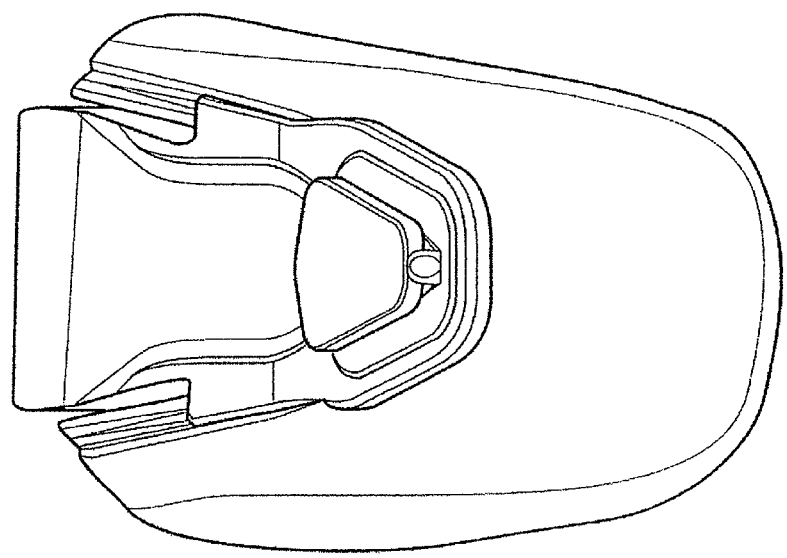
FIG. 7B is a side view of the seal and frame of FIG. 7A, unsectioned.

In the illustrated embodiment, a pair of side arms 511 extend laterally outward beyond the extent of the seal opening 501, as best illustrated in FIG. 7A. The side arms 511 can extend beyond the extreme outer width of the seal. Each side arm 511 comprises a connector portion 513 that is used to connect to the connector portion 321 of the strap. In the illustrated embodiment, the connector portions comprise a securing post with a perimeter undercut. The strap has a small loop formed at each end which stretches over the securing post and engages in the undercut. This connector form is simple and intuitive. Other suitable connector forms also can be used. For example, each side arm 511 can be provided with a portion (e.g., a male part or female part) of a clip with the strap including the mating portion.

As best illustrated in FIG. 7A, the side arms 511 diverge from the outside wall of the seal, for example at an angle 713 of between about 30° and about 80°. A strap secured to the post 513 leaves the side arm in a manner illustrated by line 715 in FIG. 7A. Thus, the strap extends away from the side arms at a location spaced apart from the seal and spaced apart from the face of the wearer. This is better illustrated by the relative locations of the tip 717 of the side arm 511 from the centre line 719 of the interface compared with the seal outermost surface from the centre line 719 of the interface.

The distance 721 from the centre line to the tip of the side arm is preferably between about 25 mm and about 50 mm, and most preferably about 45 mm. This compares with the distance 723 between the centre line 719 and the central axis of the nasal locator, which is preferably between about 5 mm and about 10 mm, and most preferably about 7 mm. It also compares with the approximate location of the inner wall surface of the side portion of the seal, where it leaves the central portion of the seal. This location is illustrated by broken line 725 in FIG. 7A. Preferably this separation 727 is between about 10 mm and about 20 mm, and most preferably about 15 mm. For further comparison, the outermost extent of the side portion is illustrated by broken line 729. The displacement 731 of broken line 729 from centre line 719 is preferably between about 15 mm and about 30 mm, and most preferably about 25 mm.

In the front to back direction, the tips 717 preferably are rearward of the base of the nasal locators such that at least a portion of the bases of the nasal locators are between the central portion of the mask body and a line connecting the tips 717. In some configurations, the entire base of each of the nasal locates are positioned between the central portion of the mask body and the line connecting the tips 717. In some configurations, the line connecting the tips 717 passes through the nasal locators between the openings (i.e., the portions delivering flow into the nasal passages) and the bases (i.e., the portions connecting the nasal locators to the rest of the mask).

With further reference to FIG. 7A, the mask seal may have a broadest exterior extent 741 of between about 30 mm and about 60 mm, and most preferably about 50 mm. The seal and mask frame may have an overall depth 743 of between about 40 mm and about 65 mm, and most preferably about 55 mm. Within this depth, the interior space defined by the seal, which wraps around the nose of the user in use, may have a depth 745 that is preferably between about 20 mm and about 40 mm, and most preferably about 30 mm.

Figure 9A:
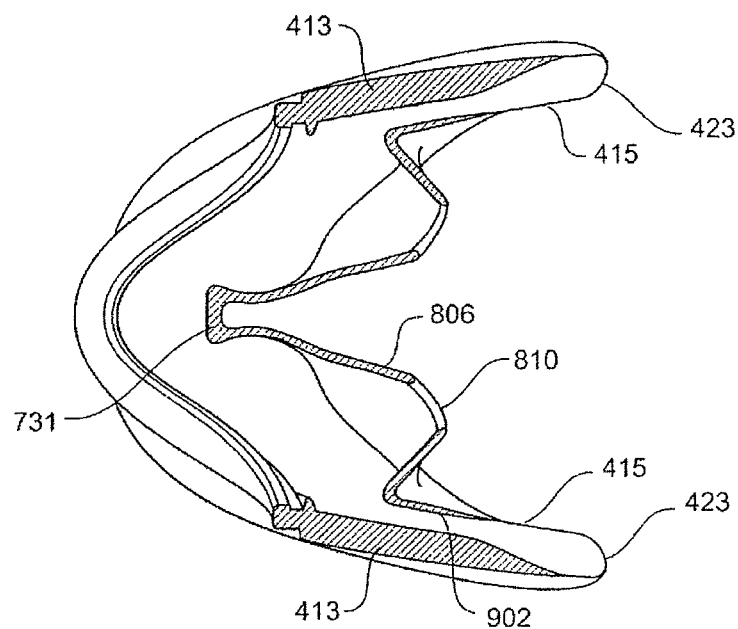
FIG. 9A is a top view of the seal of FIG. 7C, sectioned through line FF of FIG. 7D.
Figure 9B:
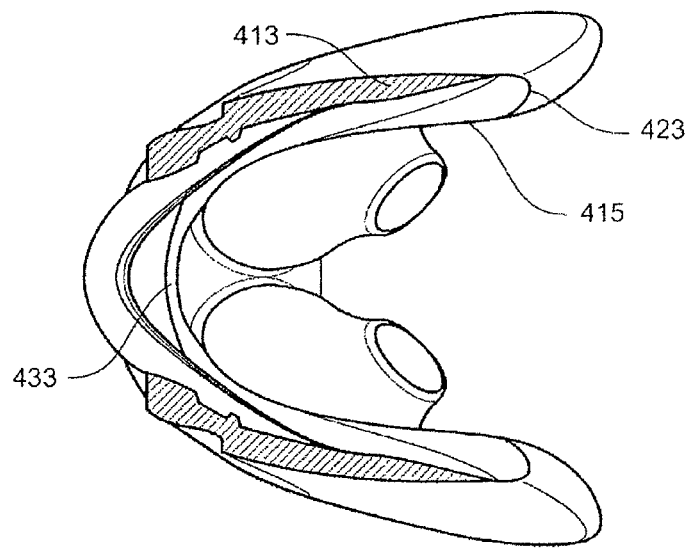
FIG. 9B is a top view of the seal of FIG. 7C, sectioned through line GG of FIG. 7D.

As can be seen from FIG. 7A, the seal curves through a significant arc such that the side portions approach generally parallel with each other and such that the side portions are generally opposed across the space that will accommodate the nose. The orientation planes of the side portions may form together an angle of between about 0° and about 45° (i.e., at 0° the side portions would be parallel) and preferably between about 0° and about 25°. In some configurations, this applies to both the inner wall, and the outer wall, as illustrated in FIGS. 9A and 9B. Preferably this is also true for substantially all of the vertically displaced levels within the seal, as illustrated by the different levels shown in FIGS. 9A and 9B.

The overall plan form of the seal, as illustrated in FIG. 7A, could be considered parabolic, half elliptical, half oval or U-shaped. Viewed generally, the central portion of the seal defines the width of the seal, with the side portions of the seal extending away from the lateral ends of the central portion in a direction substantially parallel with each other and substantially perpendicular to this width dimension.

Figure 8:
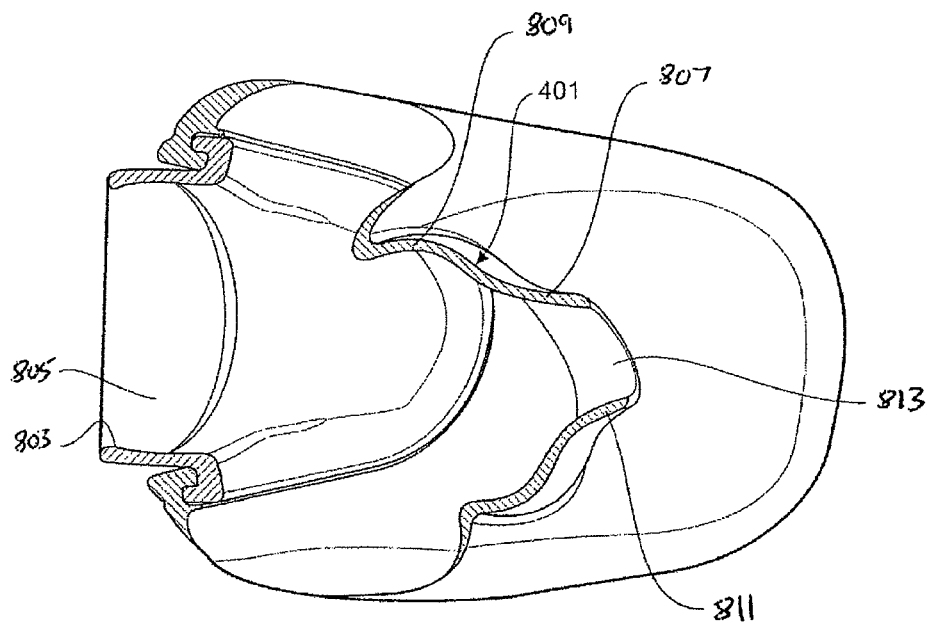
FIG. 8 is a side view of the seal and mask frame of FIG. 7A taken through line DD.

FIGS. 5B and 5C also show the connection of the swivel elbow 313 to the mask body 303. The illustrated swivel elbow 313 includes a ball portion 515 and an opening 517. The outer surface of the ball portion 515 is preferably a generally frustospherical surface but could be formed with variation and still achieve a substantial seal with the socket 503. Similarly, the socket 503 preferably is a generally frustospherical surface with a slight intruding lip. The structure is best illustrated in FIG. 8, where a lip 803 intrudes slightly relative to the remainder of the generally frustopherical surface 805.

The swivel elbow 313 preferably defines an angle between flow in the conduit, and flow through the connection to the mask of between about 0° and about 90°, preferably between about 30° and about 60°, and most preferably about 45°. The elbow may incorporate apertures 519 forming part or all of a gas washout vent for the patient interface. The apertures preferably are located on the outside of the bend of the elbow, substantially in the line of the flow path of gases leaving the mask.

FIGS. 5B and 5C also illustrate the connector portions 321 of the strap. As illustrated, the connector portions 321 are engaged over posts 513 of the mask body.

FIGS. 7A to 7D give context for cross sections illustrated in FIGS. 8, 7D, 9A and 9B.

Figure 7C:
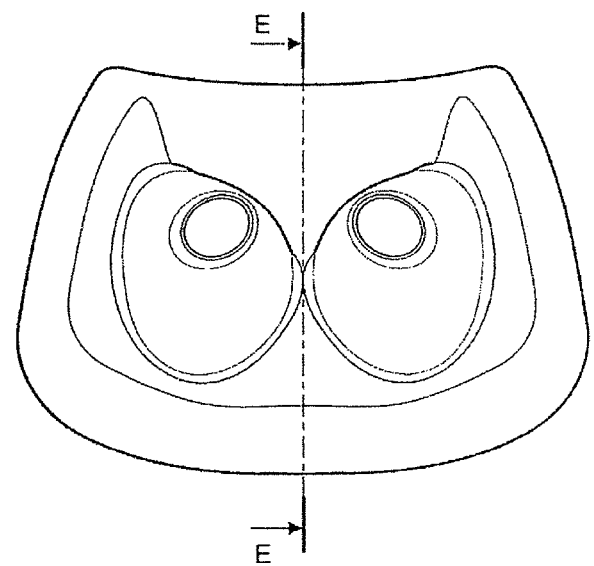
FIG. 7C is a view of the patient side of the seal of FIGS. 4A and 4C.
Figure 7D:
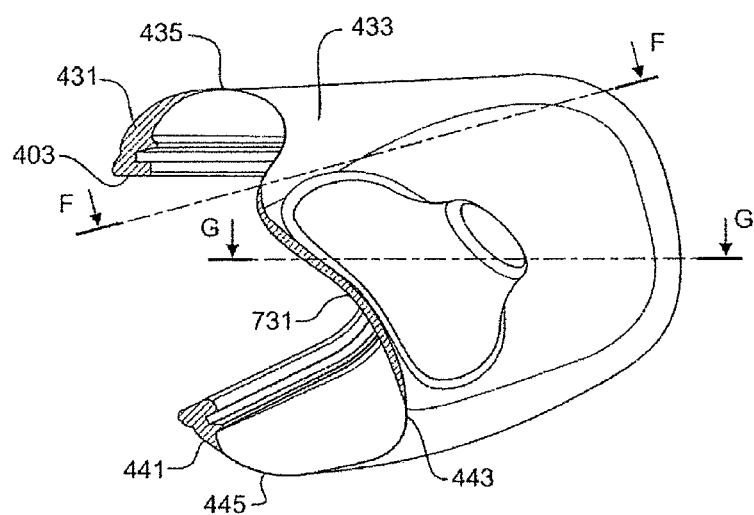
FIG. 7D is a side elevation of the seal of FIG. 7C, sectioned through line EE.

FIG. 7D is a cross section through line EE of the seal of FIG. 7C. FIG. 7D illustrates the thicknesses of portions of the seal in the vertical centre plane of the seal. This shows a thickening of the seal in the region 731 immediately adjacent and between the nostril locators. The cross section also illustrates a thickening of the seal in the outer wall portion 431 of the central portion of the seal above the outlet 403 and a thickening of the outer wall portion 441 of the central portion below the opening 403. These thickened sections are preferably gradually thickened from the thin supple perimeter portions 435, 445 respectively to a thickness of about 2 mm to about 4 mm. The supple wall portions, being the peripheral portions 435, 445 and the lower inside wall portion 443 and the upper inside wall portion 433, preferably have a wall thickness between about 0.05 mm and about 0.5 mm and most preferably between about 0.1 mm and about 0.2 mm.

The portion 731 between the nasal locators preferably has a thickness between about 2 mm and about 0.5 mm and preferably between about 0.8 mm and about 1 mm.

The dimensions are given relevant to a silicone material having a Shore A hardness of about 40. If the seal is formed of other materials, commensurate alterations of dimension may be possible while retaining suppleness of the envelope in the regions preferred supple and retaining sufficient stiffness to provide form to the envelope in regions intended to provide shape.

FIG. 8 is a section through DD of the mask seal and body of FIG. 7A. This illustrates the cross section of the central portion of the seal at the outward side as illustrated and described already in reference to FIG. 7D but also illustrates the connection of the seal opening to the opening of the mask body. However, the section of FIG. 8 also illustrates a preferred cross-sectional form of a nasal locator. In particular, the thickness of the material of the wall 807 of the nasal locator is preferably between about 0.5 mm and about 2 mm, and most preferably between about 0.8 mm and about 1 mm.

The nasal locator includes a base portion 809 and a nozzle portion 811 with a central opening 813. The nozzle portion, which includes the opening 813, generally fits inside the nostril of the user. The base portion 809 primarily locates the nasal locator at the entrance to the nostril.

FIG. 9A is a section through line GG of FIG. 7D of the seal. This is a cross section of the seal approximately on a horizontal centre plane passing through the nostril locators. This section shows that the wall portions 807 of the illustrated nostril locators, the immediately adjacent region 921 outside the perimeter of the illustrated nostril locators, and the centre portion 731 between the illustrated nostril locators all have a thickened wall relative to the more supple wall portions 415, 423 of the side portions of the seal. In particular, the regions immediately adjacent and including the nasal locators preferably have a thickness between about 0.5 mm and about 2 mm, and most preferably between about 0.8 mm and about 1 mm.

The outer wall portions 413 of the side portions of the seal are substantially thicker than the portions adjacent the nostril locators. These portions preferably have a thickness between about 2 mm and about 5 mm, and most preferably between about 3 mm and about 5 mm. These portions gradually taper in thickness to achieve the supple thickness where they become the peripheral portion 423.

The thickened portion of the outer side wall 413 of the side portions preferably extends to within about 10 mm of the outermost tip of the side portion.

The thickening and stiffness of these outer side portions 413 provides substantial form to the seal and provides stability with the seal in place. The side wall resists outward flexing of the side portions of the seal when the seal is inflated under pressure from the supply while the wall portions 413 will flex outwardly under pressure and have sufficient reaction force to retain the seal wrapped around the nose of the wearer.

The stiffening produced by thicker regions of the seal could be provided by a composite material, or combination of parts. For example, the stiffness could be provided by reinforcement in the silicone, or by a flexible insert of stiff material. The insert of stiff material could be integrated to the mask body. Preferably, the construction is such that the side portions of the seal provide resistance to flexing with an effective stiffness of at least about 1N force at the end of the stiffened region to flex the side portion through an angle of about 60°.

FIG. 9B illustrates a further, substantially horizontal plane, above the cross section of FIG. 9A. This cross section is taken through line FF of FIG. 7D. FIG. 9A again illustrates the thickness of the outer side wall portions 413 of the side portions of the seal relative to the inner side wall portions 415 and the perimeter portions 423 and relative to the thickness of the upper internal wall portion 433.

Again, the side portions 413 preferably have a thickness between about 2 mm and about 5 mm, most preferably between about 3 mm and 5 mm. The more supple portions 415, 423, 433 have thickness between about 0.05 mm and about 0.5 mm, and most preferably between about 0.1 mm and about 0.2 mm.

Figure 10B:
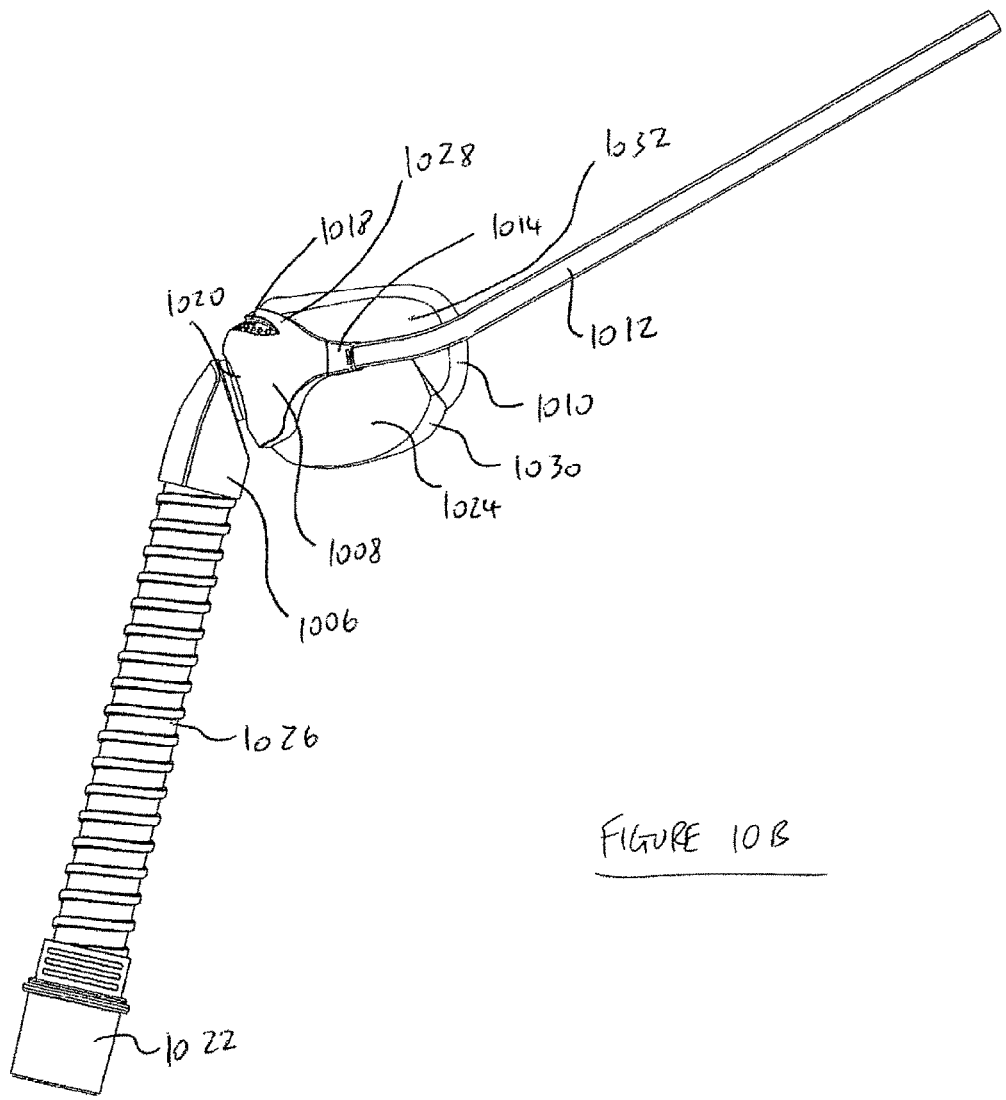
Figure 10C:
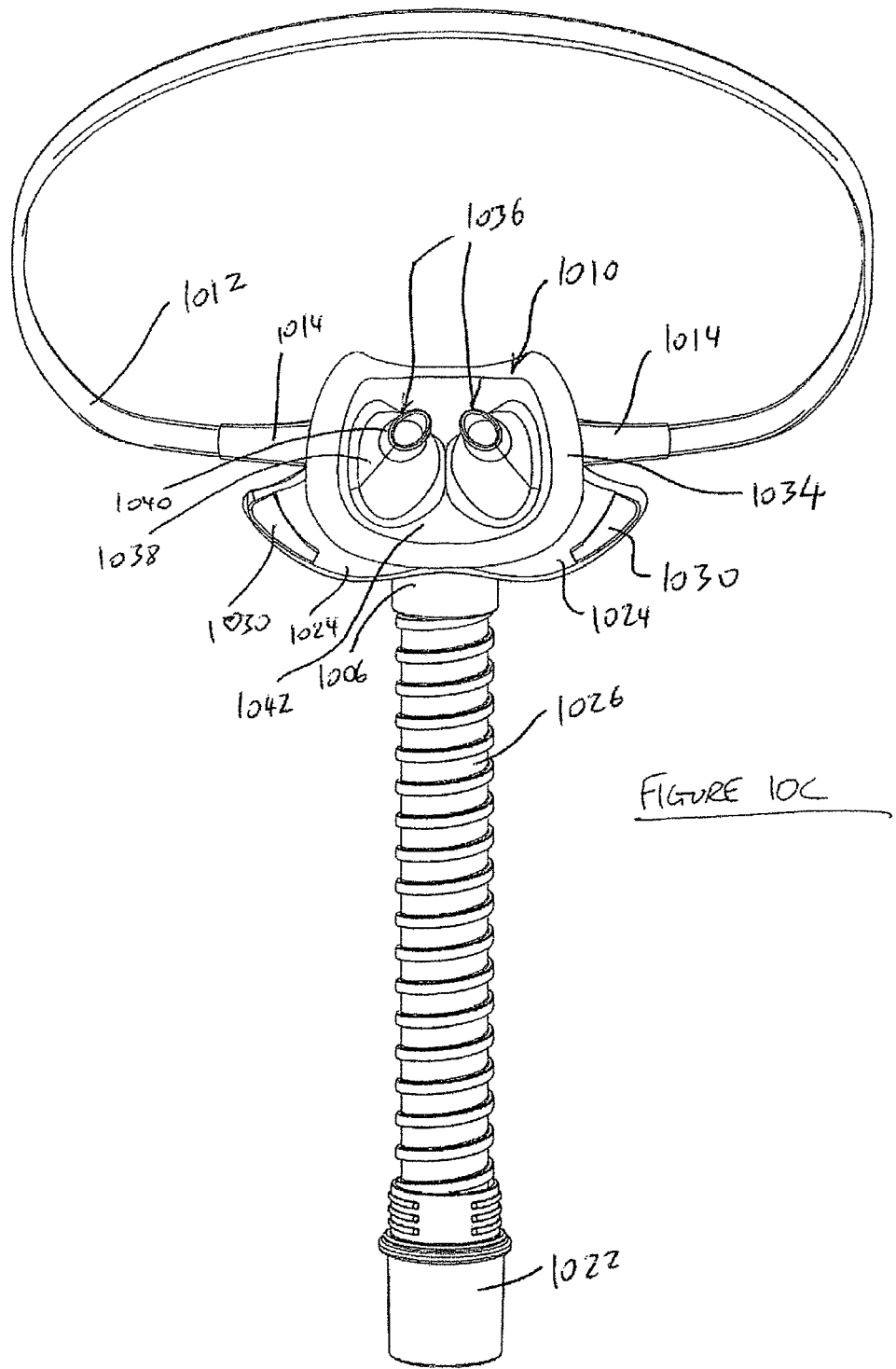

FIGS. 10A to 10C are perspective views illustrating a patient interface. FIG. 10A is a front view, FIG. 10B is a profile view, and FIG. 10C is a back view.

The illustrated interface 1000 is similar to the interface described with reference to FIGS. 3A to 3C. The seal 1010 includes many similarities to the seal of FIG. 4. The frame assembly 1008 has some of the same features as the frame 303 of FIG. 5. Like the interface of FIGS. 3A to 3C, the interface 1000 has a short depending conduit coupled to the frame assembly 1008 by a ball joint or swivel connection. Also, like the interface of FIGS. 3A to 3C, the interface preferably is secured to the head of the wearer by a single loop strap. This loop strap may be made of materials described later. The frame assembly may include lip stabilisers as described with reference to FIGS. 58 to 61.

Referring to FIGS. 10A to 10C, the interface 1000 has an overall configuration including a frame assembly 1008 and a seal 1010 on the inside of the frame assembly. A supply conduit 1004 depends from the frame assembly and supplies gases to the frame assembly and to the seal. Headgear 1002 connects to the frame assembly to secure the interface to the head of a user.

The frame assembly includes side portions 1016. Like the assembly of FIG. 5, the side portions may extend away from the outside wall of the seal (and therefore away from the face of the wearer when in use). At least one, and preferably both, side portion 1016 provides for connection with a connector 1014 of headgear 1002.

The connector 1014 is connected to and terminates an end of the strap 1012. Preferably each end of the strap 1012 includes a connector, and each side portion 1016 includes a matching cooperating connection.

The supply preferably includes a short flexible tube 1026, a supply connector 1022 and an interface connector 1006.

Tube 1026 may take many forms. For example the tube 1026 may be a stretchy conduit, a springy conduit that is usually short in the relaxed condition, an extruded corrugated tube or a wound tape tube with a spiral rib. The tube can be resistant to crushing and can allow extensive lateral turning and bending. The tube is preferably between about 50 mm and about 150 mm long.

The interface connector may include a bias flow vent. In the illustrated interface, no bias flow vent is provided on the connector. The connector 1006 preferably includes portions of a swiveling joint 1020 to the frame assembly 1008. The connector preferably includes a portion of a ball joint or swivel joint, and most preferably includes an extending hollow plug portion which extends into a socket of the frame assembly.

With reference to FIG. 10B, the connector preferably turns the supply flow through an angle of between about 25 degrees and about 75 degrees. Most preferably, the connector turns the flow through an angle of between about 40 degrees and about 60 degrees. This angle combines with the angle of the front face of the frame assembly in the immediate periphery of the joint 1020 (e.g., relative to the coronal plane of the wearer) so that the tube 1026 hangs easily below the interface (i.e., when the user is generally upright), remains close to the user when the user is lying down, keeps the joint 1020 close to the patient, thereby providing a lower profile and less leverage on the mask due to forces on the conduit.

The supply connector 1022 preferably includes a swivel.

The frame assembly 1008 preferably includes a bias flow vent 1018. Bias flow vent 1018 may include at least flow path from the interior of the interface to ambient surroundings. An interface may be provided for use with a return flow type ventilator that does not include any bias flow vent.

Where a bias flow vent is included, the bias flow vent may include at least one aperture extending through the wall defining the frame assembly. In the illustrated interface the bias flow vent 1018 includes a plurality of apertures. The apertures are arranged to direct the outlet flow of gases predominantly upward relative to the head of the wearer. As used herein, predominantly upward means the gases are directed in a direction that is more parallel to the plane of the face (or the coronal plane) than perpendicular to the plane of the face, and generally in the direction toward the forehead.

As best seen in FIG. 10C, the frame assembly may include depending support portions 1024 that extend below the seal 1010. The depending support portions include pads 1030 that are intended to provide support onto the upper lip region of the wearer, in the vicinity of the nasolabial folds. On some users, the pads 1030 may extend onto the lower cheek region immediately adjacent the nasolabial folds. The pads are intended to contact the face only when desired to support the seal. This aspect of the interface is covered in more detail with reference to FIGS. 58 to 61.

Also in FIG. 10C, the illustrated seal can be seen to include a pair of nasal locators 1036. Each nasal locator includes an opening, which in use is disposed within a nostril of the wearer. The nasal locators extend from a supple inner wall portion 1042 of the seal.

In the illustrated interface, each nasal locator includes a generally tubular nozzle portion 1040 and a convex base portion 1038. The generally tubular nozzle portion 1040 may be somewhat tapered toward the open end. The convex base portion may be considered a dome shape.

In some embodiments, the convex base portion extends all of the way around the locator and generally surrounds the tubular nozzle portion. In some embodiments, the convex base portion may extend most of the way around, but not completely around, the locator. For example, the base portion may extend continuously about 60% or more of the way around the locator.

Both the nozzle portion and the base portions of each locator are preferably oval or elliptical in cross-section. This is illustrated in more detail in FIGS. 11E to 11H.

Figure 11A:
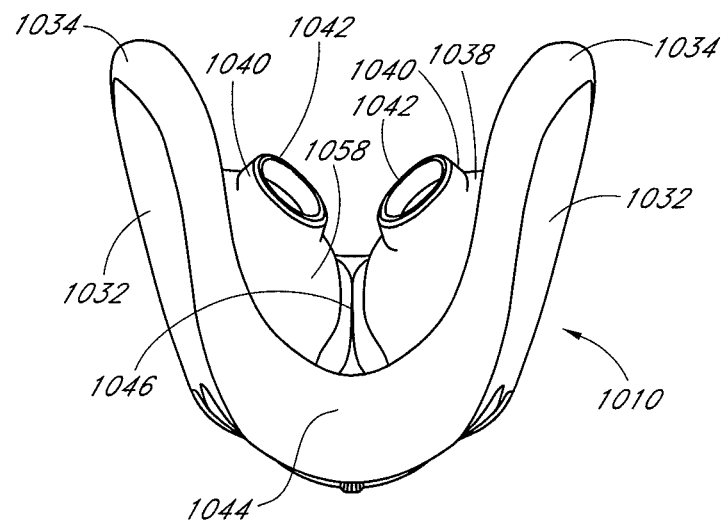
Figure 11B:
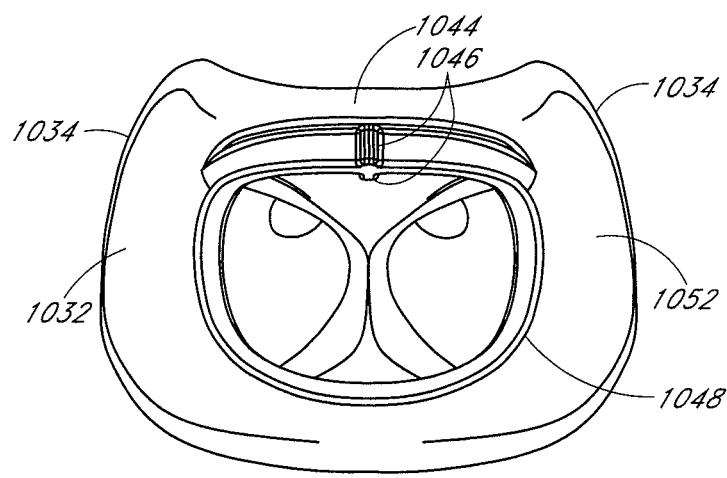
Figure 11C:
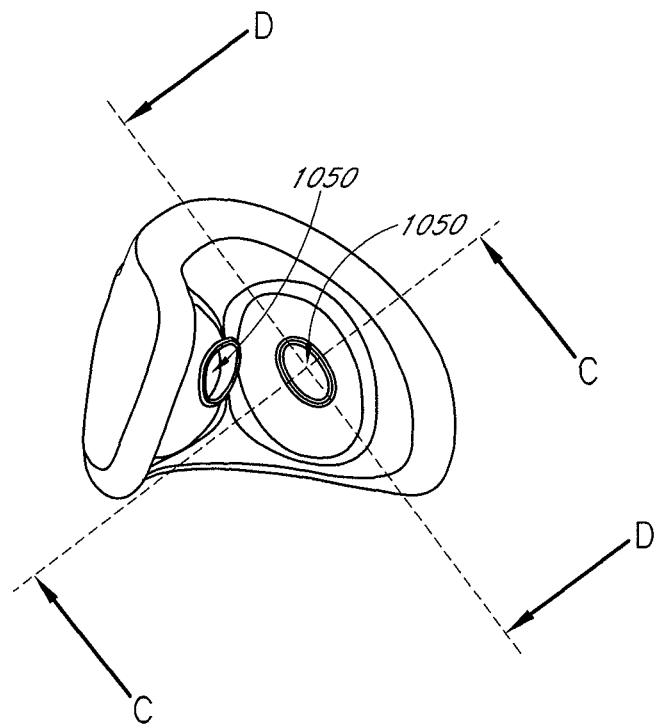
Figure 11D:
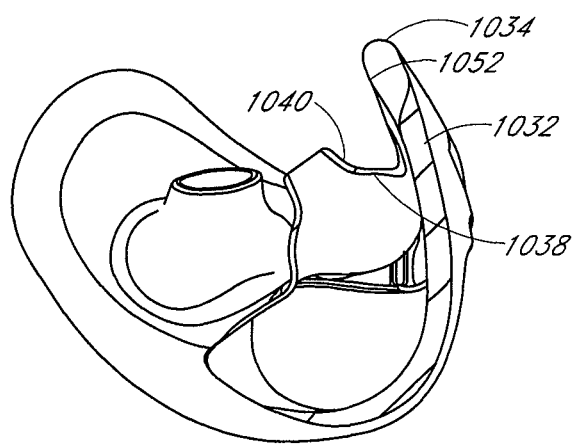

FIGS. 11A to 11H are views of the soft seal component of the interface of FIGS. 10A to 10C. FIG. 11A is a top view. FIG. 11B is a front view. FIG. 11C is a rear view taken from a position directly facing the open end of a nasal locator. FIG. 11D is a cross section through section CC in FIG. 11C.

From these figures many similarities can be seen to the seal of FIG. 4. The utility and function of the similar features will not be repeated in detail.

In general terms the seal includes an inward facing wall portion and an outward facing wall portion. The inward facing wall portion forms the seal against the face surfaces of the wearer. The outward facing wall portion connects the seal to the frame assembly and supports the overall shape of the seal. Like the seal of FIG. 4, the general shape of the seal is a U-shape or a V-shape with side portions extending generally rearward from a central transverse portion.

The outward facing wall portion includes side portions 1032 that are of greater cross section than the inward facing wall portion. The inward facing wall portion includes nasal locators supported on a generally supple background 1052. A illustrated supple periphery 1034, 1044 connects the outward facing wall portion to the inward facing wall portion around the perimeter.

With particular reference to FIG. 11A and to FIG. 11D, each nasal locator preferably comprises a tubular portion 1040 and a dome portion 1038. Furthermore, each illustrated tubular portion terminates in a rim 1042 that defines an opening 1050, which is shown in FIG. 11C.

The illustrated tubular portion tapers toward the opening 1050. The taper is preferably a linear taper but may be a curved taper or a combination of curved and linear. The surfaces of the dome portion and the tubular portion meet at an included, obtuse angle, of between about 120 degrees and about 160 degrees, for example.

The cross-section of FIG. 11D suggests that the tubular portion 1040 is approximately frustoconical and that the dome portion 1038 is approximately frustospherical. However, in each case, the alternate cross section (FIGS. 11F to 11H) is oval rather than circular. Accordingly, the form of the dome is better regarded as ellipsoid. The form of the tubular portion is better regarded as an elliptic cone. However, in each case the shape need not be a true ellipse, and may instead comprise less regular oval shapes, such that the forms might be regarded an ovaloid or ovaloid dome, an ovoid or ovaloid cone or a tapering ovoid or ovaloid tube.

The tubular portions of the nasal locators are spaced apart but generally aligned such that their axes are generally convergent. Preferably the convergent distance is between about 10 mm and about 40 mm from the openings of the nasal locators.

The dome portions of the nasal locators come close together, abut or adjoin at a cleft 1046 at the centreline of the seal. Preferably, the cleft 1046 is formed to allow some freedom of movement of the dome of one nasal locator relative to the dome of the other nasal locator.

With particular reference to FIGS. 11E to 11H, the oval cross section of each nasal locator is shown in more detail. In particular, three cross sections of the nasal locator are shown. These cross-sections are taken on planes that are generally parallel to the plane of the opening of the open end of the nasal locator.

The cross sections shown the substantially oval form. In particular, the oval or ellipse of the opening 1050 preferably has an aspect ratio of approximately 1.8 to 1. The major axis of the oval or ellipse is greater than about twice the minor axis, and preferably between about 1.5 times and about 3 times the minor axis.

The generally oval form is retained throughout the tubular portion and the dome portions of the nasal locator. However, in the illustrated seal, the absolute difference in the major and minor axes is retained rather than the ratio. Therefore, the ratio reduces moving from the shape of opening 1050 to the first cross section 1054 spaced toward the base of the tubular portion. The ratio further reduces moving from cross section 1054 to cross section 1056 at an intermediate position on the dome portion. The ratio further reduces moving from cross section 1056 to cross section 1058 at the base of the dome portion.

By way of example, for the tip opening, the major axis dimension may be about 9 mm and the minor axis dimension may be about 5 mm. For the cross-section of the tubular portion at EE, the major axis dimension may be about 13 mm and the minor axis dimension may be about 9 mm.

For the dome portion at GG, the major axis dimension may be about 18 mm and the minor axis dimension may be about 15 mm.

For the dome portion at HH, the major axis dimension may be about 22 mm and the minor axis dimension may be about 18 mm.

As is best illustrated in FIG. 10C, the oval forms of the nasal locators are preferably not aligned parallel when viewed from the back of the interface. In particular, the upper ends of the ovals are closer than the lower ends. When projected posteriorly onto a coronal plane of a hypothetical wearer, the major axes of the ovals form an angle of between about 60 degrees and about 120 degrees.

Each nasal locator preferably is provided with a lip 1042 at the open end 1050. The material at the lip 1042 preferably is thicker than the material of the rest of the tubular portion, or of the material of the region of the tubular portion in the near vicinity of the lip. The thickened lip provides some positive form to the end of the locator when locating the locator in the nostril of the wearer. This may be useful for the wearer to better feel the end of the locator when fitting the interface.

FIGS. 11B and 11E also illustrate features of the seal involved in securing the seal to the frame assembly. As seen in FIG. 11B, the outward facing portion of the seal includes a major opening for securing with the frame assembly. The major opening includes a lip 1048 that runs the perimeter of the opening. The lip may be constituted by the thicker regions of the outward wall of the seal. For example, the lower portion of the lip is illustrated in cross section in FIG. 11E.

At a location, or multiple locations, on the lip, markers or features may be provided to encourage the correct assembly of the seal relative to the frame assembly. In the illustrated embodiment, the seal is arranged to be detachable from the frame.

For easier positioning, the lip preferably is provided with a protrusion that engages in a notch of the frame when the seal is correctly positioned. The lip may be provided with a protrusion 1046 extending in either or both of the inward and outward direction. In the illustrated embodiment, two protrusions 1046 are provided that engage with notches 1074, 1092 of the frame.

The lip of the seal takes the overall form of a bent oval. In other words, the lip takes the form of an oval that has been bent so that the ends of the oval are curved away from a plane generally tangential to the central portions of the oval. This can be generally seen in the form of the outward wall portion of the seal in FIG. 11A.

Figure 12:
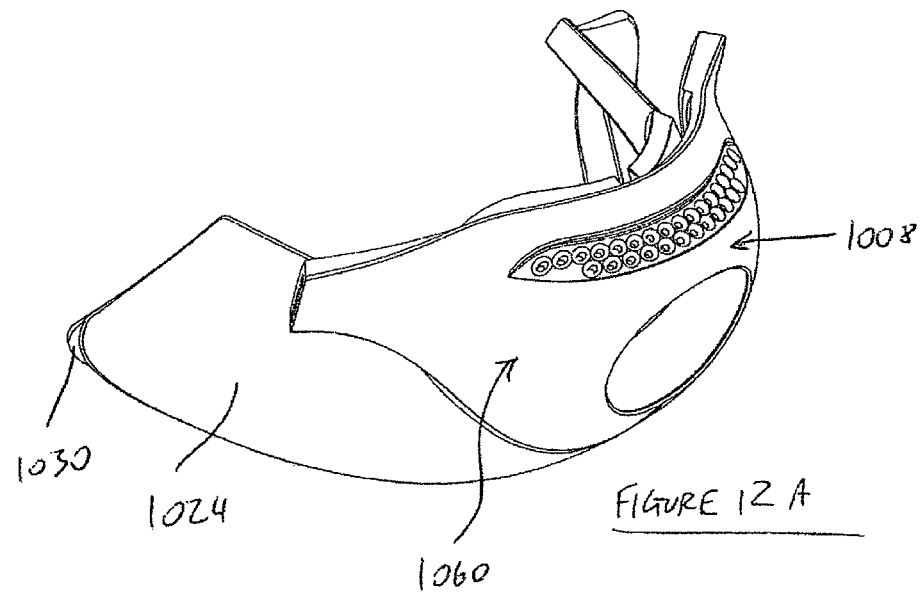
FIGS. 12A to 12H are views of a frame assembly of the interface of FIGS. 10A to 10C.
FIG. 12I is a rear view of a frame assembly having a different channel path for securing the lip of the seal.
Figure 12:
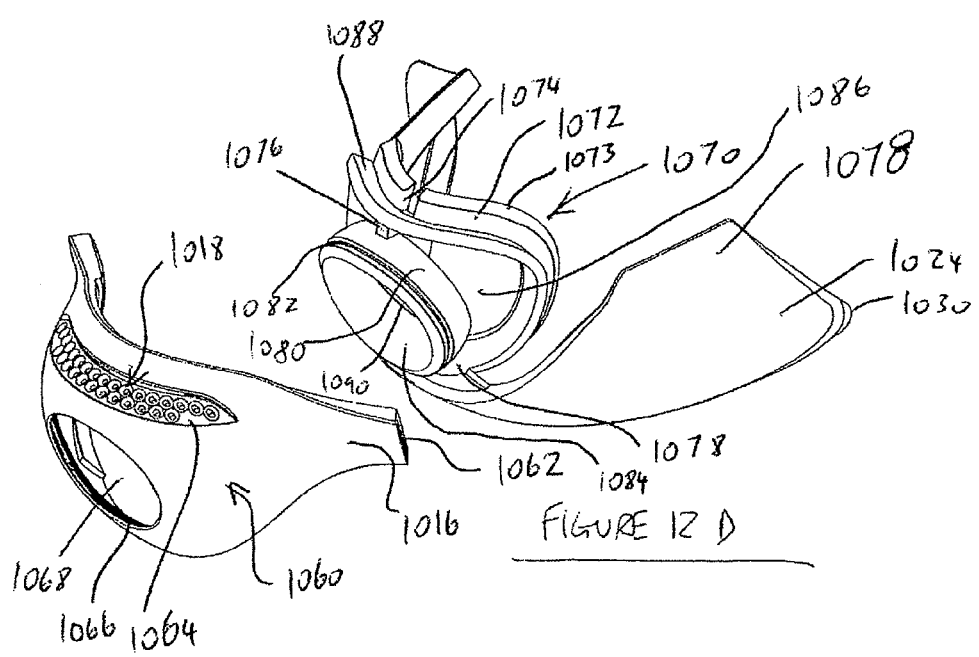
Figure 12B:
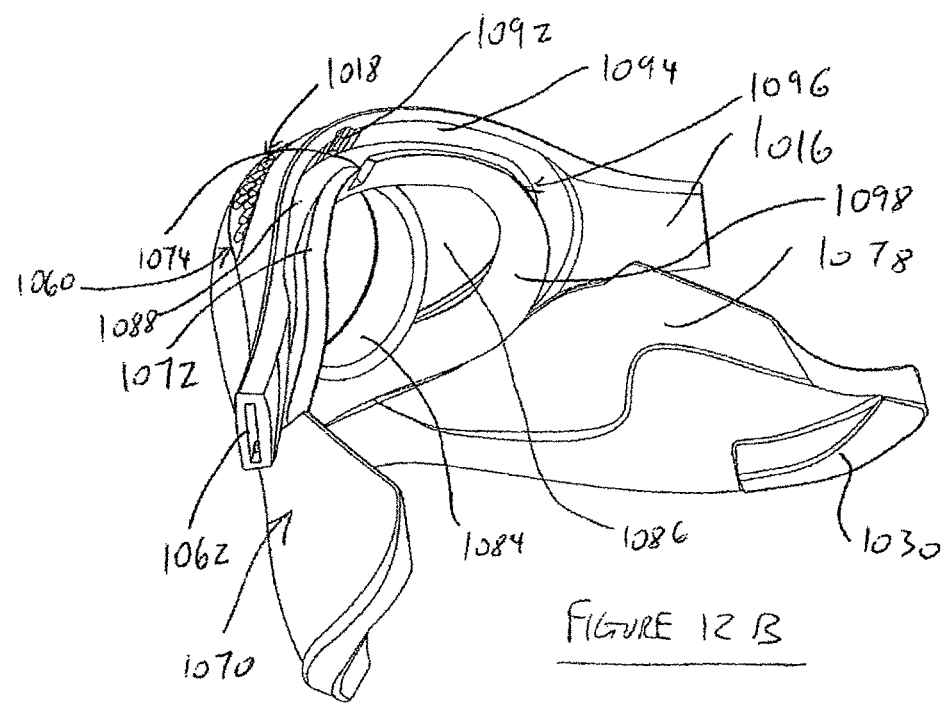
Figure 12C:
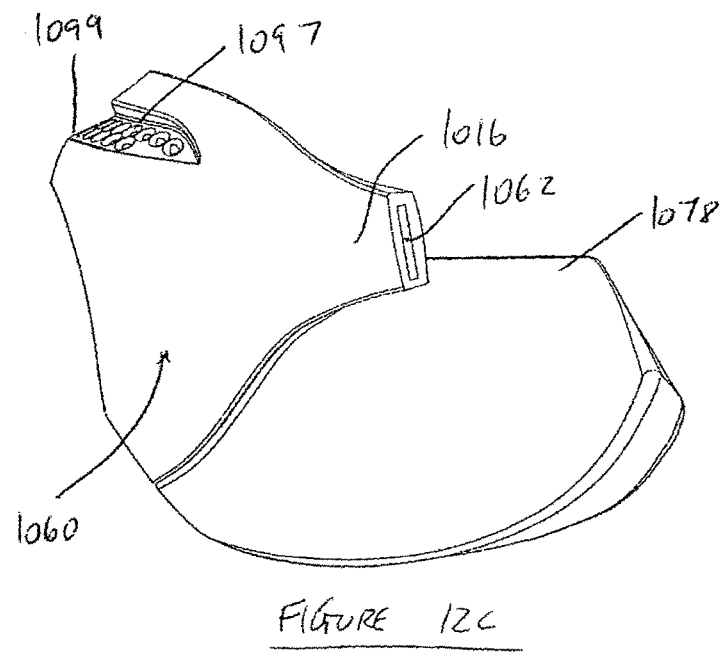
Figure 12E:
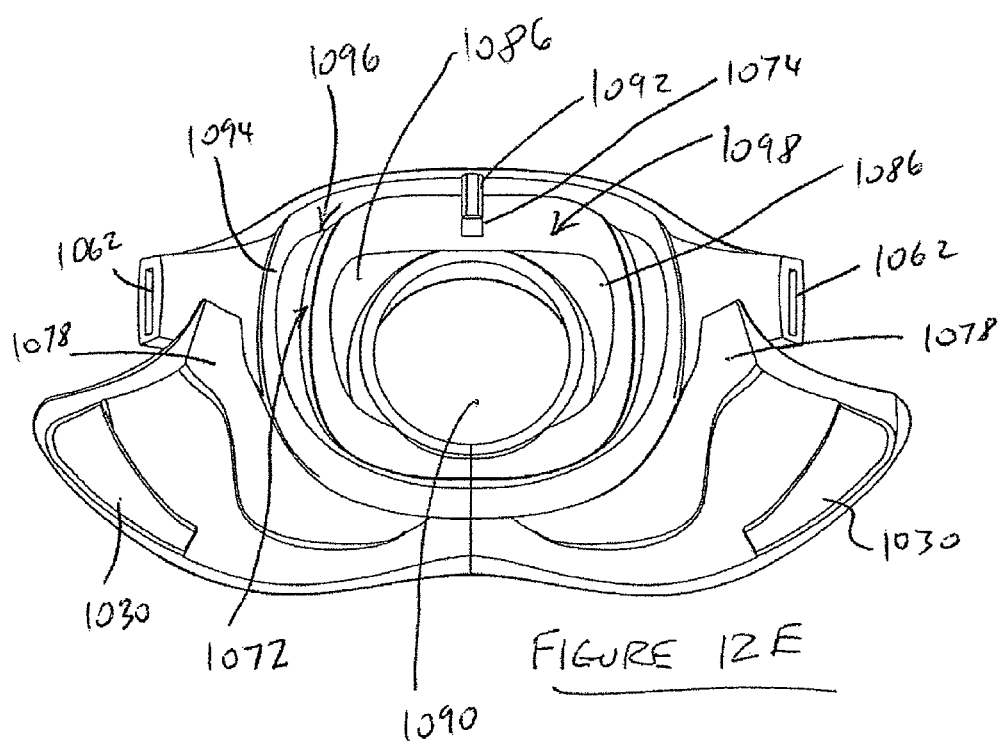
Figure 12:
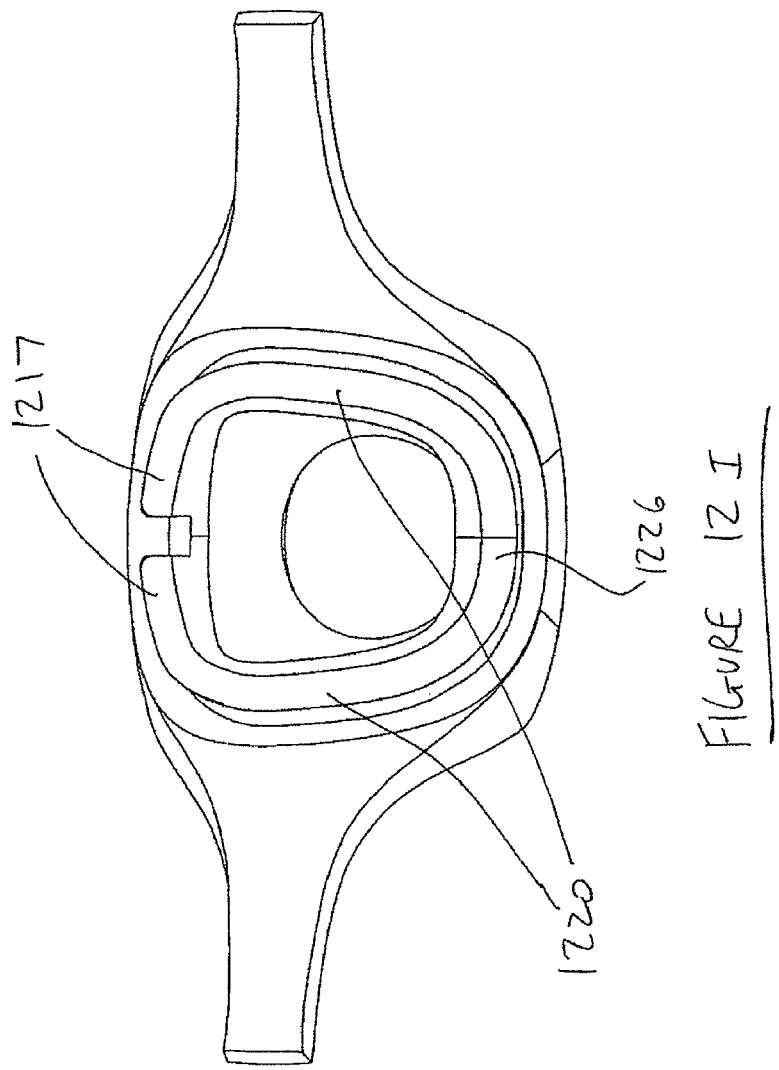
Figure 13:
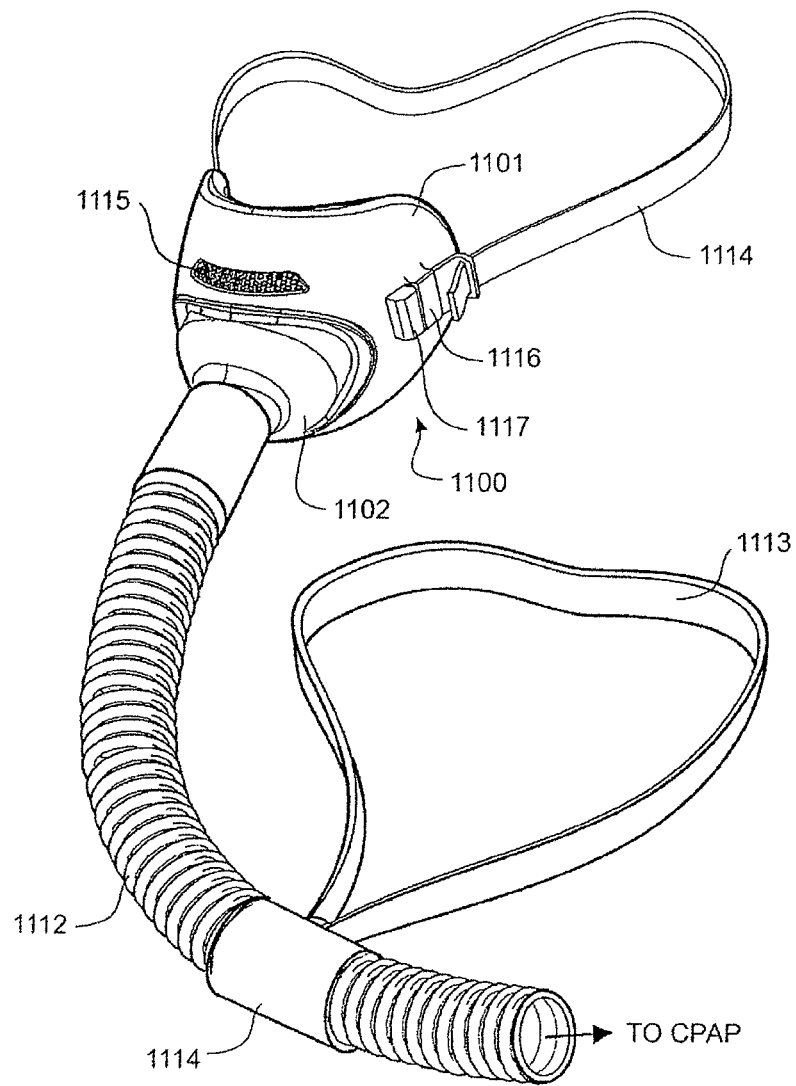
FIG. 13 shows a further embodiment of an interface with an inflatable seal. The interface includes a seal body, frame, tubing and head strap.
Figure 14:
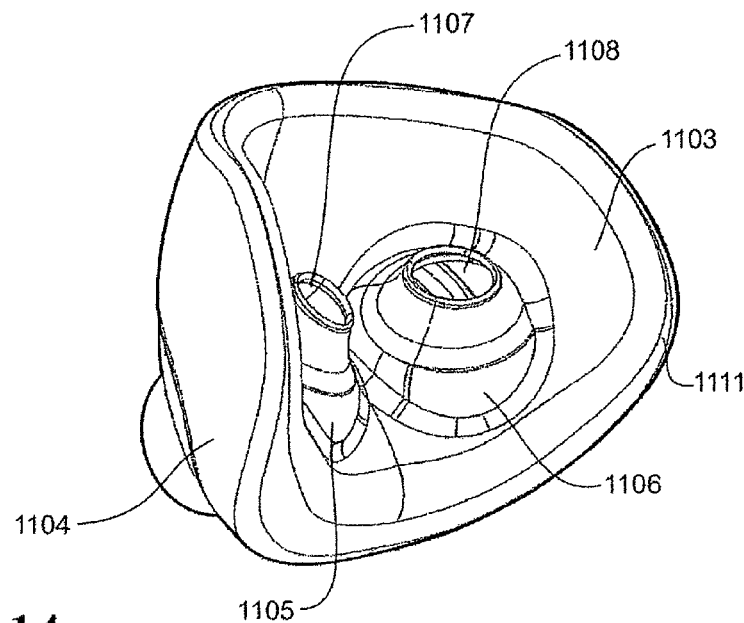
FIG. 14 shows the seal body of the interface of FIG. 13.
Figure 15:
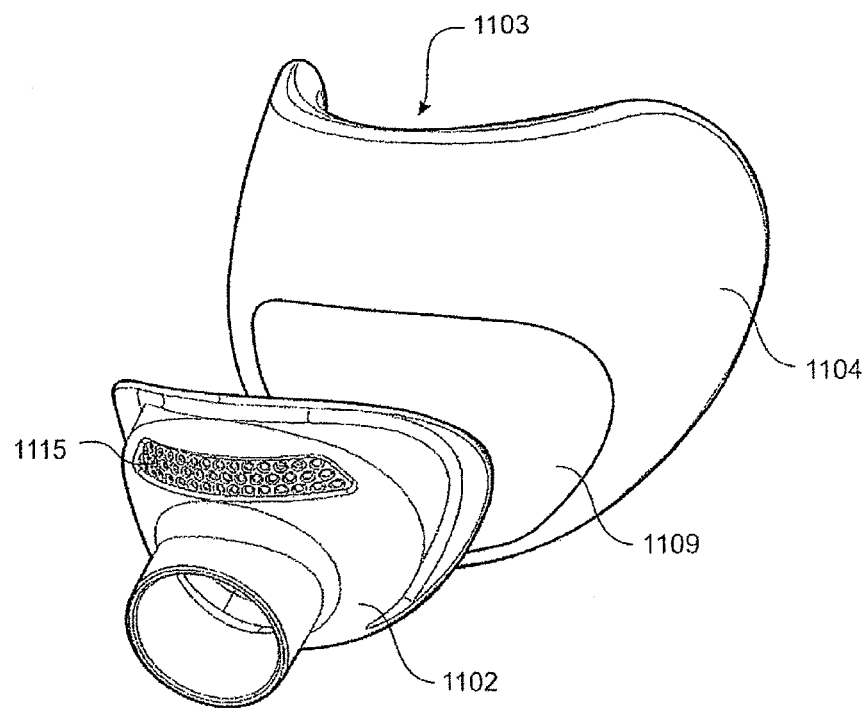
FIG. 15 is a perspective view of the frame and seal body of the interface of FIG. 13.

FIGS. 12A to 12H are views of a frame assembly of the interface of FIGS. 10A to 10C. FIG. 12A is a front perspective view of the frame assembly. FIG. 12B is a rear perspective view of the frame assembly. FIG. 12C is a side profile of the frame assembly. FIG. 12D is an assembly view of two components of the frame assembly. FIG. 12E is a back view of the frame assembly.

FIG. 12I is a back view of a frame assembly that is of a slightly different configuration. In FIG. 12I, the stabiliser portions are not shown. This illustrates an alternative configuration of the channel for securing the seal. The frame assembly may otherwise be formed and assembled in substantially the same manner as the frame assembly of FIGS. 12A to 12H.

The frame assembly 1008 comprises two major components: a first component 1070 and a cover 1060. The two components of the frame assembly combine to provide a channel 1096 for securing the lip 1048 of the seal. The first component 1070 may include a first portion of the channel while the cover 1060 provides a second portion of the channel. The component 1070 may provide an inside flange portion 1072 and the cover may provide an outside flange portion 1094. A base portion for the channel may be provided extending from the flange portion of either part. For example the base portion 1088 may be provided from the flange portion 1072.

The flange portion 1072 may include a notch 1074 that receives a locating feature of the lip 1048 of the seal. The flange portion 1094 may include a notch 1092 that receives an additional locating feature of the lip of the seal.

According to the preferred form of the seal and the channel, the channel has a general outward flare such that portions of the channel on opposite sides of the main opening diverge relative to each other when progressing from the base of the channel to the open edge of the channel. Accordingly, the lip of the seal stretches to pass over the inner flange portion 1072 and the seal is retained in the channel by the elastic tension of the lip.

In the frame assembly of FIGS. 12A to 12H, the channel forms a general bent ellipse. In the example of FIG. 12I, the channel follows a path more like a bent rounded oblong or trapezoid. In particular, the overall path of the channel is not as broad as the path of the channel in the embodiment of FIGS. 12A to 12H. Furthermore, the channel includes comparatively straight side portions 1220. The side portions 1220 converge slightly, extending toward the lower portion 1226, and diverge slightly, extending toward the upper portion 1217. While this assembly retains the overall bent oval shape, the straightened side portions are found to improve ease of assembly in comparison with the sharply curved end portions of the bent ellipse of FIGS. 12A to 12H.

The notch and protrusion alignment preferably is provided adjacent the upper or lower portion of the channel, most preferably adjacent the upper portion of the channel. Thus, the lip 1048 can be seated in the channel with the correct location and the rest of the lip then is stretched over the inner flange portion 1072.

The first component 1070 may include extensions to carry support pads 1030. For example, a lower shield portion may extend in a curve below the supply opening of the interface. The lower shield portion may include side portions. The support pads 1030 can be provided on the lower inside surface of the side portions.

An internal surface 1078 of an upper portion of the shield may wrap around to the sides of the interface and may be located outside and adjacent the outward wall of the seal. The upper portions of the shield can assist in retaining the form of the seal under internal gases pressures, by constraining outward deflection of the outside of the seal envelope.

The first component may carry a portion of the swivel connection 1020. Preferably the first component 1070 includes a ring portion 1080 that is open to the front and the back. The ring portion preferably includes surfaces to engage with surfaces of the supply tube connector.

Preferably, the ring portion 1080 includes an inwardly facing substantially spherical surface 1084. The inwardly facing surface 1084 may engage an outwardly facing complimentary surface of a ball portion of the supply tube connector. The ball portion of the supply tube connector may have in internal passage leading gases from the supply tube through the ring portion 1080.

One advantage of this arrangement is improved available material choices. The supply tube connector preferably is made from a different base polymer material relative to the ring portion 1080 of the component 1070. Different polymer materials working against one another tend to exhibit lower friction and noise than polymers of the same base material. The outside cover 1060 can be formed from the same material as the supply tube connector and thus present an aesthetically pleasing exterior.

For example, the ring portion of component 1070 may be formed from a material chosen for its strength and toughness, such as a polycarbonate plastic, and the cover 1060 and supply tube connector formed from a plastic chosen primarily for surface finish and appearance, such as an acetal plastic. The acetal plastic may include a lubricating copolymer, such as PTFE (polytetrafluroethylene).

The ring portion 1080 may also provide features for securing the two components 1060, 1070.

For example the outer surface of ring portion 1080 may be provided with outwardly facing features, such as depressions or a channel 1082, to cooperate with inwardly facing clips or an inwardly facing annular ridge 1087 of the perimeter 1066 of the opening 1068 of the cover 1060. This is best illustrated in the cross section in FIG. 12G.

The outer periphery of the cover 1060 may blend into the surfaces of the component 1070 in some parts. For example, the lower curved edge of the cover 1060 may abut the upper curved edge of the lower shield of the component 1070. This is indicated at 1081 in FIG. 12G. A similar abutting edge at the side portions is indicated at 1081 in FIG. 12H.

The components 1060, 1070 may form an outlet plenum adjacent the bias flow vent 1018. This is best understood by considering the exploded view of FIG. 12D, the rear view of FIG. 12B, and the cross sections of FIGS. 12G and 12H. The plenum 1079 is defined between a bent oval frame portion 1072 of component 1070 and the inside surface of the cover 1060 in the vicinity of the aperture 1068.

The illustrated openings 1086 into the plenum 1079 are defined by the rear edge of the ring portion 1080 and by the oval frame portion 1073. Gases flowing from the seal to the bias flow vent pass through these openings. The inside surface 1098 of the flange 1072 of oval frame 1073 preferably converges moving toward the plenum, which defines a flow directing surface acting somewhat like a funnel.

The holes of the bias flow vent 1018 lead from the plenum 1079.

The ring portion 1080 opens essentially centrally through the oval frame portion 1073. This divides the flow into the seal and the flow out of the seal essentially at a location directly adjacent the open end of the seal.

The ring portion may be supported in this position by one or more supporting struts 1076, or by regions at the top and bottom where the ring and oval frame portion come together.

The bias flow holes 1097 are arranged in a curve around the upper portion 1089 of the plenum chamber 1079. This upper portion is quite confined in the location illustrated in FIG. 12G, immediately above the ring portion 1080, but more open to either side.

To provide an upward exit flow (generally parallel to the coronal plane of the wearer), the bias flow holes may be arranged in a shelf portion 1099 of the wall of the cover 1060.

The lower shield portion of the component 1060 may include a soft covering 1085, such as an overmoulded layer of a soft biocompatible material, over a more rigid skeleton or frame 1083. A preferred covering would be, for example but without limitation, a thermoplastic elastomer, a polyurethane foam, or a silicone elastomer. The skeleton or frame 1083 of the component 1060 may be formed from a copolymer including an amount of a plastic material that bonds strongly with the covering material. For example but without limitation, the frame 1083 may be formed from a polycarbonate siloxane copolymer. The siloxane contributes chemical resistance and improves the bonding of the overmoulded silicone cover.

Extreme side portions 1016 of the cover 1060 diverge from the outer surfaces of the shield of component 1070. The side portions 1016 end in sockets 1062 that receive connectors of the headgear strap.

FIGS. 13 to 20 show a further embodiment of an interface with a wrap around inflating seal. The interface 1100 includes a seal body 1101 and frame 1102.

Attached to the frame 1102 is tubing 1112 that is attached to a gases supply apparatus. The tubing supplies gases to the mask frame and seal. The tubing 1112 may be tethered to the user (i.e., the person wearing the interface 1100) by a lanyard 1113. In use, the lanyard 1113 extends about the user's neck. The lanyard 1113 is affixed to the tube by any suitable mechanism, however, shown is a c-shaped clip 1114 attached to the lanyard 1113 that clips about the tubing.

The interface 1100 is held in place over the user's nose by way of a head strap 1114. The strap preferably is made of a flexible type material, such as silicone or a laminated material well known in the art of head gear straps. Each end of the strap 1114 preferably is fitted to a clip 1116 that attaches to a corresponding eyelet 1117 formed in or attached to the seal body 1101. The strap may be a flat moulded silicone strap, a small hollow silicone tube, or other suitable configuration.

The frame 1102 may have formed in it a plurality of bias flow holes 1115 to allow for exhausting of the user's exhalated gases from the interface. Alternatively, bias flow holes may be formed in the seal body 1101 to allow for exhausting of gases.

The seal body 1101 is a supple or inflatable type seal. The illustrated seal body 1101 is curved in shape to match the contours of a human face and extends about the user's nose, substantially wrapping the user's nose. The seal body 1101 preferably extends completely or substantially completely over the side of the user's nose and may also extend at least partially over the user's cheeks. The seal 1101 comprises an inner wall with an inner wall with an inner surface 1103 and an exterior wall with an outer surface 1104. Projecting from the inner surface 1103 are nasal locators 1105, 1106, each with outlets 1107, 1108.

As with the embodiment of FIGS. 10 to 12, the seal body 1101 includes an inlet opening 1109 that is opposite the nasal locators 1105, 1106 and that receives the frame 1102.

The seal 1101 has a variable wall thickness such that there is some enhanced rigidity around the portions of the seal that project outward and such that there is some flexibility between the nasal locators 1105, 1106 and a periphery 1110 of the inlet opening 1109 of the seal. This means there is a decoupling effect between the nasal locators 1105, 1106 and the inlet periphery 1110, and subsequently to the mask frame 1102. This will mean that some movement of the mask frame will be possible without disrupting the sealing of the nasal locators 1105, 1106 on or in the user's nostrils.

Figure 18:
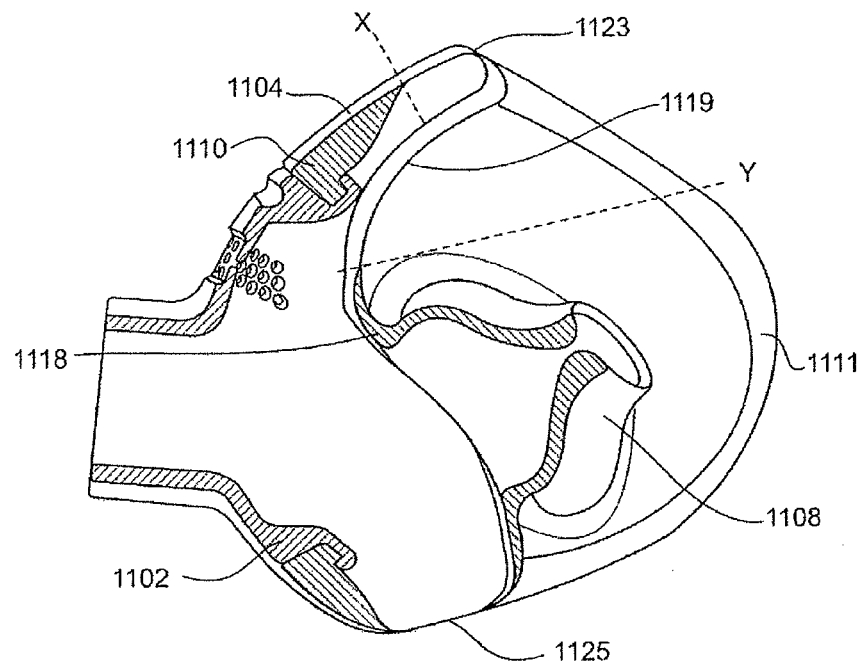
FIG. 18 is a cross-section of the frame and seal body through BB in FIG. 17.
Figure 19:
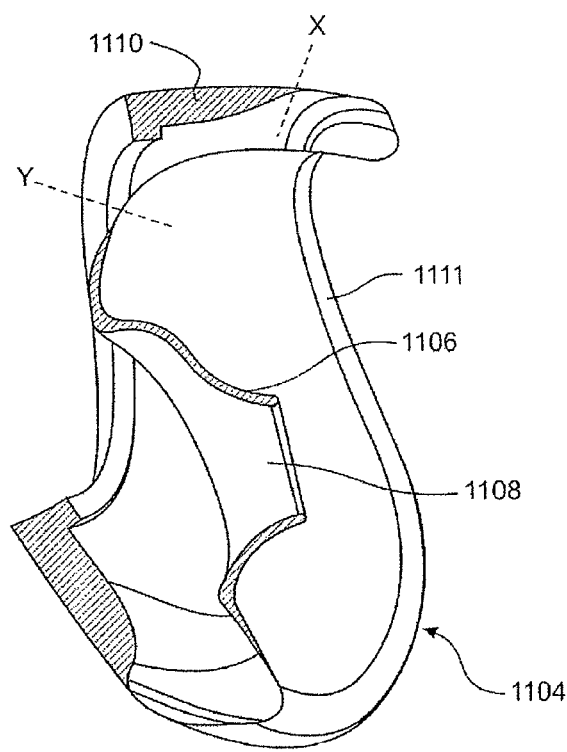
FIG. 19 is an alternative cross-sectional view of the seal body.

As can be seen in FIG. 18, the inlet periphery 1110, which defines the gases inlet 1105 to the seal, has a substantially thick cross-section. This provides enhanced relative rigidity to the inlet periphery 1110. Similarly, the nasal locators 1105, 1106 have a substantially thick cross-section. However, the thickness of the nasal locators may not necessarily be as thick as or thicker than the inlet periphery 1110. In the illustrated form, the thickness of the nasal locators is less than that of the inlet periphery.

The areas between the inlet periphery 1110 and the nasal locators 1105, 1106 is preferably thinner in cross-section than both nasal locations and the inlet periphery. For example, in FIG. 18 the length of the seal 1101 between X and Y is formed to be substantially thinner in cross-section than either the inlet periphery or the nasal locators. This means this length is more flexible, effectively allowing more movement of the nasal locators 1105, 1106. Furthermore, as the length between X and Y, including an outer periphery 1111, is thinner in cross section, the seal will easily inflate to assist in the sealing of the seal about the user's nose.

As shown in FIG. 18, preferably a region 1118 of the envelope adjacent to the base or root of each nasal locator has a thickened cross section. As shown, the length or region 1119 of the seal between the region 1118 and the thickened inlet periphery 1110 can be formed to be substantially thinner in cross-section than either the inlet periphery 1110, the nasal locators 1105, 1106 or the region 1118.

In some configurations, the envelope includes a thickened region 1118 adjacent the root of the nasal locators and the thickness of the cross section of the nasal locators is not thickened. For example, the thickness of the cross section of the nasal locators may be similar to the thickness of the envelope region 1119 extending between the region 1118 adjacent the nasal locators and the inlet periphery 1110. The thickened region 1118 adjacent the root of the nasal locators reduces the likelihood of deformation or excessive ballooning of the base of the nasal locators under typical CPAP pressure. However, the thinner wall of the nasal locators 1105, 1106 in this embodiment may balloon to some degree under CPAP pressure.

Preferably, the seal 1101 is formed from silicone with a Shore A hardness of about 40. Alternatively, other materials with similar properties may be used. For silicone with a Shore A hardness of 40, or other material with similar properties, the thickness of the envelop region 1119 extending between the nasal locators and the inlet periphery is less than approximately 0.5 mm. Preferably this region 1119 has a thickness of about 0.1 mm to about 0.2 mm. Alternatively this region 1119 of the envelope may have a thickness of less than about 0.1 mm, for example about 0.05 mm.

The thickness of the region 1118 adjacent the base of the nasal locators preferably has a thickness of less than about 2 mm. Preferably, the thickness of the region 1118 adjacent the base of the nasal locators is about 0.8 mm to about 1.0 mm. Alternatively, the thickness of the region 1118 adjacent the base of the nasal locators may be less than about 0.8 mm, for example about 0.5 mm.

The thickness of the region adjacent the inlet periphery is about 3 mm to about 5 mm, but could be thinner such as, for example, about 2 mm.

The nasal locators have a thickness of less than about 2 mm. In the preferred embodiment, the nasal locators have a thickness of about 0.8 mm to about 1.0 mm. Alternatively, the thickness of the nasal locators may be less than about 0.8 mm such as, for example, about 0.5 mm.

In the alternative embodiment described above, the thickness of the nasal locators is similar to the thickness of the envelope region 1119 extending between the nasal locators and the inlet periphery. In this embodiment, the nasal locators have a preferred thickness of about 0.1 mm to about 0.2 mm. Alternatively, the thickness of the nasal locators may be less than about 0.2 mm such as, for example, about 0.05 mm.

Preferably the change in thickness from one region of the seal to another occurs gradually. For example, the thickness of the seal changes gradually from thickened portion 1118 to thinner portion 1119. Similarly, the thickness of the seal changes gradually from thickened portion 1110 to thinner portion 1119.

Figure 16:
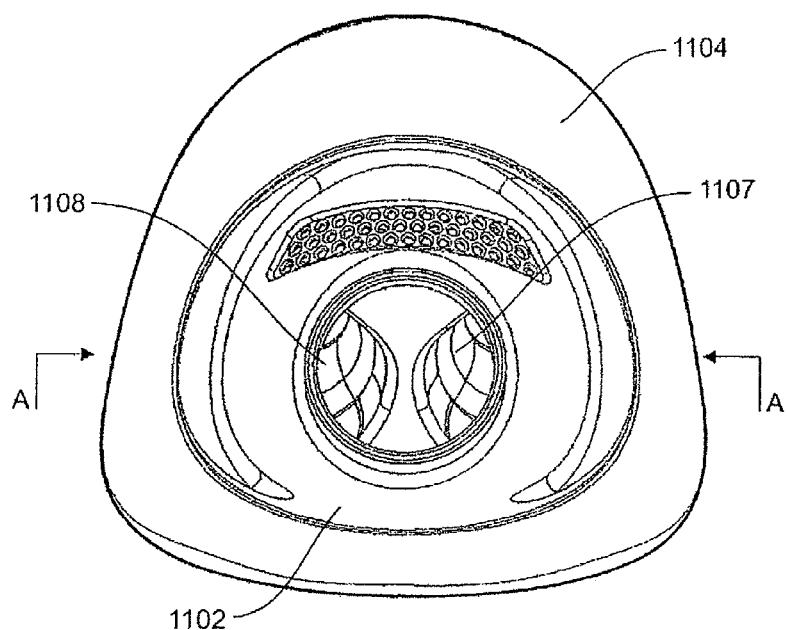
FIG. 16 is a front view of the frame and seal body of the interface of FIG. 13.
Figure 17:
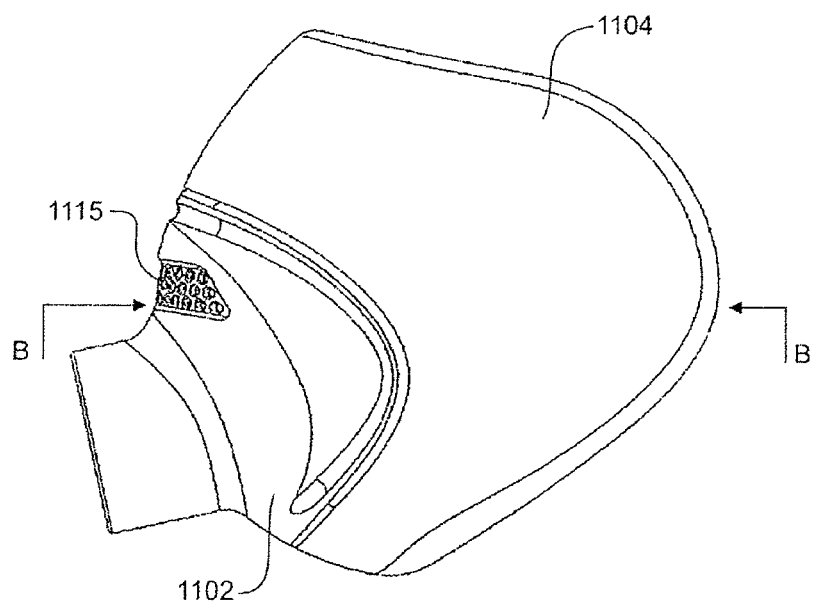
FIG. 17 is a side view of the frame and seal body of the interface of FIG. 13.
Figure 20:
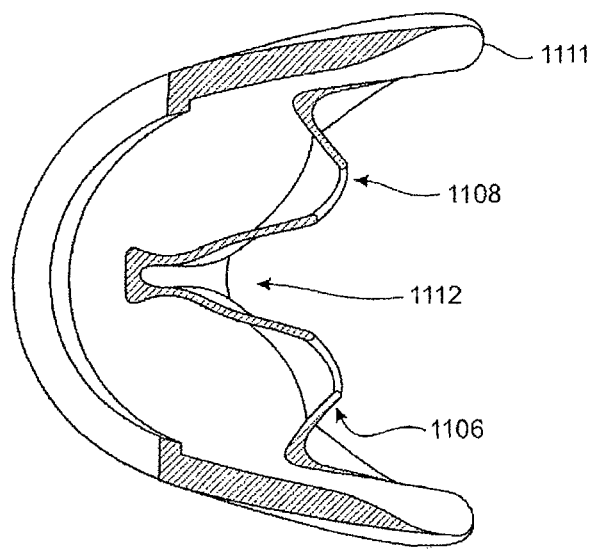
FIG. 20 is a cross-section of the seal body through AA of FIG. 16.

Referring now to FIG. 20, which shows the seal 1101 in cross-section through AA of FIG. 16. This figure shows an alternative view of the seal 1101 showing the varying thicknesses of parts of the seal. In particular, the inlet periphery 1110 and nasal locators 1106, 1108 are thick in cross-section compared to the outer periphery 1111. At least in the lateral direction, the thickened region 1110 adjacent the inlet extends for at least half of the distance from the inlet to the outer peripheral edge 1121. In the upward direction the thickened region extends at least half the distance from the inlet to the top peripheral edge 1123. In the downward direction the thickened region extends at least half the distance to a lower face portion 1125. The areas of the seal between the nasal locators 1106, 1108, generally indicated as 1112, are also thicker in cross-section to provide additional stability in these areas for the nasal locators.

Figure 21:
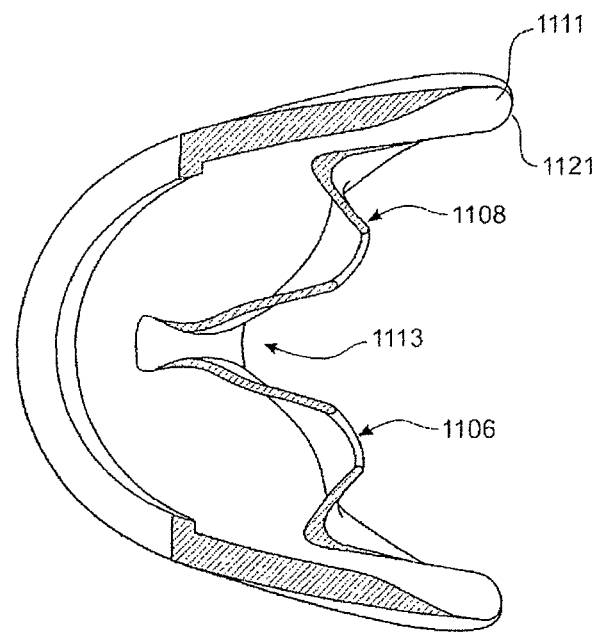
FIG. 21 is an alternative embodiment of a seal body of the interface.

In FIG. 21, an alternative embodiment of the seal is shown. In this alternative embodiment the areas between the nasal locators, indicated as 1113, are substantially thinner in cross-section than that of the inlet periphery 1110 and the nasal locators 1106, 1108. This configuration would provide additional flexibility between the nasal locators 1106, 1108.

Figure 22:
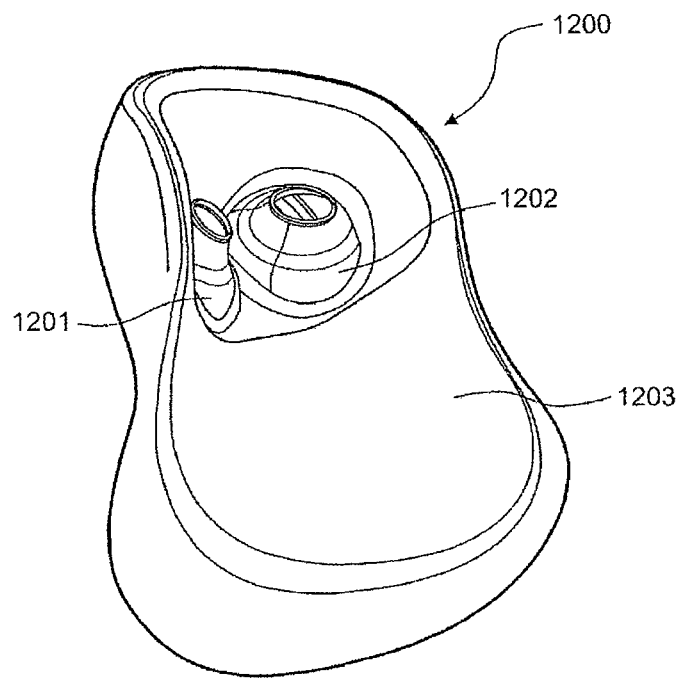
FIG. 22 is yet a further embodiment of a seal body of an interface.

A yet further embodiment of a seal, which is arranged and configured in accordance with certain features, aspects and advantages of the present invention, is shown in FIG. 22. Here the seal is an inflatable type but the seal extends down to occlude the user's mouth in use. This seal 1200 has nasal locators 1201, 1202 and is received in a frame similar to that described in any of the embodiments detailed above. The seal 1200 has an extension 1203 that goes over the user's mouth to create a seal and to reduce mouth leaks.

Figure 23:
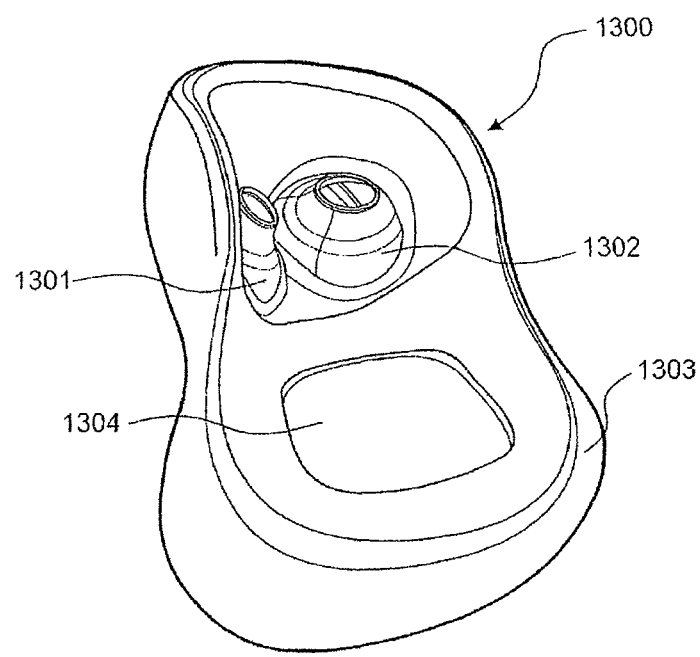
FIG. 23 is another embodiment of a seal body of an interface.

Another embodiment of a seal, which is arranged and configured in accordance with certain features, aspects and advantages of the present invention, is shown in FIG. 23. This seal 1300 is of the same general form as that in FIG. 22, with nasal locators 1301, 1302 and a mouth covering extension 1203, but includes an outlet 1304 directed to the user's mouth to allow gases to be delivered simultaneously to the user's mouth as well as the user's nasal passages through the nasal locators 1301, 1302.

FIGS. 24 to 29 show various head straps that might be used with any of the embodiments of the interfaces described herein.

Figure 24:
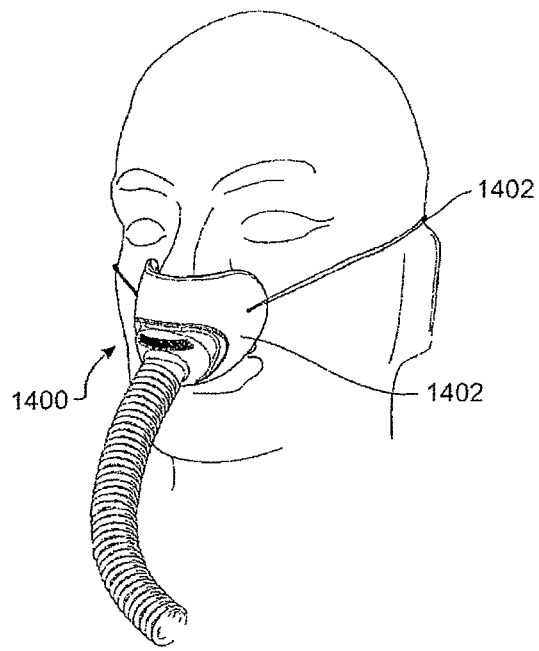
FIG. 24 shows a first embodiment of a head strap that may be used with an interface.
Figure 24A:
FIGS. 24a and 24b show two alternative cross-sections of the head strap of FIG. 24.
Figure 24B:
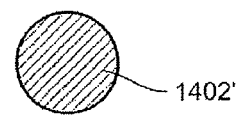

FIG. 24 shows a single head strap 1402 attached to the interface 1400, particularly to the flexible and inflatable seal 1401, by any suitable structure. The strap 1402 may be a hollow tube 1402 as shown in FIG. 24*a* or a solid tube 1402' as shown in FIG. 24*b*. The hollow tube could, for example, be an extended silicone tube, with a diameter between about 3 mm and about 6 mm and, where hollow, the tube may have a wall thickness of about 0.2 mm to about 1 mm.

Figure 25:
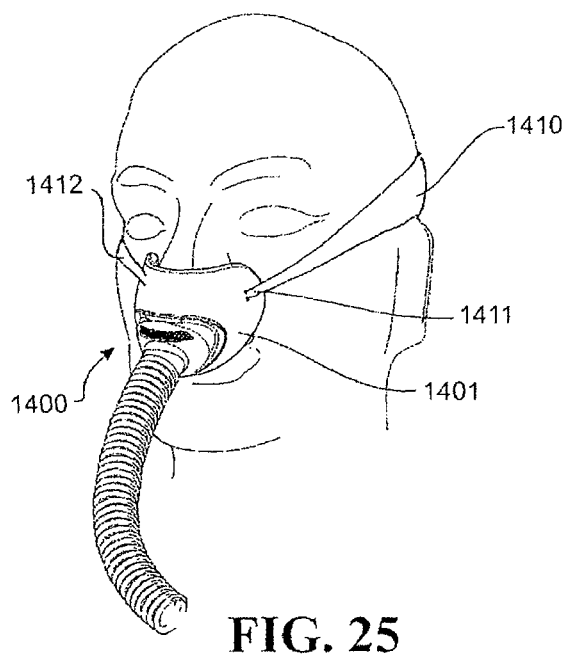
FIG. 25 shows a second embodiment of a head strap that may be used with an interface.
Figure 25A:
FIGS. 25a and 25b show two alternative cross-sections of the head strap of FIG. 25.
Figure 25B:
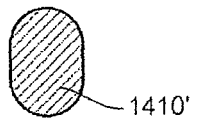

FIG. 25 shows a single head strap 1410 attached to the interface 1400, particularly to the flexible and inflatable seal 1401 by any suitable structure. The strap 1410 may be a hollow elongated tube 1410 as shown in FIG. 25*a* or a solid elongated tube 1410' as shown in FIG. 25*b*. The strap is preferably thinner in width at its ends 1411, 1412 that attach to the seal 1401 and thicker in width at its midpoint that sits at the back of the user's head in use.

FIG. 26 shows a double head strap 1420 attached to the interface 1400. The strap 1420 extends about the user's ears and has two attachment points on each side of the seal 1401 where the strap attaches to the seal 1401.

FIGS. 27 and 27*a* show an extendible head strap 1430 attached to the interface 1400. The strap 1430 has an area 1431 that can be extended and contracted to better fit the strap to the user's head.

FIG. 28 shows an alternative head strap 1440 attached to the interface 1400, particularly to the seal 1401. The head strap 1440 preferably includes side straps 1441 having areas of rigidity 1442, 1443, to provide additional stability to the side straps 1441. The head strap 1440 also preferably includes a top strap 1444 and a back strap 1445 that each extends over the head or behind the head respectively. This head strap is detailed further in U.S. patent application Ser. No. 12/307,993, which is hereby incorporated by reference in its entirety.

FIGS. 29 and 29*a* shows yet a further alternative head strap 1450 attached to the interface 1400, particularly to the seal 1401. The head strap 1450 is curved and has partitions 1451 that provide additional support or rigidity to the strap.

The head straps detailed above may be formed of any appropriate material, such as, flexible plastics, silicone, laminated fabrics, or other appropriate materials, for example but without limitation.

Figure 30:
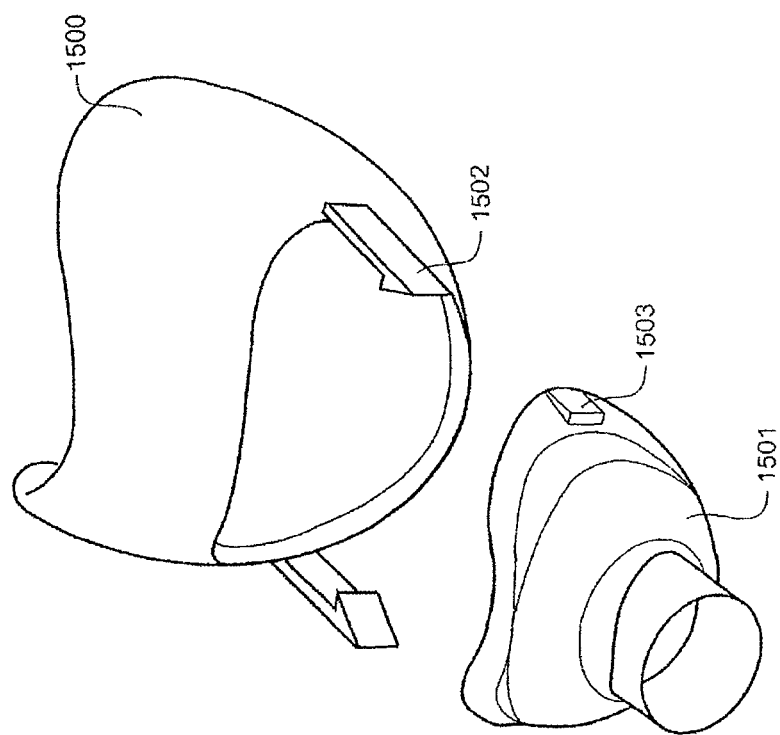
FIG. 30 shows a first embodiment of the connection between a seal body and frame of the interface.

FIGS. 30 to 33 show various ways in which an interface frame may be attached to an inflatable seal body. In FIG. 30, the seal body 1500 includes overmoulded or bonded rigid plastic barbs 1502. The barbs 1502 clip into correspondingly shaped recesses 1503 formed in the frame 1501 and hold the seal body 1500 in sealing engagement with the frame 1501.

Figure 31:
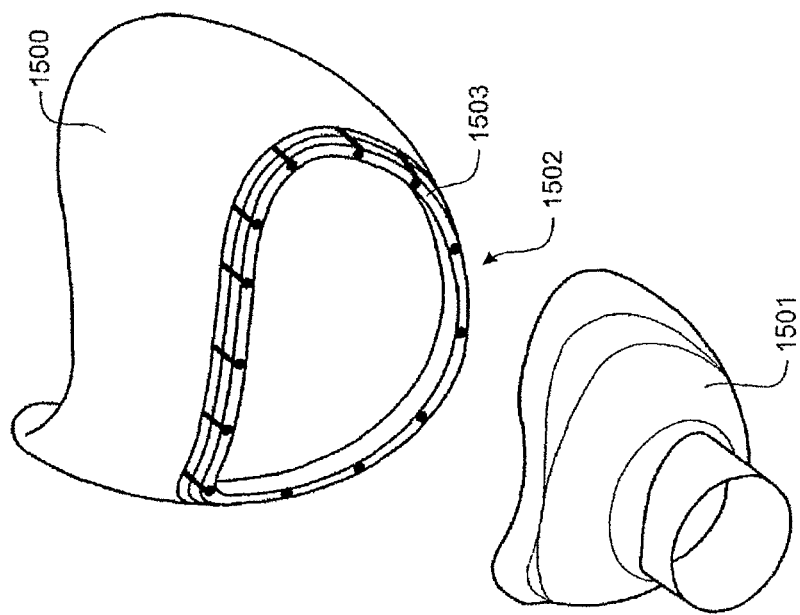
FIG. 31 shows a second embodiment of the connection between a seal body and frame of the interface.

In FIG. 31, the seal body 1500 has a periphery 1512 that is formed with a overmoulded or bonded rigid plastic looped clip 1513 that clips to the frame 1501. Further details of such a clipping mechanism are described in U.S. patent application Ser. No. 12/502,528, which is hereby incorporated by reference in its entirety.

Figure 32:
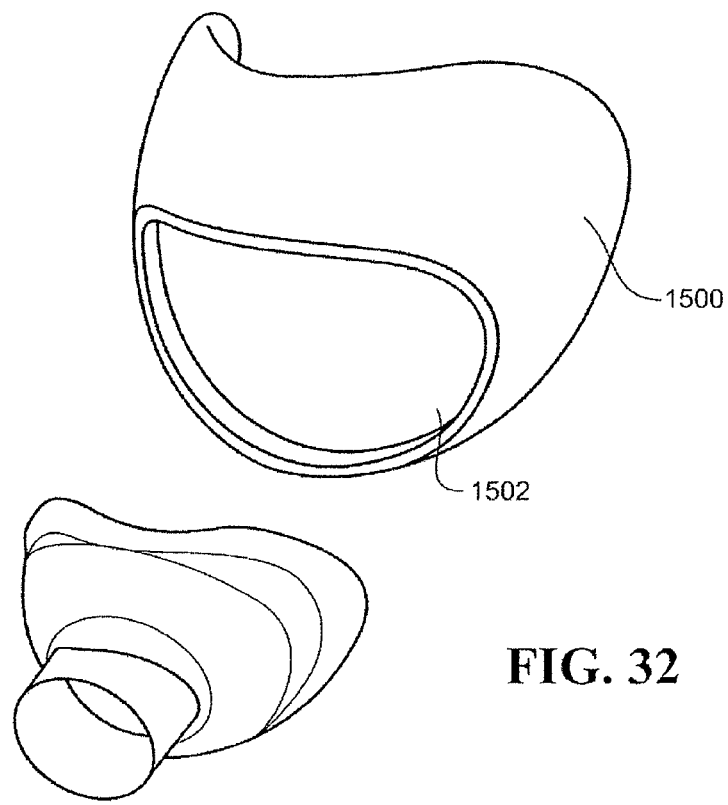
FIG. 32 shows a third embodiment of the connection between a seal body and frame of the interface.

As shown in FIG. 32, the seal body 1500 may have an inlet 1522 that has a stretch interference fit about the frame 1501. The frame preferably has a groove 1523 and a raised edge 1524 that allows the inlet 1522 to engage with the frame.

Figure 33:
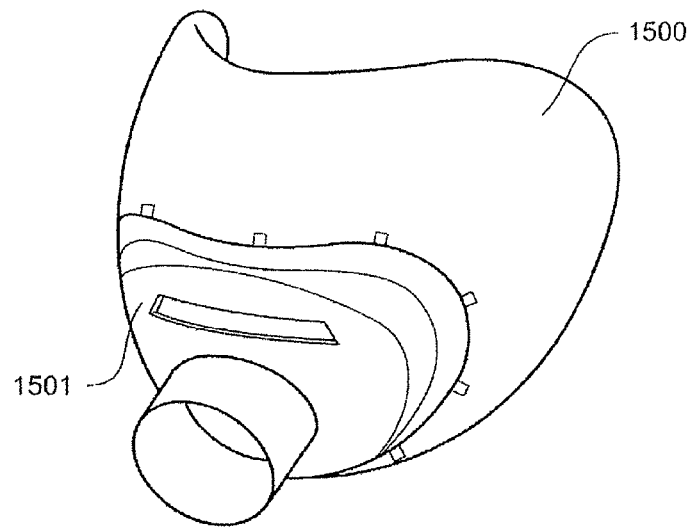
FIG. 33 shows a forth embodiment of the connection between a seal body and frame of the interface.

As shown in FIG. 33, a seal body 1500 may be permanently attached to the frame 1501 by overmoulding or by bonding, for example but without limitation.

FIGS. 34 to 40 illustrate various ways in which the tubing (1112, see FIG. 13) extending from the interface 1100 may be secured to a user. The advantage of securing the tubing to the user is to take at least a portion of the weight of the tubing off of the interface, reducing the possibility of the interface being pulled from the user's face. Each of the braces described below can be made from fabric straps. It is preferred that the fabric is a breathable type material but other appropriate fabrics may be used. Preferably, the tubing is fixed to the brace by way of a clip or pin, for example but without limitation.

Figure 34:
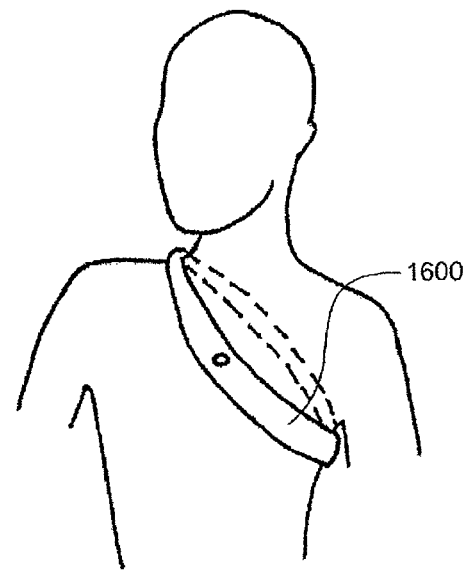
FIG. 34 shows a first embodiment of a brace that may be used with the interface to fix tubing connected to the interface to the user.

In FIG. 34, a brace 1600 is shown that is made from a looped strap of fabric that in use is placed about the user's head and one shoulder.

Figure 35:
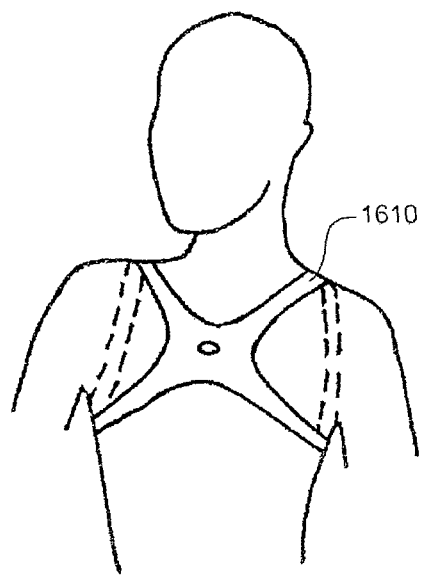
FIG. 35 shows a second embodiment of a brace that may be used with the interface to fix tubing connected to the interface to the user.

In FIG. 35, a brace 1610 is shown that is formed in a central cross across the user's chest and that is braced around each of the user's arms.

Figure 36:
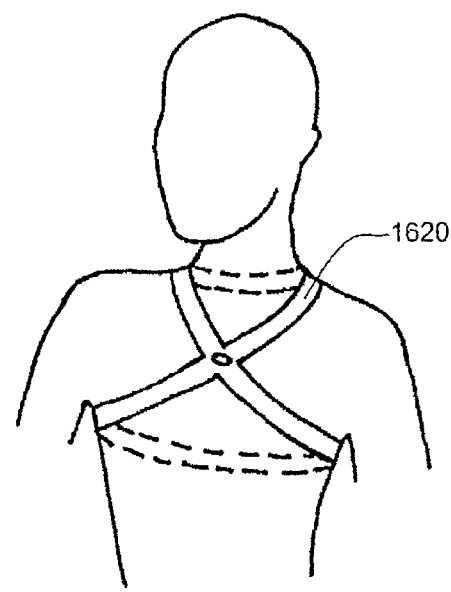
FIG. 36 shows a third embodiment of a brace that may be used with the interface to fix tubing connected to the interface to the user.

In FIG. 36, a brace 1620 is shown that has a central cross of straps across the user's chest but that is braced across the user's neck and back.

Figure 37:
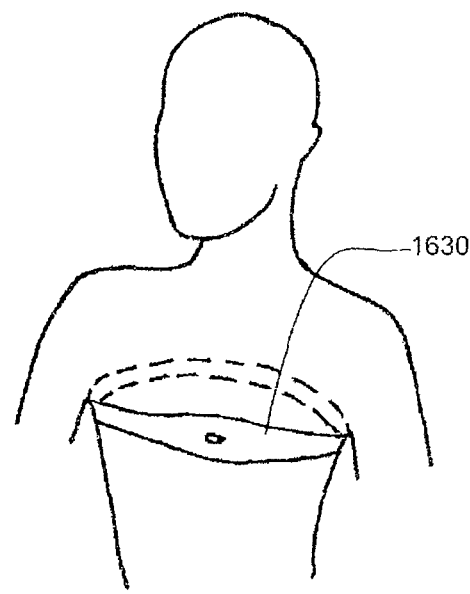
FIG. 37 shows a fourth embodiment of a brace that may be used with the interface to fix tubing connected to the interface to the user.

In FIG. 37, a brace 1630 is shown that could be used to secure tubing to the user wherein the brace 1630 is formed from the looped strap that extends about the user's chest and under their arms.

Figure 38:
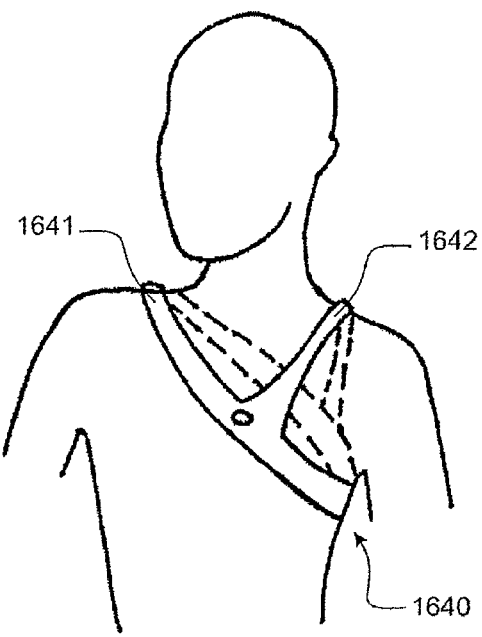
FIG. 38 shows a fifth embodiment of a brace that may be used with the interface to fix tubing connected to the interface to the user.
Figure 39:
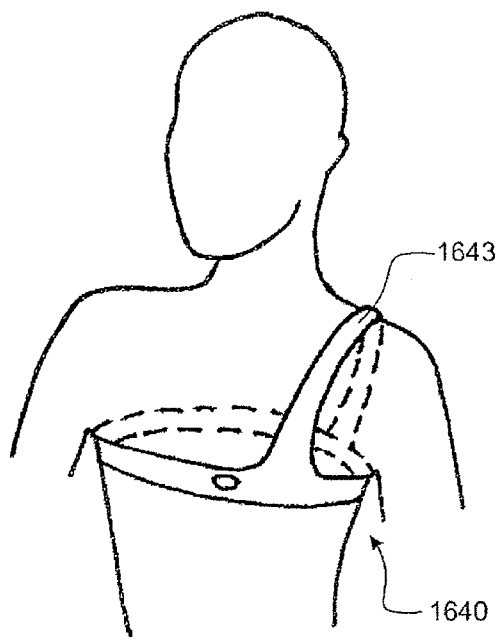
FIG. 39 shows a sixth embodiment of a brace that may be used with the interface to fix tubing connected to the interface to the user.

As shown in FIG. 38 or 39, a brace 1640 may additionally include two shoulder straps 1641, 1642 or simply one shoulder strap 1643.

Figure 40:
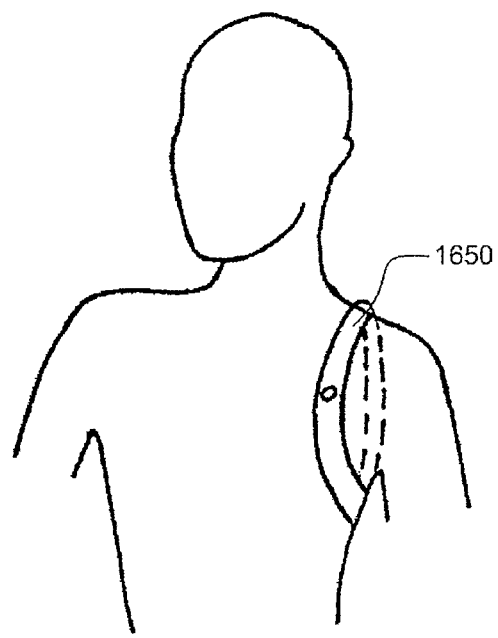
FIG. 40 shows a seventh embodiment of a brace that may be used with the interface to fix tubing connected to the interface to the user.
Figure 41:
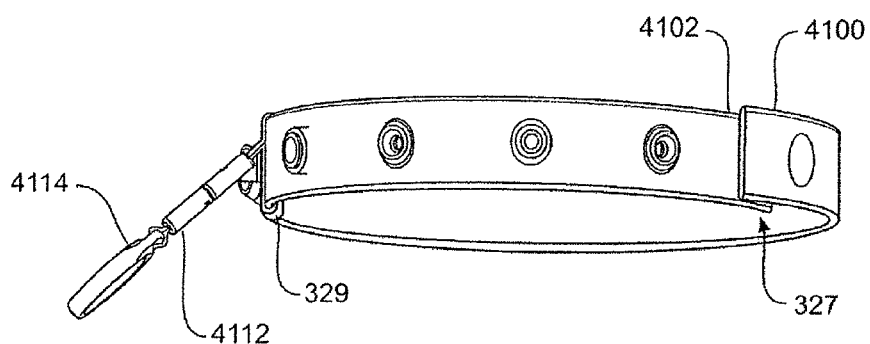
FIG. 41 is a perspective view of a supporting collar.
Figure 42:
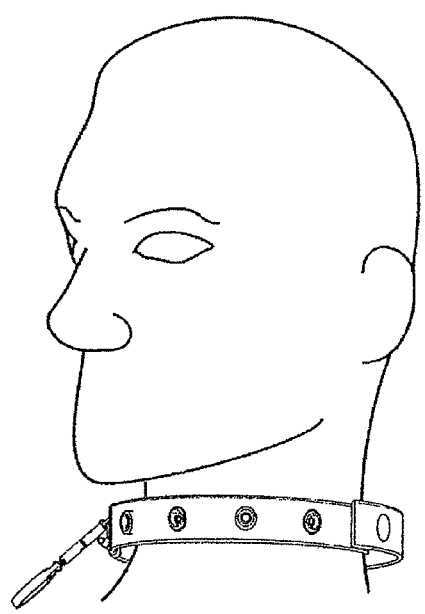
FIG. 42 is a perspective view of a patient wearing the supporting collar of FIG. 41.
Figure 43:
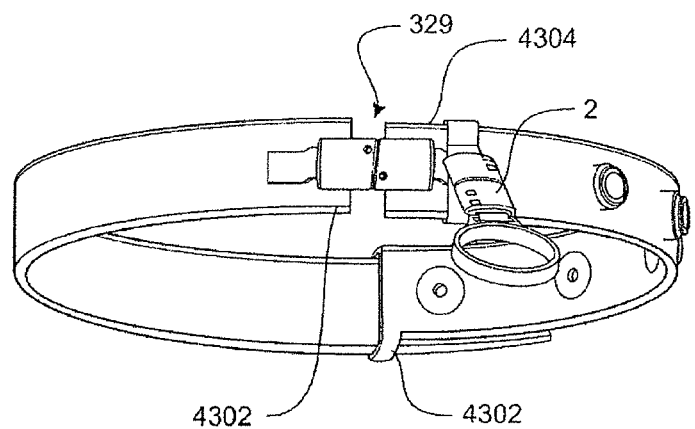
FIG. 43 is a perspective view of the collar of FIG. 41 from a different angle.
Figure 44:
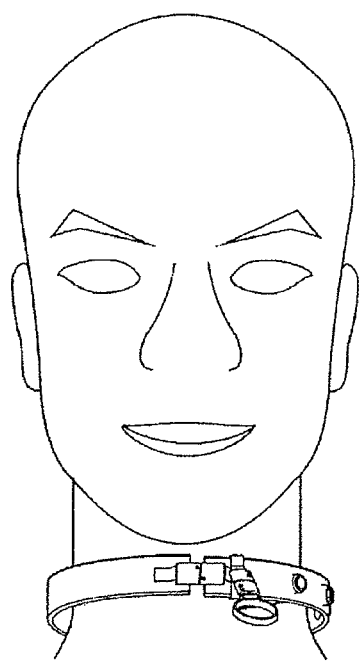
FIG. 44 is a front view of a patient wearing the collar of FIG. 41.

As shown in FIG. 40, a brace 1650 may be used that fits in use about the user's shoulder or upper arm.

Figure 56:
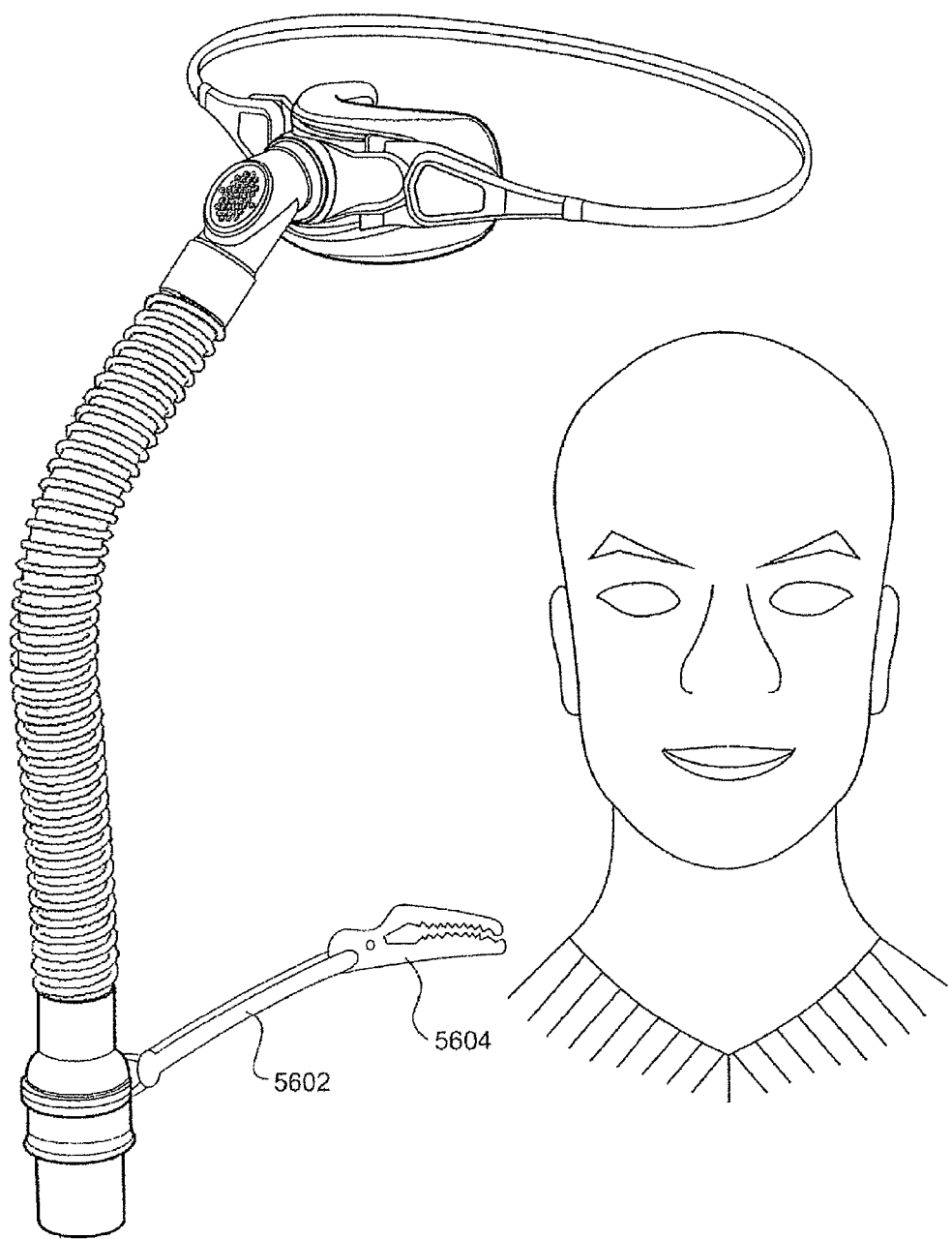
FIG. 56 is a perspective view of an interface including an alternative arrangement for supporting the conduit from the patient.
Figure 57:
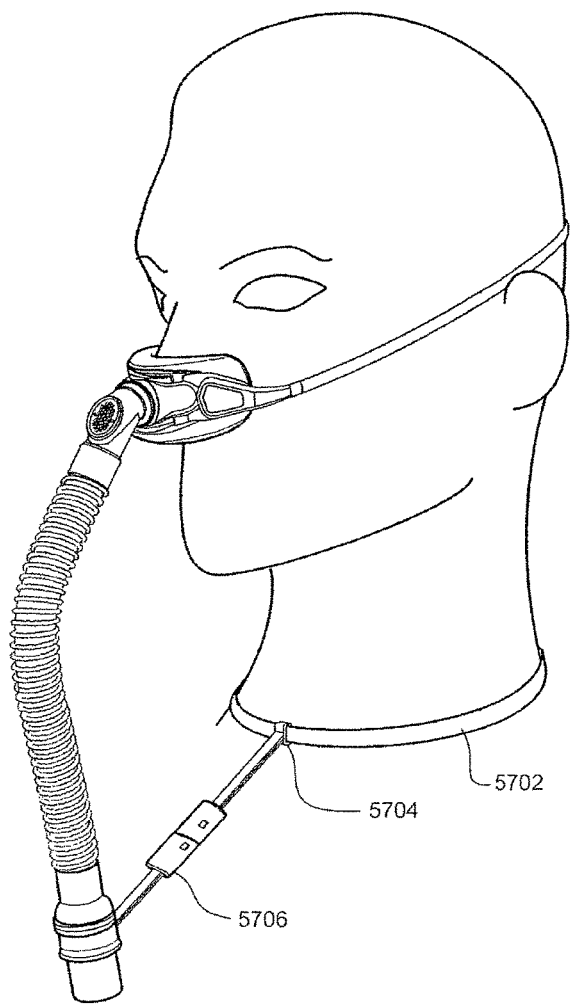
FIG. 57 is a perspective view of a patient wearing an interface including a further alternative arrangement for supporting the conduit on the patient.
Figure 58:
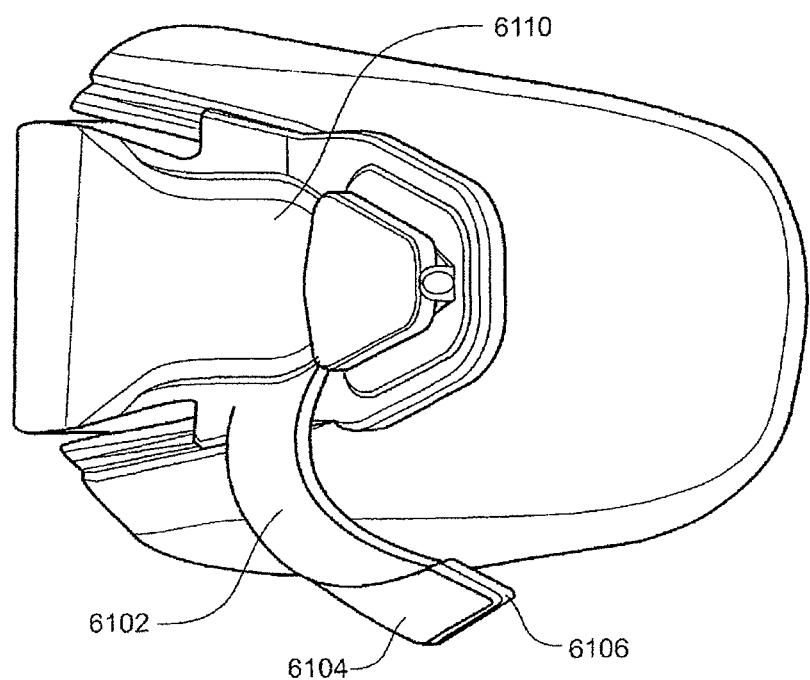
FIG. 58 is a side elevation of a frame and seal, the frame incorporating depending lip stabilisers.
Figure 59:
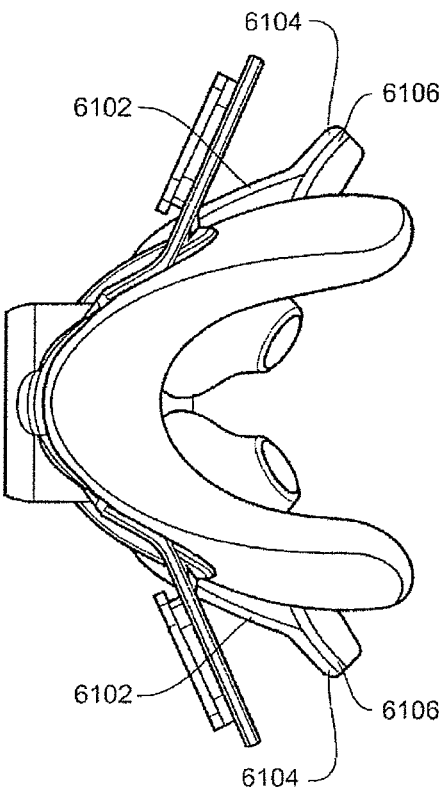
FIG. 59 is a top view of the frame and seal of FIG. 58.
Figure 60:
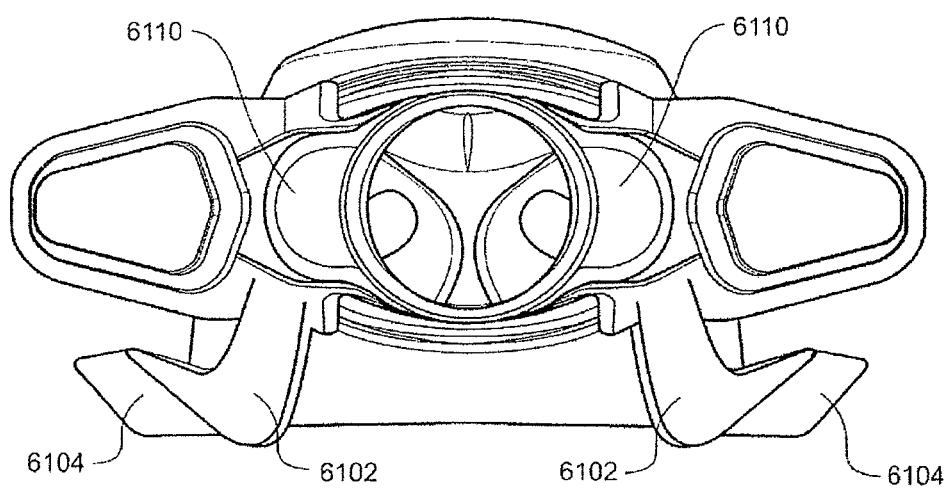
FIG. 60 is a front view of the frame and seal of FIG. 58.
Figure 61:
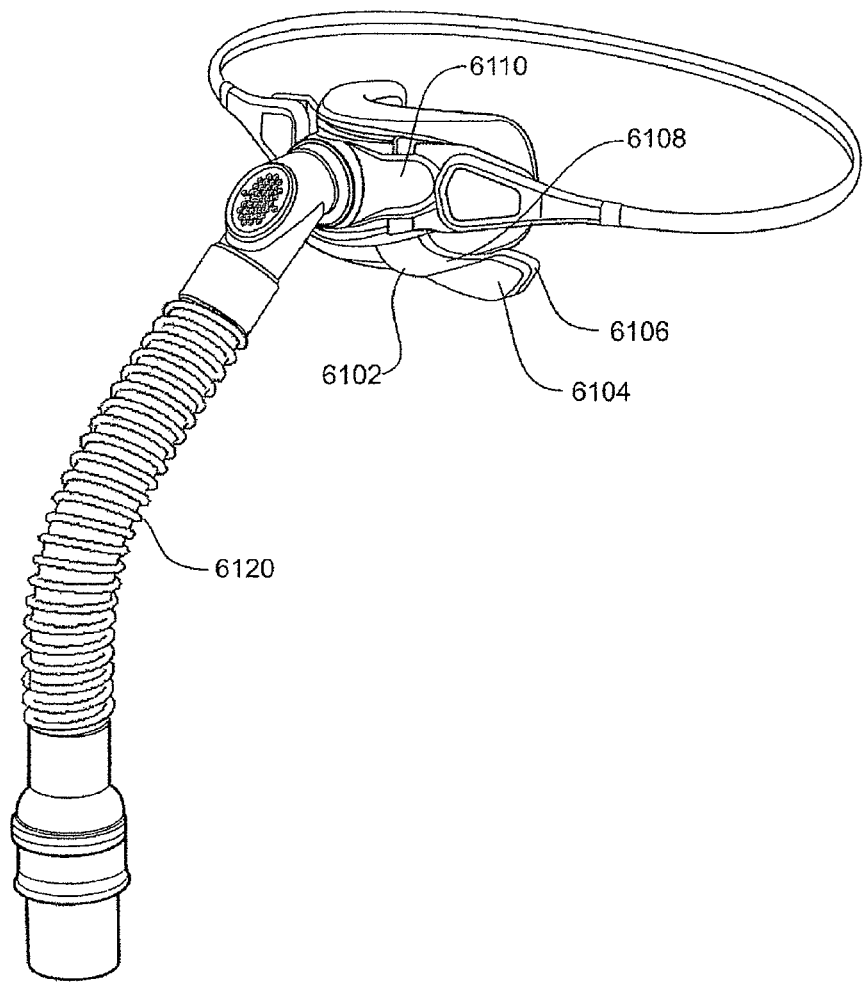
FIG. 61 is a perspective view of an interface incorporating the frame and seal of FIG. 58.

Additional tube support arrangements will be described with reference to FIGS. 41 to 57. FIGS. 41 to 51 describe a supporting collar intended to be worn around the neck of the user, and to which the tube may be supported by a tether. FIGS. 52 to 55 describe aspects of a tether that might be used with such a collar, or that might be used with other arrangements for securing one end of the tether to the patient. FIGS. 56 and 57 illustrate two such arrangements for securing a tether to the patient. FIGS. 34 to 40 illustrate other arrangements for securing such a tether to the patient.

FIGS. 41 to 45 illustrate in further detail the collar previously described in broad terms in relation to FIGS. 3A to 3C. The illustrated collar includes an adjustable connection 327 and a secondary connection 329. The adjustable connection operates between a first end of the collar 4100 and a second end 4102. The adjustable connection 327 allows the user to set the amount of overlap of the ends 4100 and 4102. FIGS. 41 to 45 illustrate an adjustable connection 327 in the form of a dome fastener system. One fastener portion 4104 is fixed to the first strap end 4100. A number of complementary fastener portions 4106 are provided spaced along the second strap end 4102. Engaging the fastener 4104 with one of the series of fastener portions 4106 sets the overlap of end 4100 relative to end 4102. The fastener portions 4106 may be spaced at intervals between about 2 cm and about 5 cm, preferably between about 3 cm to about 4 cm. This provides a degree of variation in the circumference of the collar in increments of between about 3 cm and about 4 cm.

Preferably, the outer overlapping end 4100 includes a single connector portion and the inner strap end includes a series of outwardly-facing second connector portions. According to this arrangement, no connector portion faces toward the patient neck. Accordingly, the internal surface of the collar is free of projections.

The connector portions may be portions of, for example, a dome fastener of known type.

The extreme end of inner end 4102 may include an outwardly projecting loop engaging over the overlapping portion of the collar strap. This loop 4302, shown only in FIG. 43, would align the free end of underlapping end 4102 with the overlapping portion of the collar when the collar is set on tighter sizes.

Alternative connectors for the adjustable connection are illustrated in FIGS. 46 to 49. The dome fastener connection is illustrated in more detail in FIG. 46.

Figure 47:
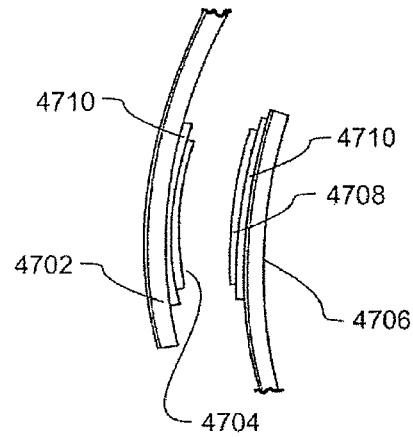
FIG. 47 is a top view of a portion of the collar including an alternative fastener.

An alternative fastener using engaging magnets is illustrated in FIG. 47. The outer strap end 4702 includes an inwardly-facing magnet portion 4704. The inner strap end 4706 includes an outwardly-facing magnet portion 4708. The inwardly-facing magnet portion 4704 preferably is magnetized to a first polarity facing inwards. The outwardly-facing magnet portion 4708 is preferably magnetized with a complementary polarity facing outwards. A series of outwardly-facing magnets 4708 would be spaced along the outer surface of the inner strap portion 4706.

The magnet portions may be fixed to a base portion 4710 which in turn may be fixed to the strap. For example, the magnets may be glued to a substrate material that can be stitched to the strap. Alternatively, magnets might be moulded to include holes to allow the magnets to be directly stitched to the strap.

The magnet 4704 could be replaced by a magnetic material which would be attracted by magnets 4708 but not be a magnet itself. Alternatively, magnets 4708 could be replaced by portions of a material that is magnetic but not itself a magnet. By way of example, the magnets may be ferrite or rare earth, while magnetic materials might be small sections of steel. Ferrite powder bonded with a flexible polymer may allow the magnets to be flexible while maintaining sufficient strength to secure the collar.

Figure 48:
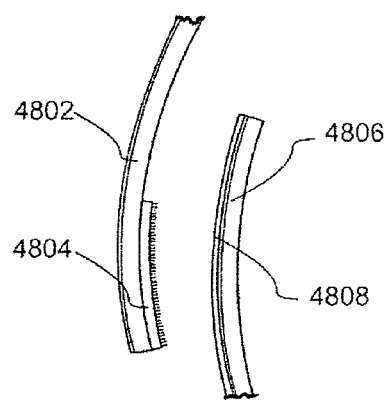
FIG. 48 is a top view of a portion of the collar including an alternative fastener.

FIG. 48 illustrates the adjustable connection being made by a hook and loop fastener system. For example, the outer end portion 4802 may include a short section 4804 of a material with projecting hooks. The inner strap end 4806 may include an outwardly-facing section 4808 covered with loops to which the hooks may engage and disengage. Suitable hooks and loop fastener material is sold under the Velcro brand.

The outwardly facing loop material may be stitched to the collar strap, or the collar strap may be formed from a material that integrally includes the loops. The length of the loop portion 4808 is much greater than the length of the hook portion 4804 and preferably extends a length equivalent to the adjustment desired to be available to the collar. For example, the loop fastener material would have a length of about 15 cm along the collar strap.

Figure 49:
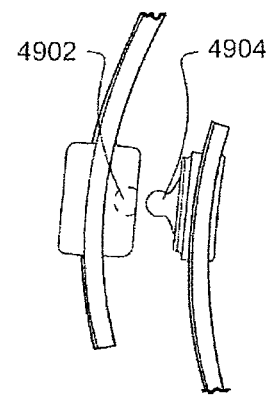
FIG. 49 is a top view of a portion of the collar including a further alternative fastener.

FIG. 49 illustrates an alternative mechanical fastener similar to the dome fastener. This type of dome fastener includes a smaller receiving aperture 4902 on the female portion and smaller projecting pins 4904 on the male portion.

Referring back to FIGS. 43 to 45, the collar preferably includes a second releasable connection 329 between a third end 4302 and a fourth end 4304. Thus, the overall ring of the collar is divided into two separate strap sections. Each strap section includes at one end part of the adjustable connections 327 and at the other end part of the second connection 329.

Preferably, this second connection is not adjustable. This second connection 329 is intended to be engaged and disengaged at each use of the collar. The adjustable connection can be adjusted to the correct length and set, and the second connection 329 can be used to secure and release the collar.

Figure 50A:
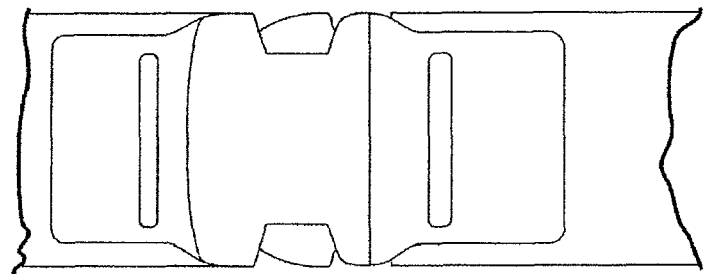
FIG. 50A is a side view of a portion of the collar including a securing clip in an engaged configuration.
Figure 50B:
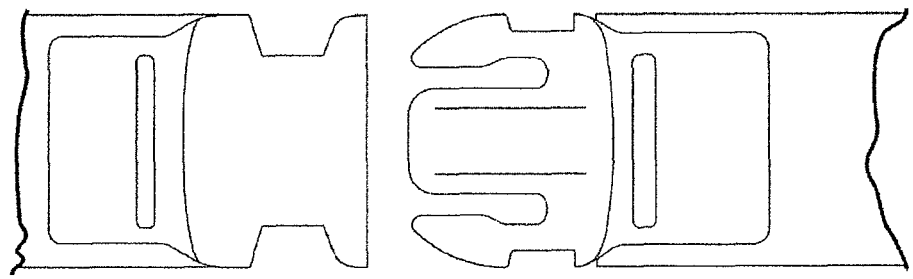
FIG. 50B is a side view of the portion of the collar from FIG. 50A in a disengaged condition.

This second connection 329 may be formed by any suitable means, including the examples illustrated in FIGS. 46 to 49, or including a plain releasable fastening clip such as illustrated in FIGS. 50A and 50B (50A in the connected condition and 50B in the open condition), or a breakaway connector which releases upon application of tension in a predetermined range.

Figure 45:
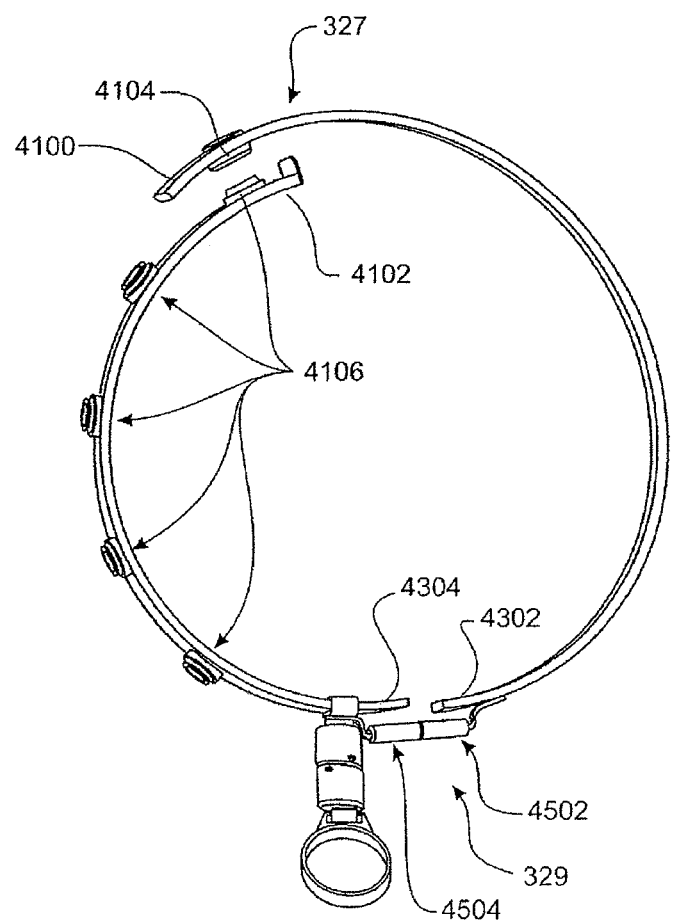
FIG. 45 is a top view of the collar of FIG. 41.
Figure 46:
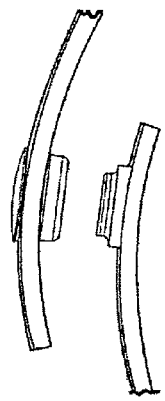
FIG. 46 is a top view of a portion of the collar of FIG. 41 illustrating a dome fastener connector.

The connection 329 illustrated in FIG. 45 includes a breakaway connector having a first body portion 4502 secured to strap end 4302 and a second body portion 4504 secured to fourth strap end 4304. The first and second body portions each include a projecting tang and a socket. The projecting tang of one body is complementary with the socket of the other body. The projecting tang and socket preferably have an interference fit. The amount of interference and the force required to pull the tang from the socket defines the release force for the breakaway clip.

Figure 51A:
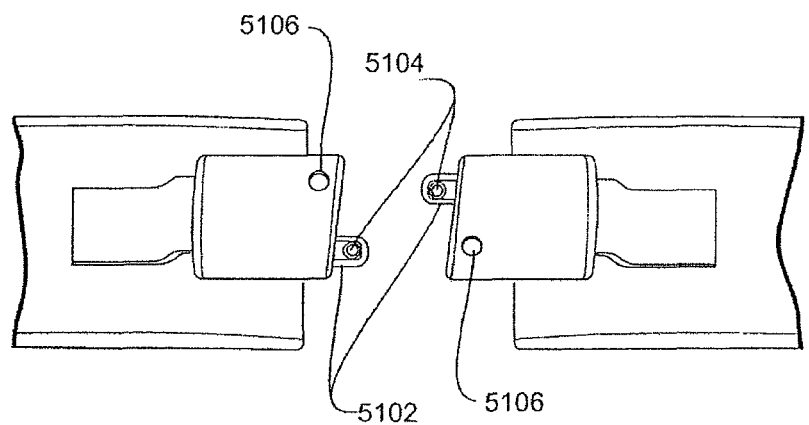
FIG. 51A is a side view of a portion of the collar including a securing clip according to an alternative embodiment in a disengaged condition.
Figure 51B:
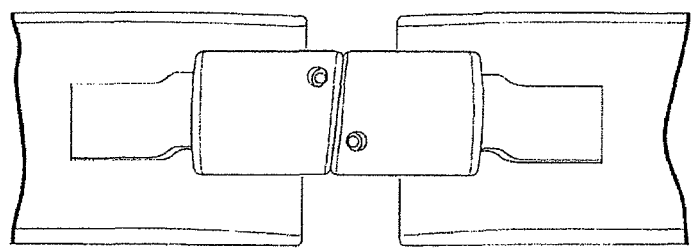
FIG. 51B is a side view of the portion of the collar of FIG. 51A in an engaged condition.

This preferred breakaway clip is illustrated in more detail in FIGS. 51A and 51B. In FIG. 51A, the clip is illustrated in the open configuration where a tang 5102 projects from each clip body portion and each tang 5102 includes a small lateral projection 5104. The socket in each body portion of the clip includes a lateral aperture 5106. When the tang 5102 is pushed into the socket, the projection 5104 extends into the aperture 5106. The interference fit is provided by engagement of the projection 5104 in the aperture 5106. This connector is shown in its engaged condition in FIG. 51B.

Referring again to FIGS. 41 to 45, a tether extends from the collar. The tether 4112 is connected with the collar at one end and to an engaging clip 4114 at its free end. The engaging clip 4114 allows connection with the supply conduit for the patient interface. The engaging clip 4114 is illustrated in greater detail in FIG. 55, where an enlarged view of its fitting with the cuff of the conduit is illustrated. The preferred connector includes an open ring which fits over a sleeve portion of the cuff and is held in place between a flange 5502 of the cuff and a flange 5504 of a swivel conduit connected to the cuff.

Figure 52:
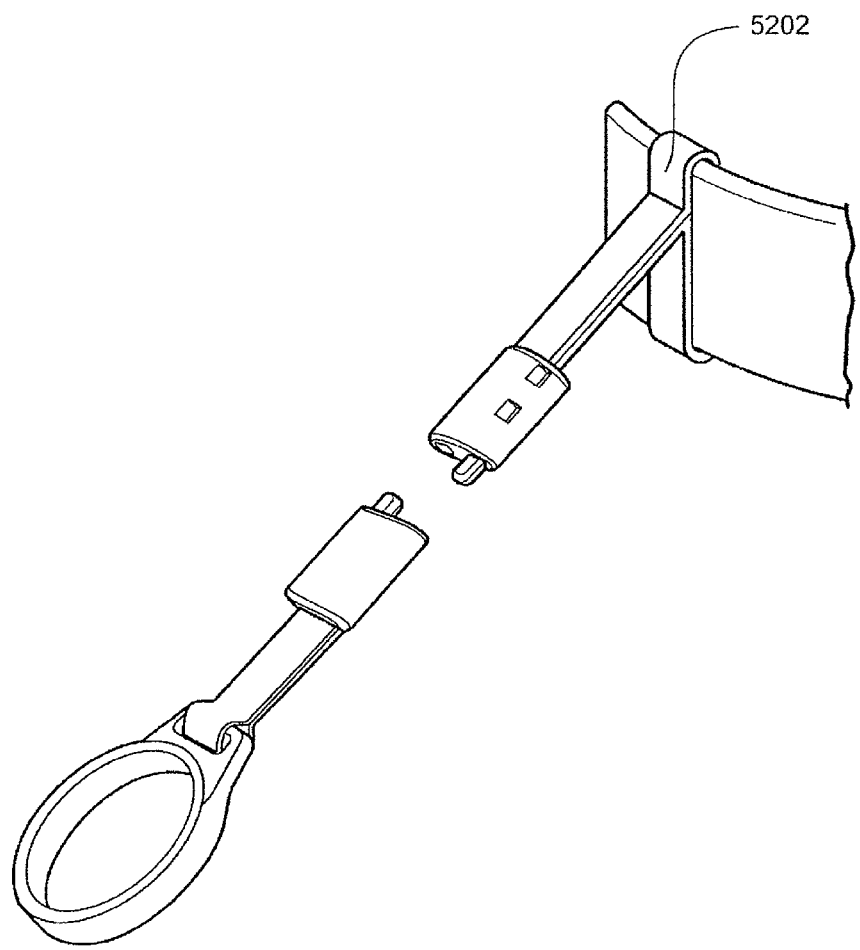
FIG. 52 is a perspective view of a tether depending from a portion of the collar, with the tether including a quick disconnect connector.
Figure 54A:
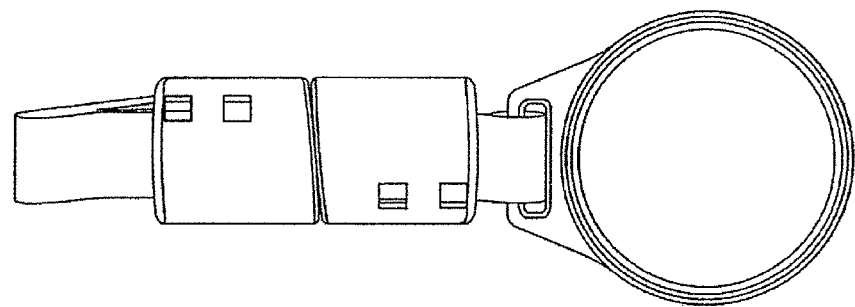
FIG. 54A is a top view of a tether similar to the tether of FIG. 51B, but of minimal length.
Figure 54B:
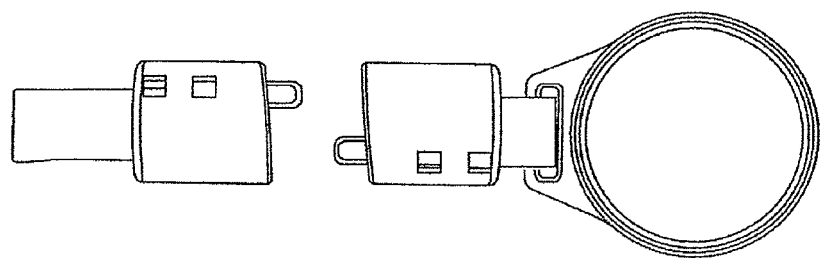
FIG. 54B is a top view of the tether of FIG. 54A with the quick release connector disengaged.
Figure 54C:
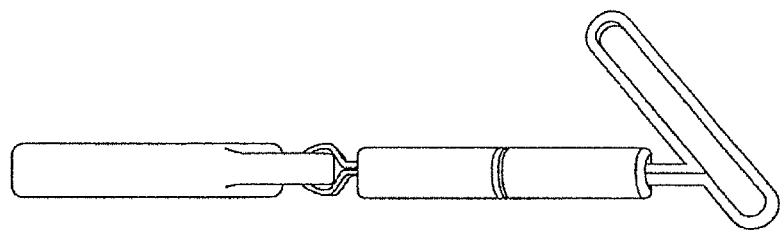
FIG. 54C is a side view of the tether of FIG. 54A.
Figure 55:
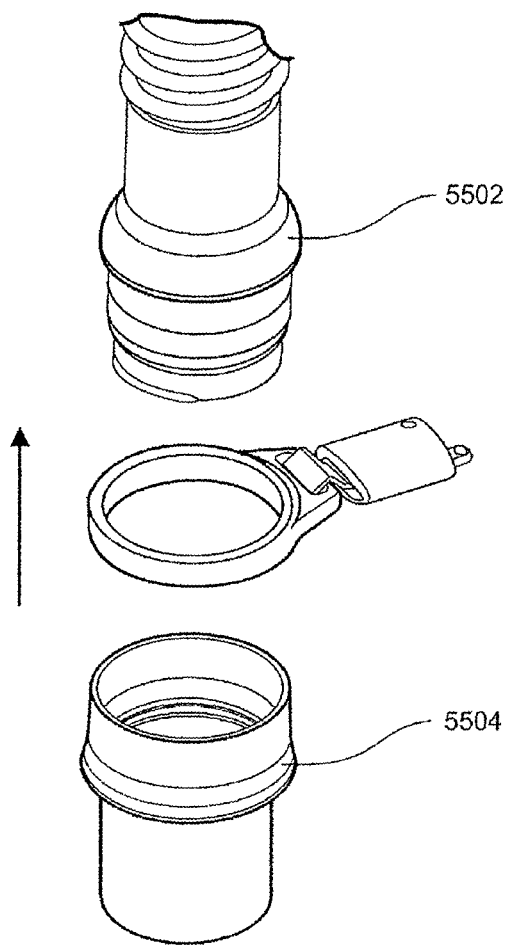
FIG. 55 is an exploded view illustrating connection of a ring of the tether from the supporting collar to a conduit.

The preferred tether includes a breakaway clip at some position along its length between the connection to the collar and the conduit connector. The breakaway connector may be of the form described already with reference to FIGS. 51A and 51B. That form of breakaway connector is illustrated in FIGS. 52, 54A and 54B.

The breakaway connector may also include a swivel, such that the collar does not need to be correctly oriented relative to the conduit before donning the patient interface. In this case, the breakaway connector may include a socket portion 5302 and a male portion 5304, with the male portion 5304 being rotationally symmetric. For example, the male portion 5304 may include a projecting knob 5306 with an enlarged end 5308. The socket 5302 would include projecting portions or an annular projecting portion around the internal circumference adjacent the open end. The socket 5302 may be made in two pieces subsequently secured together to produce this projecting lip or lips. The socket portion 5302 may be open at its other end 5310 so that the connector portion 5302 can be formed in one piece. This end may accommodate an end of a strap portion 5312 of the tether.

A swivel may be included at another location along the tether.

Preferably, the tether is formed with a sliding connector 5202 at one end for connection over the collar. The sliding connector 5202 preferably comprises a moulded loop including straight sections on either side of the web of the collar and joined by transverse sections above and below the collar edge. The loop preferably has a moderately tight fit on the collar so that once moved into a position, it tends to stay in that position but can be moved along the collar upon application of sufficient force. The loop 5202 essentially mirrors the profile of the web of the collar. A tether portion may extend from the loop 5202, preferably being integrally formed with the loop 5202. Preferably, the tether portion and the loop are formed from a flexible resilient material, such as silicone, for example but without limitation.

Another tether portion extends from the quick release connector to the conduit in engagement clip. Again, this may be formed of any suitable material, preferably flexible and preferably a silicone material, for example but without limitation.

The tether may be of fixed or adjustable length. Preferably, the tether may be provided in multiple lengths for selection by a patient. The tether may be of a length between about 3 cm and about 15 cm. A tether at approximately 3 cm is illustrated in FIGS. 54A to 54B, the tether including limited, if any, strap portions. This tether is mostly made by its loop connector to the collar, by the quick release connector and by its connection to the conduit connector.

Figure 53:
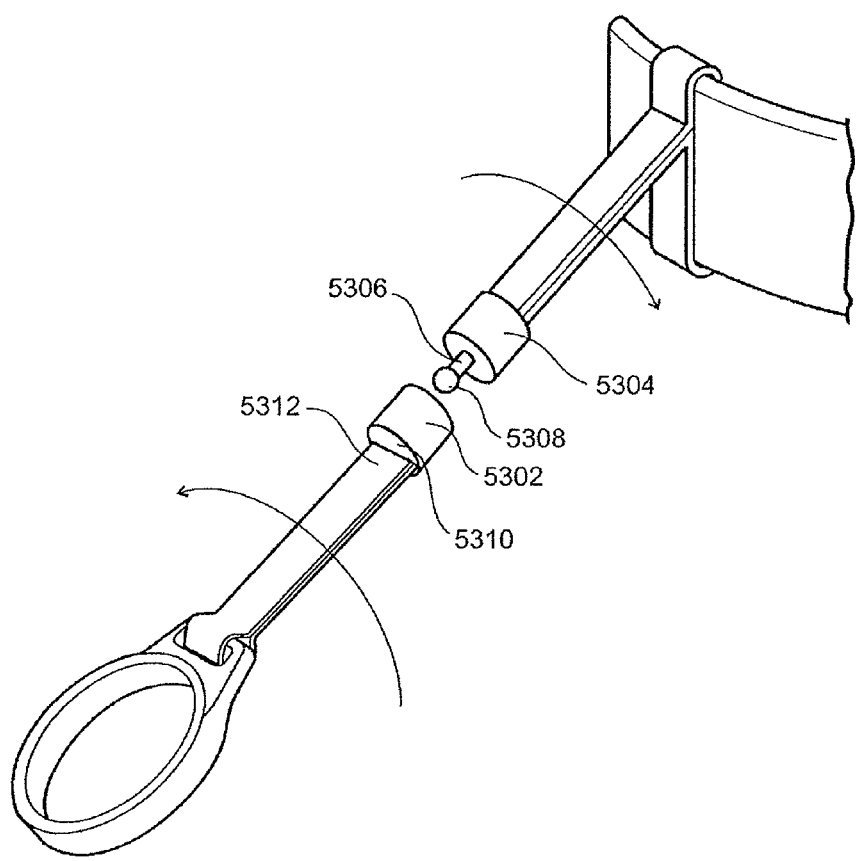
FIG. 53 is a perspective view illustrating a tether depending from the collar, the tether including a quick disconnect connector which can also swivel.

A longer tether is illustrated in FIG. 52 and in FIG. 53, including a substantial strap portion between the connecting loop 5202 and the quick release connector and another substantial strap portion between the quick release connector and the conduit connector. These portions of the tether could be interchanged so that, for example, the strap portion of the tether could be provided entirely to one side or other of the breakaway connector.

FIG. 56 illustrates an alternative support arrangement to the use of a collar. The tether 5602 terminates in a clip 5604 instead of terminating at a connector for the collar. The clip 5604, preferably in the form of a type of peg, alligator clip or other arrangement having gripping jaws, can attach to the neckline or other convenient portion of clothing worn by the patient. Alternative, the tether may be terminated at a connector for connecting to brace structures to be worn by the patient as described earlier.

The tether may or may not include a breakaway connector.

FIG. 57 illustrates another alternative for connection to clothing 5702 on the patient. This illustrates the push clip 5704 connected to the collar line of the clothing and including a breakaway connector 5706.

The preferred collar is constructed from materials comfortable to the wearer. In the simplest form, the collar might be, for example but without limitation, a strap of a soft, flexible material having sufficient stiffness to hold the general collar form, sufficient strength to resist any substantial extension or stretching and comfortable inside surface facing the patient. One suitable material might be, for example but without limitation, a laminated foam material such as Breathoprene, which has a foam web faced on either side with a knitted fabric.

However, the collar can be more resistant to stretch than the Breathoprene material, and more breathable than the Breathoprene material. For comfort against the skin, the collar is preferably faced with a woven, knitted or braided natural fibre fabric such as, for example but without limitation, a braided or knitted tube of cotton or bamboo yarn. To provide form to the collar, the braided or knitted tube can surround a flexible skeleton. The flexible skeleton might comprise a series of hingedly connected frames, or a moulded flexible strap formed with an open framework. Preferably, it comprises a narrow strap of plastic mesh. An example of a suitable mesh is 3MESH, manufacture by Mullter Texti Group of Germany. The open framework or mesh form allows moisture and heat to pass readily through the collar, reducing discomfort of the patient wearing the collar for long periods.

The collar strap is preferably about 3 cm to about 6 cm wide and between about 3 mm and about 8 mm thick.

One preferred simple head strap is illustrated in FIGS. 3A to 3C. It includes a single, non-bifurcated strap terminated with a connector at either end. The strap could be permanently connected to either end of the frame, but preferably the connectors are configured to be removable from the body of the mask. Another example of a preferred headstrap is illustrated in FIG. 10A to 10C, and a preferred connection clip is illustrated in FIGS. 63A to 63D.

Figure 62:
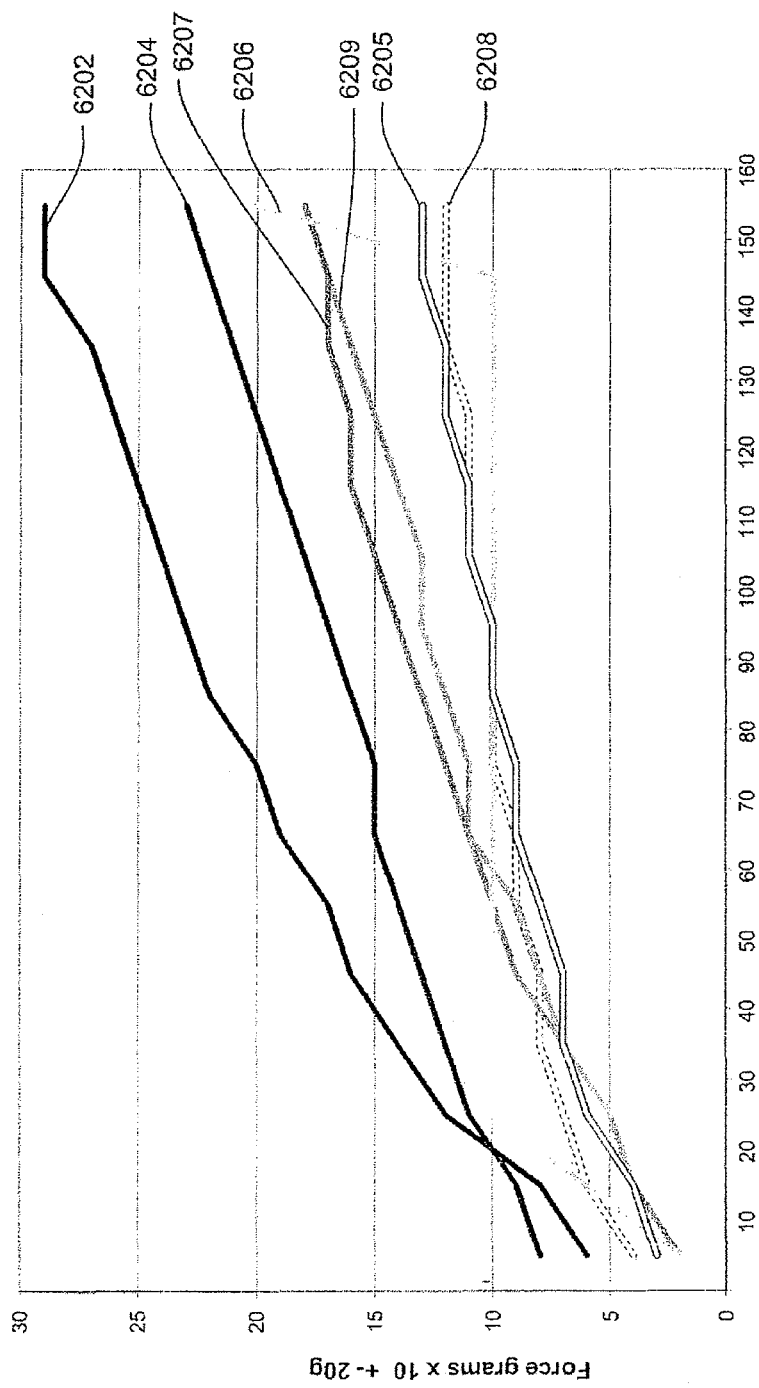
FIG. 62 is a graph of tested extension forces against extension of sample strap materials.

The single non-bifurcated strap preferably accommodates a substantial variation in head size without adjustment. The preferred strap has a very low stiffness with extension of a 400 mm king strap from a fully laid out but unstretched condition to a condition about 1.3 times its original length after applying a force not exceeding about 4N, and preferably not exceeding about 2N. FIG. 62 is a graph illustrating the force versus extension characteristics of four sample strap materials. The preferred material comprises a knitted or braided tube nylon yarn incorporating strands of Lycra. The nylon yarn is sufficiently loosely formed that it is capable of extension beyond the range required without becoming tight. The amount of Lycra strands in the yarn may be varied to vary the stiffness of the strap. An overall diameter or width of the strap is preferably less than about 10 mm and most preferably less than about 6 mm.

The end connectors of the strap may be fixed to the strap in any suitable manner. Preferably the end connectors are overmoulded to ends of the straps. Test results for a range of alternative strap materials are illustrated in FIG. 62. All test results are for extensions of a length of the tested material from an "at rest" length of about 400 mm.

Line 6202 shows extension test results for a knitted yarn of nylon incorporating Lycra filaments, the knitted tube having a nominal diameter of 5 mm. This also is stiffer than desirable.

Line 6206 illustrates a hypothetical most desirable response determined by the inventors.

Line 6209 illustrates the response for an extended silicone hollow tube with a wall thickness of about 0.25 mm and an outside diameter of about 3 mm.

Line 6207 illustrates the response for an extended silicone hollow tube with a wall thickness of about 0.25 mm and an outside diameter of about 6 mm.

Both of these silicone extensions show satisfactory characteristics.

Line 6205 illustrates the response of the preferred knitted nylon yarn incorporating Lycra filaments. This knitted tube had a nominal diameter of about 4 mm.

Line 6208 illustrates the response of a length of about 3 mm woven elastic webbing. This product exhibited similar characteristics to the preferred knitted yarn, however the elastic webbing has a tendency to catch hair and to lose elasticity.

The most preferred headstrap comprises a braided stretchable band. Lengths of stretchable thread are wound onto a plurality of spools. The spools of the thread are then used in a braiding machine to produce a continuous braided tube. The tube is passed over a roller or a plurality of rollers, or between rollers, to flatten the tube into a band.

The preferred headstrap has a cross-sectional dimension of about 6 mm wide and about 1.5 mm thick.

According to the most preferred embodiment, the thread comprises a Lycra (elastane or sprandex) strand with a spun wrapper. The elastane strand may be, for example, about 900 denier strand Lycra (elastane or spandex).

The spun wrapper may comprise at least one yarn of nylon filaments. The wrapper may comprise a primary wrapper yarn and a secondary wrapper yarn. Each yarn may comprise a spun yarn comprising a plurality of nylon filaments.

For example, each wrapper may comprise a yarn of nylon filaments.

The nylon filaments contribute the colour to the stretchable thread. For example, for a white headstrap, the nylon wrapper should comprise white nylon filaments.

In preparing a spool of the stretchy thread, preferably multiple threads (preferably three threads) of stretchy thread are wound onto the spool in parallel, so that each element in the braiding process actually comprises a bundle of three parallel threads.

Preferably, the braiding is conducted on a 16 spool braiding machine, such as a Ratera 16/80 braiding machine available from Talleres Ratera SA of Barcelona, Spain. Each spool of thread for the braiding is prepared with three parallel threads, as described above.

The braiding machine is configured (for example by setting tensions, speeds or both) to produce a suitable braid. Example settings for the Ratera 16 braiding machine speed control are A:45, B:20, C:30 and D:35.

Figure 64:
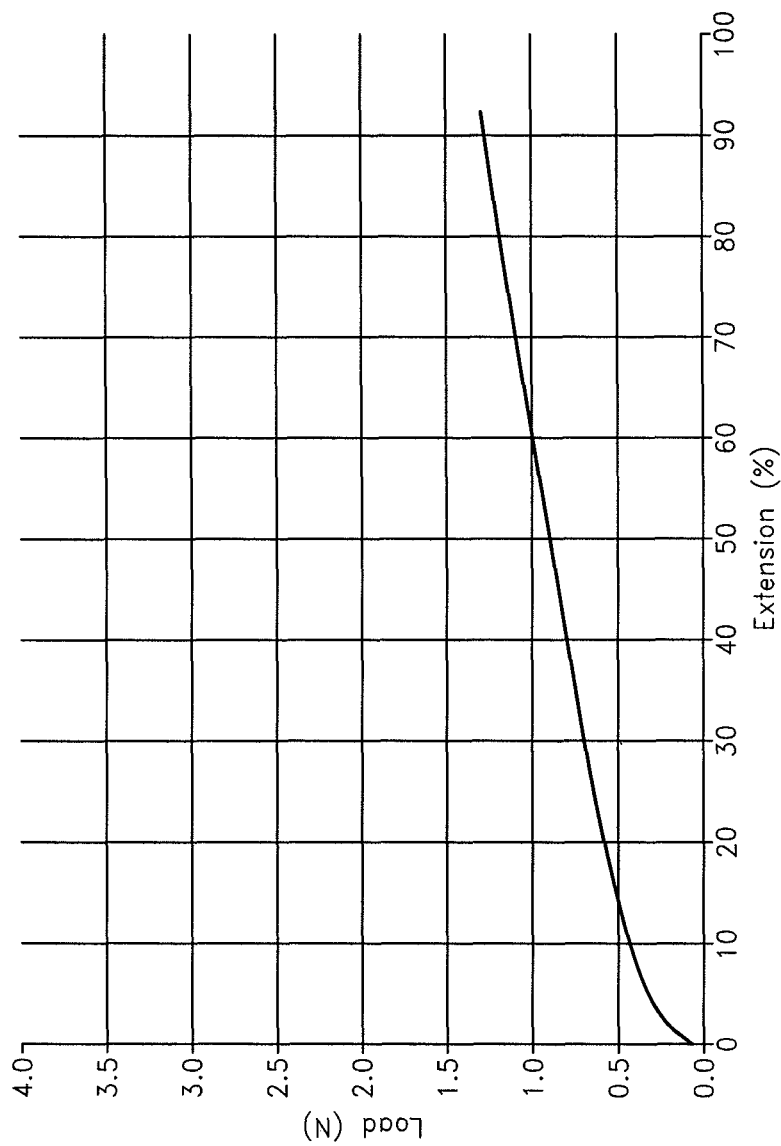
FIG. 64 is a graph of tested extension force against extension of another sample strap material.

A headstrap produced in accordance with this description was tested by gradual extension, with the force at each extension recorded. The force versus extension results for a 300 mm length of the prototype strap material are shown in FIG. 64.

Figure 63C:
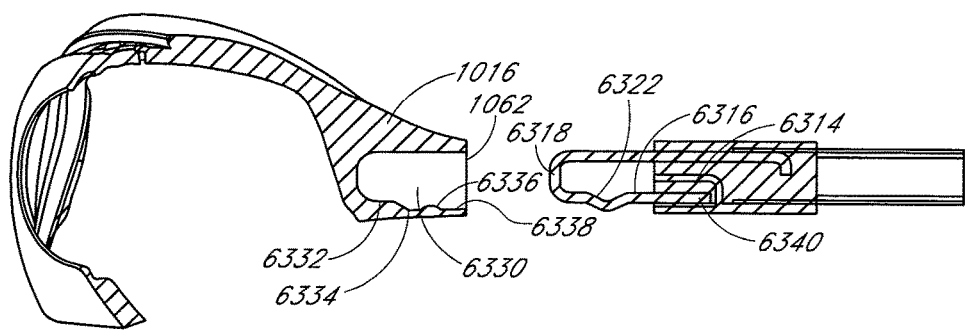
Figure 63D:
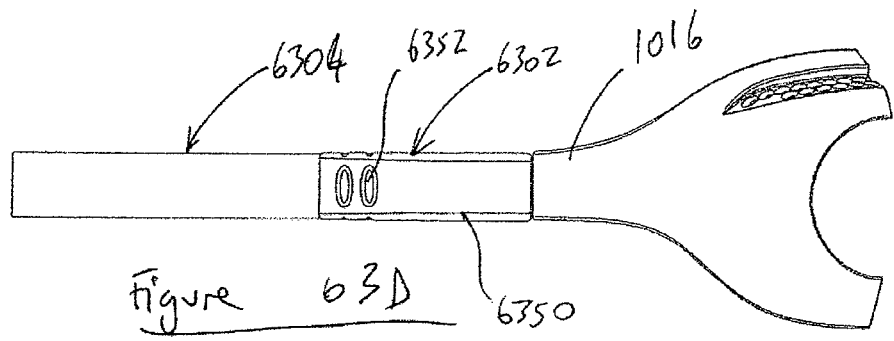
Figure 63E:
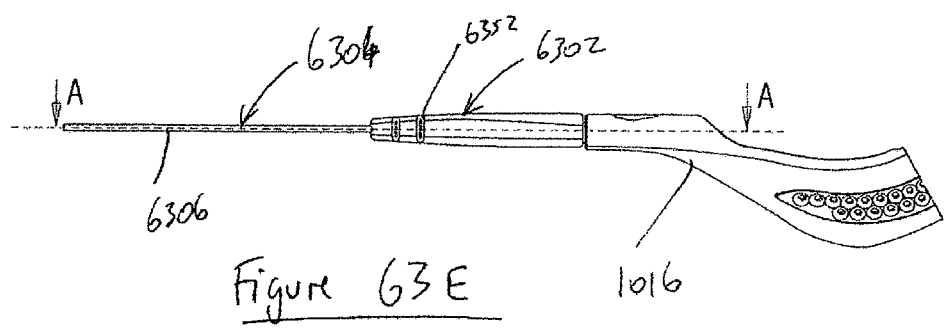
Figure 63F:
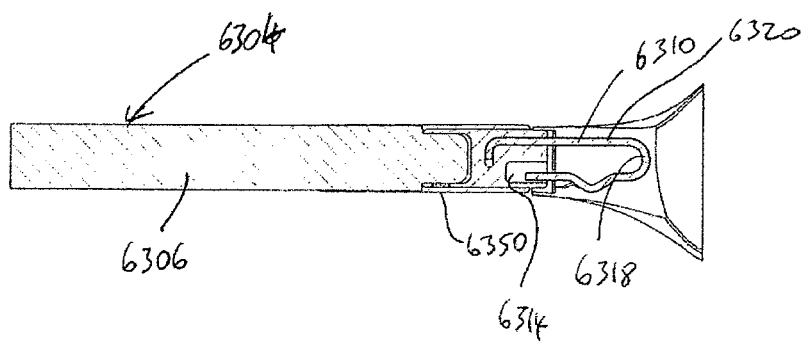

FIGS. 63A to 63C illustrate features of a preferred headgear strap. In particular they illustrate preferred arrangements for attaching a connector to an end of a suitable stretchy strap material. They also illustrate a preferred connector for connecting the strap to the frame of the interface.

FIGS. 63D to 63I illustrate another similar headgear strap which shares many of the features of the headgear strap of FIGS. 63A to 63C. Except where noted, the following description refers to both embodiments and reference numerals are shared.

At least one end of the strap 6304 is terminated, and preferably both ends are terminated, with a connector 6302. Once the complete interface is assembled, the connectors 6302 engage the side portions 1016 of the frame.

To form the connector, the flattened tube 6306 is encapsulated by a plastic body 6308 or 6350, for example but without limitation, by overmoulding.

In the embodiment of FIGS. 63D to 63J, the band is encapsulated by a comparatively soft material such as a thermoplastic elastomer.

The plastic body 6308 may have gripping features on its outer surfaces, such as bumps or ridges 6324 or recesses 6352.

The body 6308 terminates at its other end in an end face which is preferably sized and shaped to match the end face of side portions 1016. The connector and socket are preferably formed to provide a rigid connection between the connector and the frame such that, when engaged, the connector is a rigid extension of the side portion of the frame. According to this, the connectors contribute their length to the frame to define the location at which the soft straps depart the frame.

The preferred connection comprises a metal plug portion extending from the end face of the connector 6302 to engage in socket 1062 formed in the end face of the frame. The metal (preferably steel or titanium or similar material) plug portion has high stiffness and strength while retaining a compact form.

The plug portion may advantageously be formed from a metal wire 6310. For example the plug portion may be formed from a length of stainless steel wire.

The wire may be bent back upon itself and have both ends enclosed by the connector 6302, the wire thus forming a loop protruding from the end face of the connector. To cooperate with this loop the socket may be in the form of a slot with an overall shape to match the essentially flat prong formed by the loop.

The loop may include a limb 6316 including a protruding kink or hump. The protruding kink 6322 is adapted to engage in a shallow notch 6344 in the socket 1062. The notch 6344 may be formed along one edge surface of the slot.

The loop may be provided with a protruding end portion 6318 furthermost from the connector 6302. The slot may be provided with edge surfaces that closely match at least the lateral profile of the end portion 6318 so as to closely house the end portion with the loop engaged in the slot. This secures the connector against rotation in the plane of the loop.

The thickness of the slot preferably closely matches the thickness of the wire. This secures the connector against rotation transverse to the plane of the loop.

The loop may have a straight limb 6320, and the slot a complimentary straight edge face. These straight faces provide a sliding reference surface to align the connector with the socket during and after engagement.

Where one of the limbs of the wire loop is kinked and the other straight, and complimentary surfaces are provided in the slot, the connectors may be formed to have shapes which ensure correct orientation of the connectors relative to the socket. For example the connectors may have a form that is an apparent continuation of the form of the frame.

Where a connector and socket are provided at both ends of the strap, the connectors (and the sockets) may have reversed orientation. For example, one socket may have depression 6334 at the lower edge face and the other socket may have the depression at the upper edge face.

Alternatively the connectors may have a form or indication that ensures correct selection of the intended socket, as well as orientation relative to the selected socket.

As seen in FIGS. 63A and 63C, one of the main limbs of the wire loop may be free to move inside a cavity 6314 of the connector body 6308. Preferably, the free end 6340 is the end of the limb 6316 having the protruding kink. The small freedom to move within cavity 6314 allows the wire loop to deflect more than if the end were constrained. This deflection reduces the peak forces required (and generated in the socket) during connection and disconnection of the connector.

The cavity 6314 comprises a slot opening into the connector body 6308 from the end face of the connector body.

The other end of the wire loop may be formed to have a portion that is keyed into the material of the connector body. For example, a portion of the wire may be bent into a curve and overmoulded with plastic material of the connector body. This portion may overlap inside the connector body with the encapsulated end of the strap 6304.

For forming this connector, the wire loop and the strap may be assembled with a sleeve, and the assembly may be overmoulded. For example, the sleeve (which may be plastic), may have a blind cavity that receives the end 6340 of the wire loop, and an open ended cavity that receives the other end of the wire loop (through one end of the cavity) and the end of the strap (through the other end of the cavity). The sleeve may then be overmoulded, or at least the open ended cavity holding the strap and intended fixed end of the loop may be filled. Alternatively, the sleeve may be formed in two halves, clipped together over the wire loop. The two halves may, for example, be hinged together. The halves may also clip together over the end of the band 6306 and may roughly grip the end of the band before overmoulding. For example, gripping protrusions 6360 may engage the end 6362 of the band.

According to the embodiment of FIGS. 63D to 63J, the soft cover material 6350 is provided by overmoulding the connector with a soft material such as a thermoplastic elastomer along a length of the very flexible floppy band 6306 beyond the sleeve. This leads to a flexible portion 6370 transitioning between a rigid portion 6372 of the connector and the very supple strap. Preferably, this flexible portion is progressively more flexible moving away from the rigid portion 6372. For example, the overmoulded cover portion may taper extending away from the sleeve and indents may be provided in the cover (such as depressions 6352) or both.

On masks where the headgear strap will connect in a rigidly protruding fashion (such as in some of the embodiments of the masks described herein), the extending soft portion of the connector provides a soft buffer against impact from the protruding hard portion or prong.

Preferably, the soft portion extends from about 5 mm to about 60 mm along the band or strap, most preferably from about 10 mm to about 20 mm. The soft material may be chosen from a wide range of soft plastics with consideration given to bonding with the strap material and the sleeve material.

With this connector, one of the edge surfaces of the socket 1062 may include a first portion 6332 that matches the end portion 6318 of the loop, a depression or notch 6334 that matches the protruding kink 6322, a bump 6366 which secures the kink 6322 in the notch 6334, and a recessed lead in region 6338, which allows the loop to pass well into the slot before the largest connection force is used to push the kink 6322 past the bump 6366.

The described connector is compact, acts as an extension of the frame of the interface, and has a simple and intuitive method of connection and disconnection.

FIGS. 58 to 61 illustrate another patient interface incorporating a seal substantially as described earlier, and like FIGS. 10 to 12 includes features that may eliminate or reduce the need for additional support to the conduit. According to this embodiment, the body of the mask includes depending stabilizers 6102. A depending stabilizer is provided at each side of the mask body. Each depending stabilizer extends beyond the perimeter of the mask seal and includes a foot 6104 to engage against, above or in the vicinity of the upper lip of the wearer. Preferably, the stabilizer does not extend beyond the inside surface of the seal, but is spaced forward from the inside surface of the seal, with the feet 6104 located in a position such that with the mask donned and in use symmetrically on the patient, the feet 6104 of the depending stabilizers do not contact the wearer. Each foot 6104 may include a pad 6106 of soft material such as a soft polymer or elastomer foam or a section of hollow silicone extrusion, for example but without limitation. The stabilizers may be integrated with the seal rather than the frame, for example but without limitation, being integrally formed as a moulded silicone body extending from adjacent the central opening to protrude beyond the lower edge of the seal. In this case, features on the mask body could secure the position of the inboard ends of the stabilisers.

Each stabilizer extends in a downward direction to a region below the seal, and is intended to engage in the area of the upper lip of the patient in the area bounded by the mouth, the nose and the nasolabial folds and, preferably, not against the cheeks of the patient. Accordingly, the feet are profiled and positioned to fit within this area. Each stabilizer 6102 and arm 6108 extends from the lateral central portion 6110 of the illustrated mask body. The form of this arm, and the material of this arm may be such that the arm is rigid, or that the arm has a desired degree of flexibility. Generally, this arm should be somewhat rigid.

The purpose of the stabilizers is to reside closely spaced from the upper lip portion of the user when the interface is correctly placed and to contact the upper lip region of the user when the interface is rocked to one side or the other relative to the user's nose, for example, under the influence of the supply conduit. Gentle pressure on the foot 6104 of the stabilizer, which is laterally spaced from the centre line of the mask, preferably toward the extreme edges of the mask, supports the mask against these side forces from the conduit, stopping the mask rocking too far across the face and breaking the seal.

Furthermore, the stabilizers depend below the mask and support the mask if the weight of the conduit tends to rotate mask forward. In that case, the feet 6104 of both stabilizers will contact the user's upper lip and support the position of the mask.

The stabilizers are illustrated in preferred form as having a substantially rigid construction, but with flexible or soft pads 6106. However, to account for variations in patient geometry, these stabilizers could be a selectable appendage with a connection arrangement to the mask allowing replacement with stabilizers of a different form. Alternatively the stabilizers could be made to be adjusted, such as by providing hinge portions capable of multiple fixed positions along the length of the stabiliser, or at the junction of the arms and feet or both. Alternatively, the arms could be formed of a malleable material which is capable of substantial yield. According to this, the arms could be flexed into a desired position by yielding of the material and stay in that position. The soft pad of the stabilizer could be overmoulded onto portions of the frame. The frame and the stabilizers may be formed to have no sharp edges.

In the embodiment with hinging of the arms or feet, a linkage arrangement could be provided to link the movement of each of the stabilizers, or the stabilizers may be individually or collectively supported in position by a spring or springs or other resilient member.

With the addition of the stabilizers, the mask may be sufficiently secure and placed on the patient without any desire for additional support of the conduit. This in turn may allow a shorter length of flexible coupling tube 6120. Accordingly, the flexible coupling tube 6210 (which would typically be much more flexible than the main supply conduit) can be reduced in length to between about 5 cm and about 15 cm, and preferably about 10 cm. In systems that include a humidified gases supply and a heated main supply conduit, this short flexible coupling tube is usually unheated. Where the coupling tube needs to be supported by a lanyard or collar, there is a minimum length generally exceeding about 15 cm. If the requirement for the lanyard and collar is eliminated, the shorter coupling tube is only provided for flexibility, to de-couple the relatively rigid supply conduit from the mask and facilitate freedom of movement of the wearer's head. As the coupling tube is typically unheated, the humidity of the gases carried in the tube can rainout on the cooler wall surface creating collections of water which can ultimately be blown into the user's nostrils creating discomfort. Providing a shorter tube, as allowed by the lip stabilisers, reduces the likelihood of rainout in the conduit.

The interface configuration incorporating a single supple headstrap, a nasal seal, a low profile frame which can stabilise on the upper lip, all in a one size fits all package (preferably both the headstap and the seal) can be enhanced where the short coupling tube is especially supple. As used herein, the tube being supple means that it bends easily under applied forces. For example, suitable tubes may meet the test criteria explained below with reference to FIG. 65.

According to the test of FIG. 65, a 150 mm length of tube is clamped at each end to a cylindrical support at each end extending into the bore of the tube. This leaves approximately 130 mm of the tube suspended or bridging freely between the supported ends. This bridging portion should be in a relaxed state, neither contracted or extended. A lateral force of 5N at the centre of the tube should lead to a deflection greater than 13 mm.

A number of examples of patient interface aspects of the interfaces, and variations on each aspect, have been discussed with reference to other Figures. The present application contemplates that an interface may incorporate some aspects but not other aspects. For example, an interface might incorporate aspects of the mask while using a different arrangement for securing the mask to the user. An interface might include a different mask while using inventive aspects of the strap to secure that mask to the user. An interface may incorporate aspects of the mask but not make use of a similar, or any, structure for supporting the weight of the conduit from the body of the patient. All of these variations are considered within the scope of this application.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

What is claimed is:

1. A patient respiratory interface assembly comprising:
    a seal body assembly comprising a supple portion with a seal surface configured to form a seal around at least a nose of a user in use;

a frame assembly connected to a less supple portion of the seal body assembly, the frame assembly comprising first and second lateral sides, the frame assembly comprising:
- first and second strap connection points disposed on the first and second lateral sides, respectively, each of the first and second strap connection points being configured to receive a strap;
- first and second laterally extended flexible support arms disposed on the first and second lateral sides, respectively, each of the first and second laterally extended flexible support arms including a proximal portion and a distal portion, the distal portions of the first and second laterally extended flexible support arms including third and fourth strap connection points, respectively, the third and fourth strap connection points being disposed outwardly beyond a periphery of the supple portion of the seal body assembly, the third and fourth strap connection points being spaced vertically from the first and second strap connection points, respectively; and
- first and second webs of elastic material disposed adjacent to the proximal portions of the first and second laterally extended flexible support arms, respectively, at positions between the first and second laterally extended flexible support arms and the first and second strap connection points, respectively; and
- a strap assembly separate from yet connected to the frame assembly and extending around a back of a head of the user in use, the strap assembly comprising a first strap portion connected to the first strap connection point, a second strap portion connected to the second strap connection point, a third strap portion connected to the third strap connection point, and a fourth strap portion connected to the fourth strap connection point, the strap assembly pressing the frame assembly and seal body assembly against a user's face in use.

2. The patient respiratory interface assembly of claim 1, wherein the supple portion of the seal body assembly is configured to form the seal around at least the nose and a mouth of the user in use.

3. The patient respiratory interface assembly of claim 1, wherein the second strap connection point comprises at least an elongate slot at an end of the second laterally extended flexible support arm, the second strap portion being received through the elongate slot.

4. The patient respiratory interface assembly of claim 1 further comprising a conduit at a distal end of the seal body assembly, the conduit configured to provide gases to the seal body assembly, and a plurality of bias flow holes at the distal end of the seal body assembly, wherein the bias flow holes provide gas washout from the patient respiratory interface assembly.

5. A patient interface assembly comprising:
- a seal body assembly comprising a supple portion formed of a first material and a less supple portion formed of a second less pliant material, the supple portion comprising a periphery and a seal surface configured to form a seal around at least a nose of a user in use;
- a frame assembly connected to the less supple portion of the seal body assembly, the frame assembly comprising at least a first lateral side and a second lateral side, the first lateral side and the second lateral side comprising:
- first and second strap connection points, respectively, each of the first and second strap connection points being configured to receive a strap;
- first and second laterally extended flexible support arms, respectively, each of the first and second laterally extended flexible support arms including a proximal portion and a distal portion disposed outwardly beyond the periphery of the supple portion of the seal body assembly, the distal portions of the first and second laterally extended flexible support arms being spaced vertically from the first and second strap connection points, respectively; and
- first and second webs of elastic material, respectively, disposed adjacent to the proximal portions of the first and second laterally extended flexible support arms, respectively, the first web of elastic material being between the first laterally extended flexible support arm and the first strap connection point, the second web of elastic material being between the second laterally extended flexible support arm and the second strap connection point; and
- a strap assembly separate from yet connected to the frame assembly and extending around a back of a head of the user in use, the strap assembly comprising a first strap portion connected to the first strap connection point and a second strap portion connected to the second strap connection point.

6. The patient interface assembly of claim 5, wherein a supple portion of the seal body assembly is configured to form the seal around at least the nose and a mouth of the user.

7. The patient interface assembly of claim 5, wherein the first laterally extended flexible support arm comprises a third connection point at the distal portion configured to attach to a third strap portion of the strap assembly.

8. The patient interface assembly of claim 7, wherein the third connection point comprises at least an elongate slot, and wherein the third strap portion is removably received through the elongate slot.

9. The patient interface assembly of claim 8, wherein the strap assembly comprises a middle portion disposed adjacent a back of a head of the user in use, providing pressure on the patient interface assembly and helping seal the supple portion around the nose of the user.

10. The patient interface assembly of claim 5 further comprising a conduit at a distal end of the seal body assembly, wherein the conduit is configured to provide gases to the seal body assembly, and a plurality of bias flow holes disposed at the distal end of the seal body assembly, wherein the bias flow holes are configured to provide gas washout from the patient interface assembly.

11. The patient interface assembly of claim 5, wherein the second connection point and the second laterally extended flexible support arm are disposed on the second lateral side.

12. The patient interface assembly of claim 5, wherein the strap assembly comprises strips of foam and fabric.

13. The patient interface assembly of claim 5, wherein the less supple portion of the seal body assembly is fitted to the frame assembly.

14. The patient interface assembly of claim 5, wherein the first laterally extended flexible support arm is stiffer than the strap assembly.

15. A patient interface assembly comprising:
- a seal body assembly comprising a supple portion formed of a first material and a less supple portion formed of a second less pliant material, the supple portion comprising a periphery and a seal surface configured to form a seal around at least a nose of a user in use;
- a frame assembly connected to the less supple portion of the seal body assembly, the frame assembly including at least first and second flexible support arms and at least first and second upper connection points, the frame assembly further comprising first and second webs of elastic material, the first web of elastic material spanning between the first flexible support arm and the first upper connection point, the second web of elastic material spanning between the second flexible support arm and the second upper connection point; and a strap assembly separate from yet connectable to the frame assembly and configured to extend around a back of a head of the user in use, the strap assembly comprising first and second strap portions configured to connect to the first and second upper connection points.

16. The patient interface assembly of claim 15, wherein the first web of elastic material is more flexible than the first flexible support arm.

17. The patient interface assembly of claim 16, wherein the supple portion of the seal body assembly is configured to form the seal around at least the nose and a mouth of the user.

18. The patient interface assembly of claim 16, wherein the first flexible support arm comprises a distal end with the second upper connection point configured for attachment to the second strap portion.

19. The patient interface assembly of claim 16 further comprising a conduit at a distal end of the seal body assembly, wherein the conduit is configured to provide gas to the seal body assembly, and a plurality of bias flow holes disposed at the distal end of the seal body assembly, wherein the bias flow holes provide gas washout from the patient interface assembly.

* * * * *